(12) United States Patent
Han et al.

(10) Patent No.: US 11,207,376 B2
(45) Date of Patent: *Dec. 28, 2021

(54) PROTEINS FOR THE TREATMENT OF EPITHELIAL BARRIER FUNCTION DISORDERS

(71) Applicant: Second Genome, Inc., South San Francisco, CA (US)

(72) Inventors: Andrew Wonhee Han, South San Francisco, CA (US); Andrew Whitman Goodyear, South San Francisco, CA (US); Tarunmeet Gujral, South San Francisco, CA (US); Todd Zachary Desantis, South San Francisco, CA (US); Karim Dabbagh, South San Francisco, CA (US); Toshihiko Takeuchi, South San Francisco, CA (US); Ye Jin, South San Francisco, CA (US); Michi Izumi Willcoxon, South San Francisco, CA (US); Stefanie Banas, South San Francisco, CA (US)

(73) Assignee: Second Genome, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/603,507

(22) PCT Filed: Apr. 6, 2018

(86) PCT No.: PCT/US2018/026447
§ 371 (c)(1),
(2) Date: Oct. 7, 2019

(87) PCT Pub. No.: WO2018/187682
PCT Pub. Date: Oct. 11, 2018

(65) Prior Publication Data
US 2020/0148728 A1    May 14, 2020

Related U.S. Application Data

(60) Provisional application No. 62/482,963, filed on Apr. 7, 2017, provisional application No. 62/607,706, filed on Dec. 19, 2017, provisional application No. 62/611,334, filed on Dec. 28, 2017.

(51) Int. Cl.
| | |
|---|---|
| A61K 39/00 | (2006.01) |
| A61K 39/38 | (2006.01) |
| A61K 39/08 | (2006.01) |
| A61K 39/02 | (2006.01) |
| A61P 1/04 | (2006.01) |
| C07K 2/00 | (2006.01) |
| A61K 38/16 | (2006.01) |
| A61P 37/02 | (2006.01) |
| C07K 14/33 | (2006.01) |
| C07K 14/195 | (2006.01) |
| A61K 38/00 | (2006.01) |

(52) U.S. Cl.
CPC ............... *A61K 38/16* (2013.01); *A61P 1/04* (2018.01); *A61P 37/02* (2018.01); *C07K 2/00* (2013.01); *C07K 14/195* (2013.01); *C07K 14/33* (2013.01); *A61K 38/00* (2013.01)

(58) Field of Classification Search
CPC ....................................................... A61K 38/16
See application file for complete search history.

(56) References Cited

U.S. PATENT DOCUMENTS

| | | | |
|---|---|---|---|
| 4,399,216 | A | 8/1983 | Axel |
| 5,767,063 | A | 6/1998 | Lee |
| 9,196,762 | B2 | 10/2015 | Kelly et al. |
| 10,251,933 | B2 | 4/2019 | Han |
| 2012/0165262 | A1 | 6/2012 | Polk |
| 2015/0071957 | A1 | 3/2015 | Kelly |
| 2016/0279177 | A1 | 9/2016 | Kelly |
| 2018/0289770 | A1 | 10/2018 | Han |
| 2020/0171125 | A1* | 6/2020 | Han ................. C07K 14/195 |

FOREIGN PATENT DOCUMENTS

| | | |
|---|---|---|
| WO | WO 2013/050792 | 4/2013 |
| WO | WO 2016203221 | 12/2016 |
| WO | WO 2018187682 | 10/2018 |
| WO | WO2018/223051 | 12/2018 |

OTHER PUBLICATIONS

Travis et al., Genome Announc, 2015; 3(6):e01286-15 (Year: 2015).*
World Health Organization (WHO) model prescribing information: Drugs used in Bacterial Infections, 2001; report series No. 895: 1-179 (Year: 2001).*
Mayo Clinic, https://www.mayoclinic.org/diseases-conditions/metabolic-syndrome/diagnosis-treatment/drc-20351921, accessed Mar. 27, 2020 (Year: 2020).*
Heathline.com, https://www.healthline.com/health/liver-diseases, accessed Mar. 27, 2020, pp. 1-14 (Year: 2020).*
Clevelandclinic.org, https://my.clevelandclinic.org/health/articles/7040-gastrointestinal-disorders, accessed Mar. 27, 2020 (Year: 2020).*
MedlinePlus, https://medlineplus.gov/neurologicdiseases.html, accessed Mar. 27, 2020 (Year: 2020).*

(Continued)

*Primary Examiner* — Gary B Nickol
*Assistant Examiner* — Lakia J Jackson-Tongue
(74) *Attorney, Agent, or Firm* — Fish & Richardson P.C.

(57) ABSTRACT

The disclosure relates to therapeutic proteins and pharmaceutical compositions comprising said proteins, which have utility in treating various human diseases. In particular aspects, the disclosed therapeutic proteins are useful for treating human gastrointestinal inflammatory diseases and gastrointestinal conditions associated with decreased epithelial cell barrier function or integrity. Further, the disclosed therapeutic proteins are useful for treating human inflammatory bowel disease, including inter alia, Crohn's disease and ulcerative colitis.

24 Claims, 23 Drawing Sheets
Specification includes a Sequence Listing.

(56) References Cited

OTHER PUBLICATIONS

Bowie et al., Science, 1990, 257:1306-1310 (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Ma (Modern Drug Discovery 2004, 7(6)) (Year: 2004).*
Sanger et al (Therap Adv Gastroenterol. Sep. 2010;3(5):291-305) (Year: 2010).*
Odenwald et al. (Nat Rev Gastroenterol Hepatol. Jan. 2017;14(1):9-21) (Year: 2017).*
Chelakkot et al. (Experimental & Molecular Medicine (2018) 50:103) (Year: 2018).*
Altschul et al., "Basic local alignment search tool", J. Mol. Biol. 215: 403-410, 1990.
Altschul et al., "Gapped BLAST and PSI-BLAST: a new generation of protein database search programs", Nucleic Acids Res. 25(17): 3389-3402, 1997.
Antonsson et al., "Induction of apoptosis by staurosporine involves the inhibition of expression of the major cell cycle proteins at the G(2)/m checkpoint accompanied by alterations in Erk and Akt kinase activities." Anticancer Res., 29 (8): 2893-2898, 2009.
Aroniadis et al. "Fecal microbiota transplantation: past, present and future." Curr. Opin. Gastroenterol. 29 (1): 79-84, 2013.
Ayoubi et al., "Regulation of gene expression by alternative promoters.", FASEB J. 10, 453-60, 1996.
Baron et al., "Variation Between Observers in Describing Mucosal Appearances in Proctocolitis", BMJ, 1: 89, 1964.
Beduneau et al., "A tunable Caco-2/HT29-MTX co-culture model mimicking variable permeabilities of the human intestine obtained by an original seeding procedure." Eur J Pharm Biopharm., 87 (2): 290-298, 2014.
Behrendt et al., "Lipopolysaccharide binding protein in preterm infants.", Arch Dis Child Fetal Neonatal Ed 89: F551-554, 2004.
Berge et al., "Pharmaceutical salts", J. Phann. Sci. 66: 1-19, 1977.
Berger et al., "Oleic Acid Uptake Reveals the Rescued Enterocyte Phenotype of Colon Cancer Caco-2 by HT29-MTX Cells in Co-Culture Mode", Int J Mol Sci, 18: 1573, 21 pages, 2017.
Best et al., "Development of a Crohn's disease activity index.", National Cooperative Crohn's Disease Study, Gastroenterol. 70: 439-444, 1976.
Bibiloni et al.,"VSL#3 probiotic-mixture induces remission in patients withactive ulcerative colitis." Am J Gastroenterol., 100 (7): 1539-1546, 2005.
Boltin et al., Mucin Function in Inflammatory Bowel Disease an Update. J. Clin. Gastroenterol., 47 (2): 106-111, 2003.
Botoman et al., "Management of Inflammatory Bowel Disease." Am Fam Physician 57 (1): 57-68, 1998.
Bratt et al., "A phase 1 trial with transgenic bacteria expressing interleukin-IO in Crohn's disease," Clinical Gastroenterology and Hepatology, vol. 4, pp. 754-759, 2006.
Bratt et al., "A phase 1 trial with transgenic bacteria expressing interleukin-IO in Crohn's disease." Clinical Gastroenterology and Hepatology 4: 754-759, 2006.
Cani et al., "Changes in Gut Micro biota Control Metabolic Endotoxemia-lnduced Inflammation in High-Fat Diet-Induced Obesity and Diabetes in Mice." Diabetes 57: 1470-1481, 2008.
Coskun et al., "Intestinal Epithelium in Inflammatory Bowel Disease." Frontiers in Medicine 1: 24, 2014.
Danese et al., "Etiopathogenesis of inflammatory bowel diseases." World J. Gastroenterol., 12: 4807-4812, 2006.
Daperno et al., "Results of the 2nd part Scientific Workshop of the ECCO. II: Measures and markers of prediction to achieve, detect, and monitor intestinal healing in inflammatory bowel disease.", J Crohns Colitis., 5: 484-498, 2011.
Delzenne et al., "Targeting gut microbiota in obesity: effects of prebiotics and probiotics." Nature Reviews, 7 (11): 639-646, 2011.
Dewi et al., "In vitro assessment of human endothelial cell permeability: effects of inflammatory cytokines and dengue vims infection," J Virol Methods., 121 (2): 171-180, 2004.

Dewi et al., "Peripheral blood mononuclear cells increase the permeability of dengue virus-infected endothelial cells in association with down-regulation of vascular endothelial cadherin", J. Gen. Virol. 89: 642-652, 2008.
Duncan et al., "Proposal of *Roseburia faecis* sp. nov., *Roseburia hominis* sp. nov. and *Roseburia inulinivorans* sp. nov., based on isolates from human faeces." Int J Syst Evol Microbial., 56(Pt 10): 2437-2441, 2006.
Durrer et al., "Genetically engineered probiotic for the treatment of phenylketonuria (PKU); assessment of a novel treatment in vitro and in the PAHenu2 mouse model of PKU." PLoS One., 12(5): e0176286, 17 pages, 2017.
Everard et al., "Cross-talk between Akkermansia muciniphila and intestinal epithelium controls diet-induced obesity." PNAS, 110 (22): 9066-9071, 2013.
Everard et al., "Responses of Gut Micro biota and Glucose and Lipid Metabolism to Prebiotics in Genetic Obese and Diet-Induced Leptin-Resistant Mice." Diabetes, 60 (11): 2775-2786, 2011.
Frottin et al., "The Proteomics of N-terminal Methionine Cleavage," Molecular & Cellular Proteomics 5.12, pp. 2336-2349, 2006.
G2T1 E5 Uniprot, Downloaded From https://www.uniprot.org/uniprot/G2T1 E5; Last Modified Nov. 16, 2011, 2011).
Gassler et al., "Inflammatory bowel disease is associated with changes of enterocytic junctions." Am J. Phvsiol. Gastrointest. Liver Phvsiol., 28 (1): G216-G228, 2001.
Gaston et al., "S-nitrosylation signaling in cell biology.", Mol Interv. 3, 253-263, 2003.
Glozak et al., "Acetylation and deacetylation of non-histone proteins.", Gene. 363, 15-23, 2005.
Han et al., "Detergent-free biotin switch combined with liquid chromatography/tandem mass spectrometry in the analysis of S-nitrosylated proteins.", Rapid Commun Mass Spectrom. 22, 1137-1145, 2008.
Hanniffy et al., "Mucosal delivery of a pneumococcal vaccine using Lactococcus lactis affords protection against respiratory infection," Journal ofInfectious Diseases, 195 (2): 185-193, 2007.
Harvey et al., "A Simple Index of Crohns-Disease Activity", Lancet 1(8178): 1134-1135, 1980.
Henikoff et al., "Amino acid substitution matrices from protein blocks", Proc. Natl. Acad. Sci. 89(22): 10915-10919, 1992.
Horhota et al., "Glycerol nucleoside triphosphates: Synthesis and polymerase substrate activities", Organic Letters 8: 5345-5347, 2006.
Hsiao et al., "High-frequency transformation of yeast by plasmids containing the cloned yeast ARG4 gene", Proc. Natl. Acad. Sci. (USA), 76: 3829, 1979.
Huynh et al., "Probiotic preparation VSL#3 induces remission in children with mild to moderate acute ulcerative colitis: a pilot study." Inflamm Bowel Dis., 15 (5): 760-768, 2009.
Imai et al., "Transcriptional silencing and longevity protein SIR2 is an NADdependent histone deacetylase.", Nature. 403, 795-800, 2000.
International Search Report and Written Opinion, dated Aug. 23, 2018, for International Application No. PCT/US2018/026447, 17 pages.
Irvine et al., "Quality of Life: A Valid and Reliable Measure of Therapeutic Efficacy in the Treatment of Inflammatory Bowel Disease", Gastroenterology 106: 287-296, 1994.
Jaffrey et al., "The Biotin Switch Method for the Detection of S-Nitrosylated Proteins.", Sci. STKE. 2001.
Johansson et al., "Bacteria penetrate the normally impenetrable inner colon mucus layer in both murine colitis models and patients with ulcerative colitis." Gut., 63 (2): 281-291, 2014.
Karlin et al., Applications and statistics for multiple high-scoring segments in molecular sequences, Proc. Natl. Acad. Sci. 90: 5873-5877, 1993.
Kiesler et al., "Experimental Models of Inflammatory Bowel Diseases.", Cell Mol Gastroenterol Hepatol, vol. 1, No. 2, pp. 154-170, 2015.
Kim et al., "Investigating Intestinal Inflammation in DSS-induced Model of IBD." Journal of Visualized Experiments, 60: pii: 3678, 171-180, 2012.
Kyte and Doolittle, "A Simple Method for Displaying the Hydropathic Character of a Protein", J Mol. Biol. 157: 105-132, 1982.

(56) References Cited

OTHER PUBLICATIONS

Lerner et al., "Dysbiosis may trigger autoimmune diseases via inappropriate posttranslational modification of host proteins." Frontiers in Microbiology, vol. 7, Article 84, 2016.
Levesque et al., "Converging goals of treatment of inflammatory bowel disease from clinical trials and practice." Gastroenterology, 148 (1): 37-51.e1, 2015.
Machiels et al., "A decrease of the butyrate-producing species *Roseburia hominis* and *Faecalibacterium prausnitzii* defines dysbiosis inpatients with ulcerative colitis." Gut., 63 (8): 1275-1283, 2014.
Maloy et al., "Intestinal homeostasis and its breakdown in inflammatory bowel disease.", Nature 474 (7351): 298-306, 2011.
Mandic et al., "Evaluation of head and neck squamous cell carcinoma invasiveness by the electrical resistance breakdown assay." Clin Exp Metastasis, 21 (8): 699-704, 2004.
Mansour et al., "Disruption of the proto-oncogene int-2 in mouse embryo-derived stem cells: a general strategy for targeting mutations to non-selectable genes.", Nature, 336: 348-352, 1988.
Markus et al., "Cytokines in Inflammatory Bowel Disease." Nature Reviews Immunology, 14 (5): 329-342, 2014.
Martini et al., "Mend Your Fences: The Epithelial Barrier and Its Relationship With Mucosal Immunity in Inflammatory Bowel Disease." Cellular and Molecular Gastroenterology and Hepatology 4 (1): 33-46, 2017.
McCormick et al., "Mucin depletion in inflammatory bowel disease," Journal of Clinical Pathology, 43: 143-146, 1990.
Moayyedi et al., "Fecal Microbiota Transplantation Induces Remission in Patients With Active Ulcerative Colitis in a Randomized Controlled Trial." Gastroenterology 149 (1): 102-109.e6, 2015.
Molodecky et al., "Increasing incidence and prevalence of the inflammatory bowel diseases with time, based on systematic review." Gastroenterology 142 (1): 46-54.e42, 2012.
Myers et al., "Optimal alignments in linear space", CABIOS 4: 11-17, 1988.
Narula et al., "Fecal Microbiota Transplantation for Treatment of Active Ulcerative Colitis." Inflamm Bowel Dis., 23 (10): 1702-1709, 2017.
NCBI Protein Blast for SEQ ID No. 19 (downloaded from https://blast.ncbi.nlm.nih.gov/Blast.cgi#alnHdr_ 1473652184 on Oct. 28, 2018, 2018.
NCBI reference for WP _014079420.1 (downloaded from https://www.ncbi.nlm.nih.gov/protein/WP014079420.1 ?report=genbank &log$=protalign&blast_rank=1&RID-XCKE8H21015; Published May 18, 2013.
Needleman et al., "A general method applicable to the search for similarities in the amino acid sequence of two proteins", J. Mol. Biol., 48(3): 444-453, 1970.
Nuerath, "Cytokines in Inflammatory Bowel Disease." Nature Reviews Immunology 14 (5): 329-342, 2014.
Paine, "Colonoscopic evaluation in ulcerative colitis.", Gastroenterol Rep 2: 161-168, 2014.
Pan et al., "Oral administration of Lactobacillus paracasei alleviates clinical symptoms of colitis induced by dextran sulphate sodium salt in BALB/c mice." Benef Microbes., 5 (3): 315-322, 2014.
Patterson et al., "Human Gut Symbiont Roseburia hominis Promotes and Regulates Innate Immunity." Front lmmunol., 8: 1166, 2017.
Pearson et al., "Improved tools for biological sequence comparison", Proc. Natl. Acad. Sci. 85: 2444-2448, 1988.
Plovier et al., "A purified membrane protein from Akkermansia muciniphila or the pasteurized bacterium improves metabolism in obese and diabetic mice." Nat Med., 23 (1): 107-113, 2017.
Qazi et al., "The risk of inflammatory bowel disease flares after fecal microbiota transplantation: Systematic review and meta-analysis." Gut Microbes., 8 (6): 574-588, 2017.
Rachmilewitz, "Coated mesalazine (5-aminosalicylic acid) versus sulphasalazine in the treatment of active ulcerative colitis: a randomised trial", BMJ, 298: 82-86, 1989.
Sands et al., "Infliximab Maintenance Therapy for Fistulizing Crohn's Disease", N Engl J Med 350 (9): 876-885, 2004.
Sands, "From symptom to diagnosis: clinical distinctions among various forms of intestinal inflammation." Gastroenterology 126 (6): 1518-1532, 2004.
Shawki et al. "Mechanisms of Intestinal Epithelial Barrier Dysfunction by Adherent-Invasive *Escherichia coli*." Cell Mol Gastroenterol Hepatol., 3 (1): 41-50, 2016.
Sheth et al., "Manipulating bacterial communities by in situ microbiome engineering." Trends in Genetics 32 (4): 189-200, 2016.
Shigemori et al., "Oral delivery of Lactococcus lactis that secretes bioactive heme oxygenase-1 alleviates development of acute colitis in mice." Microbial Cell Factories 14: 189, 2015.
Simmonds et al., "Paneth cell metaplasia in newly diagnosed inflammatory bowel disease in children." BMC Gastroenterol., 14: 93, 2014.
Srinivasan et al., "TEER measurement techniques for in vitro barrier model systems." J Lab Autom., 20 (2): 107-126, 2015.
Srutkova et al., "Bifidobacterium longum CCM 7952 Promotes Epithelial Barrier Function and Prevents Acute DSS-lnduced Colitis in Strictly Strain-Specific Manner." PLoS One, 10 (7): e0134050, 2015.
Steidler et al., "Treatment of murine colitis by Lactococcus lactis secreting interleukin-IO." Science 289 (5483): 1352-1355, 2000.
Strober et al., "Proinflammatory cytokines in the pathogenesis of inflammatory bowel diseases." Gastroenterology, 140 (6): 1756-1767, 2011.
Sturm et al., "Epithelial restitution and wound healing in inflammatory bowel disease," World J Gastroenterol, 14(3): 348-353, 2008.
ThermoFisher: www.thermofisher.com/us/en/home/lifo-science/cloning/genesynthesis/geneart-gene-synthesis/geneoptimizerhtm, "Invitrogen GeneArt Gene Synthesis", 4 pages, 2017.
Thia et al., "Measurement of Disease Activity in Ulcerative Colitis: Interobserver Agreement and Predictors of Severity", Inflamm Bowel Dis, 17: 1757-1764, 2011.
Travis et al., "Developing an instrument to assess the endoscopic severity of ulcerative colitis: the Ulcerative Colitis Endoscopic Index of Severity (UCEIS)", Gut, 61: 535-542, 2012.
Ulcerative Colitis: Introduction Johns Hopkins Medicine, found at: www.hopkinsmedicine.org/gastroenterology hepatology / pdfs/ small large intestine/ulcerative_colitis. pdf., 14 pages, 2013.
UniProtKB—G2T1 E5 (G2T1 E5_ROSHA), Nov. 16, 2011, 4 pages. Retrieved from: https://www.uniprot.orq/uniproUG2T1 E5.
Van Solingen et al., "Fusion of Yeast Spheroplasts", J. Bact, 130: 946-947, 1977.
Vandenbroucke et al., "Active delivery of trefoil factors by genetically modified Lactococcus lactis prevents and heals acute colitis in mice." Gastroenterology, 127 (2): 502-513, 2004.
Yan et al., "Colon-specific delivery of a probiotic-derived soluble protein ameliorates intestinal inflammation in mice through an EGFR-dependent mechanism." J Clin Invest., 121 (6): 2242-2253, 2011.
Yang et al., "Lysine acetylation: Codified crosstalk with other posttranslational modifications.", Mol Cell. 31, 449-461, 2008.
Zhang et al., "Cytokines, Inflammation and Pain", Int. Anesthesiol. Clin. 45(2): 27-37, 2007.
Zolotaresky et al., "A membrane-permeant peptide that inhibits MLC kinase restores barrier function in in vitro models of intestinal disease." Gastroenterology 123 (1): 163-172, 2002.
ATUM.com[online], "GPS Technology," n.d. URL< www.atum.bio/services/genegps> 5 pages.
Chassaign et al., "Dextran sulfate Sodium(DSS)-Induced Colitis in Mice" Curr Protoc Imunol, Feb. 2014,104: Unit-15.25.
European Extended Supplemental Search Report in International Appln. No. PCT/US2018026447,dated Dec. 22, 2020, 9 pages.
GenBank Accession No. AEN96375, hypothetical protein RHOM_06280[Roseburia homonis A2-183], Nov. 24, 2015, 1 page.
GenBank Accession No. AJ270482, "Roseburia hominis," Oct. 2006, 56(10): 2437-2441.
GenBank Accession No. CP003040, "Roseburia hominis A2-183, complete genome," Nov. 24, 2015, 112 pages.
Higgins et al., "CLUSTAL: a package for performing multiple sequence alignment on a microcomputer", Gene 73: 237-244, 1988.

(56) References Cited

OTHER PUBLICATIONS

Idtdna.com [online], Integrated DNA Technologies: retrieved on Jun. 18, 2020, from URL<www.idtdna.com/CodonOpt.> 4 pages.

Inouye et al. Cloninc Squence analysis of cDNA for the luminescent protein aequorin. Proceedings of the National Academy of Sciences, May 1985, 82(10):3154-3158.

International Human Genome Sequencing Consortium, "Finishing the euchromatic sequence of the human genome," Nature. 431, 931-45, 2004.

IUPAC Commission on the Nomenclature of Organic Chemistry (CNOC) and IUPAC-IUB Commission on Biochemical Nomenclature (CBN), Nomenclature of a Amino Acids, (Recommendations 1974), Biochemistry 14: 449-462, 1975.

Jensen, "Modification-specific proteomics: Characterization of post-translational modifications by mass spectrometry.", Curr Opin Chem Biol. 8, 33-41, 2004.

Matts, "The value of rectal biopsy in the diagnosis of ulcerative colitis.", QJM, 30: 393-407, 1961.

Merrifield. J., "Solid Phase Peptide Synthesis. I. The Synthesis of a Tertrapeptide," Am Chem Soc., 85: 2149-2154, 1963.

PCT International Preliminary Report on Patentability in International Appln. No. PCT/US2019/026412, dated Oct. 6, 2020, 5 pages.

PCT International Search Report and Written Opinion in International Appln No. PCT/US2019/026412, dated Aug. 20, 2019, 8 pages.

Schroeder et al., "Coated Oral 5-Aminosalicyclic Acid Therapy for Mildly to Moderate Active Ulcerative Colitis," N Eng J Med, 317: 1625-1629, 1987.

Sutherland et al., 5-Aminosalicylic acid enema in the treatment of distal ulcerative colitis, Proctosigmoiditis, and Proctitis, Gastroenterology, 1987,92: 1994-1998.

Tilg et al., Roseburia hominis: a novel guilty player in ulcerative colitis pathogenesis,? Gut, Oct. 2013, 63:8:1204-1205.

Zhang et al., "Interactions between intestinal microbiota and host immune response in inflammatory bowel disease," Frontiers in Immunology, Aug. 2017, 8:942:1-13.

\* cited by examiner

FIG. 17

```
SG-11          1  MLEGEESVVY VGKKGVIASL DVETLDQSYY DETELKSYVD AEVEDYTAEH
WP_006857001_1    MLDADTDTVY VQKNGTVLSV DVETLDKDYY DETELKDYVT DAVSTYTGEH
WP_075679733_1    MLDVEESTVY VQKNGSVIST DIEDFSADYY DEDELKDYIG DEISSYTSEN
WP_055301040_1    MLEADTNTVY VSKHGKVVSM DVEQLDQSYY DETELKEFVD SAVDEYNTEN 51                                                  100
SG-11             GKNAVKVESL KVEDGVAKLK MKYKTPEDYT AFNGIELYQG KVVASLAAGY
WP_006857001      GKSAVKLENL SVKDGTATLK MKYKTPEDYT GFNGIELYEG KVVKALAAGY
WP_075679733      GKKSVSLESV SVKDSVAKLT MKYKTAEDYT NFNGVELYTG TIVKAMAAGY
WP_055301040      GKNSVKVDDL TVEDGTAKLR MDYETVDDYT AFNGVELYEG KIVQALAAGY 101                                                 150
SG-11             VYDGEFARVE EGKVVGAATK QDIYSEDDLK VAIIRANTDV KVDGEICYVS
WP_006857001      DFKTDFVSVE DGKVTGTATK EEIYSGEDLK VVIIKANRDV KVDGTICYVS
WP_075679733      DFGVDFVSVK DGAVTGTATK DEIVDHDDYK VAVIKANTDV KVDGTIVYVS
WP_055301040      DFDTDFAGVD KDGCVTGVTR GDILAQEDLK VVIIKANTDV KIDGKILYVS 151                                                 200
SG-11             CQNVKLTGKD SVSIRDGYYL ETGSVTASVD VTGQESVGTE QLSGTEQMEM
WP_006857001      SENVKLTGTD SVSIRDGYSL NSGSTADESD SDENIADGTE SIGGSTEV..
WP_075679733      SQNVKVTGKN TVSIREGYLA ADTTNVVGS. ........TE TVAET.....
WP_055301040      CDNVTVTGKD SVSIKEGTGI EKTWITEAEE VPST.....E AVLETESTED 201                                    241
SG-11             TGEPVN.... ....ADDTEQ TEAAAGDGSF ETDVYTFIVY K
WP_006857001      ....SD.... ....TDVNDD TTYVKDDGAF ETDVYTYIIY K
WP_075679733      ....EA.... ....EEANQT EAVLEDEFAS ESDVYTYVIF K
WP_055301040      AGDVIEGEVI IGTEEASGND VVTNLSGGSS GTDVYTYIIY K
```

SG-11: SEQ ID NO:7
WP_006857001: SEQ ID NO:21
WP_075679733: SEQ ID NO:22
WP_055301040: SEQ ID NO:23

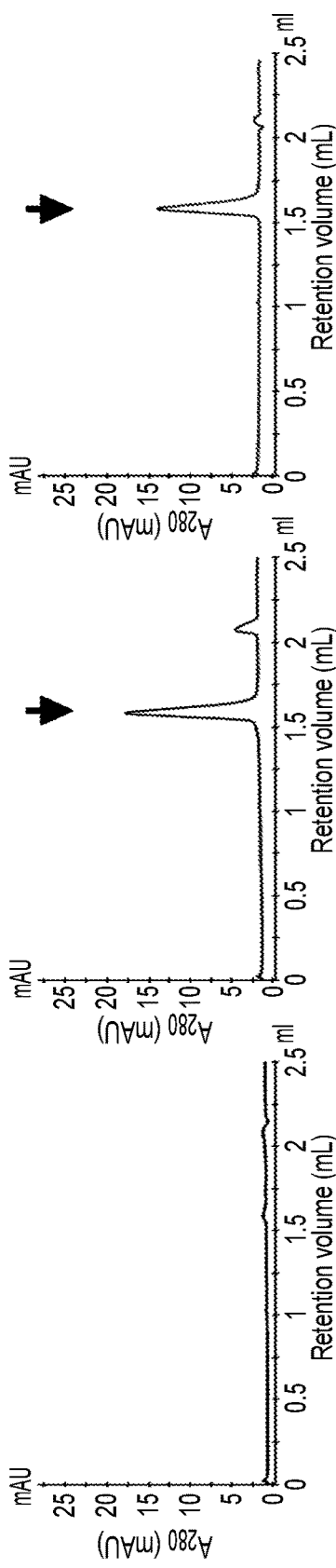
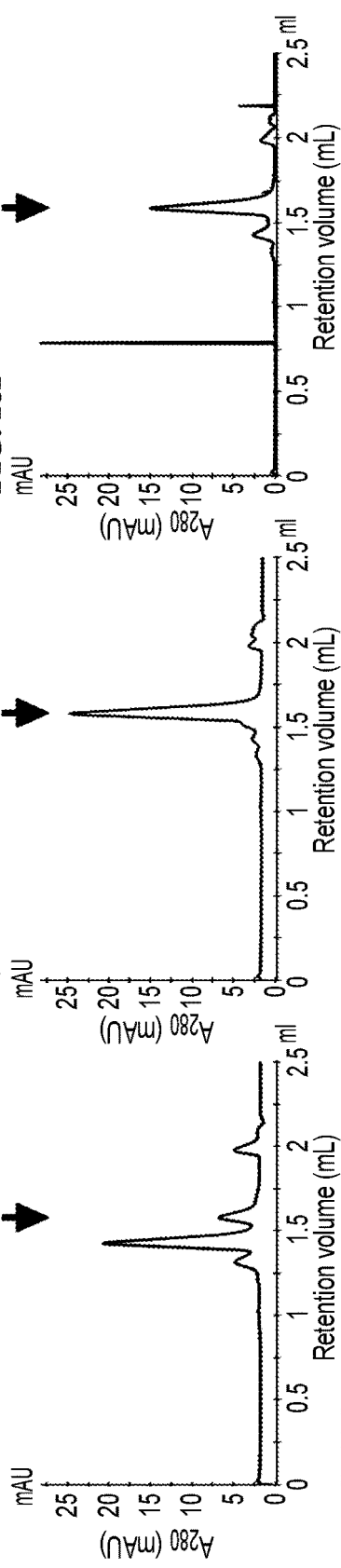
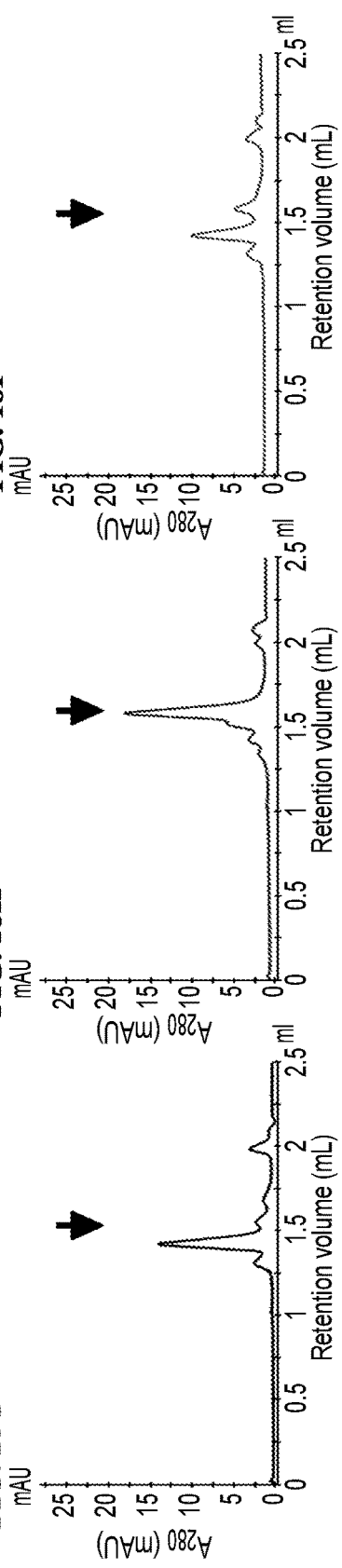
FIG. 18A FIG. 18B FIG. 18C
FIG. 18D FIG. 18E FIG. 18F
FIG. 18G FIG. 18H FIG. 18I

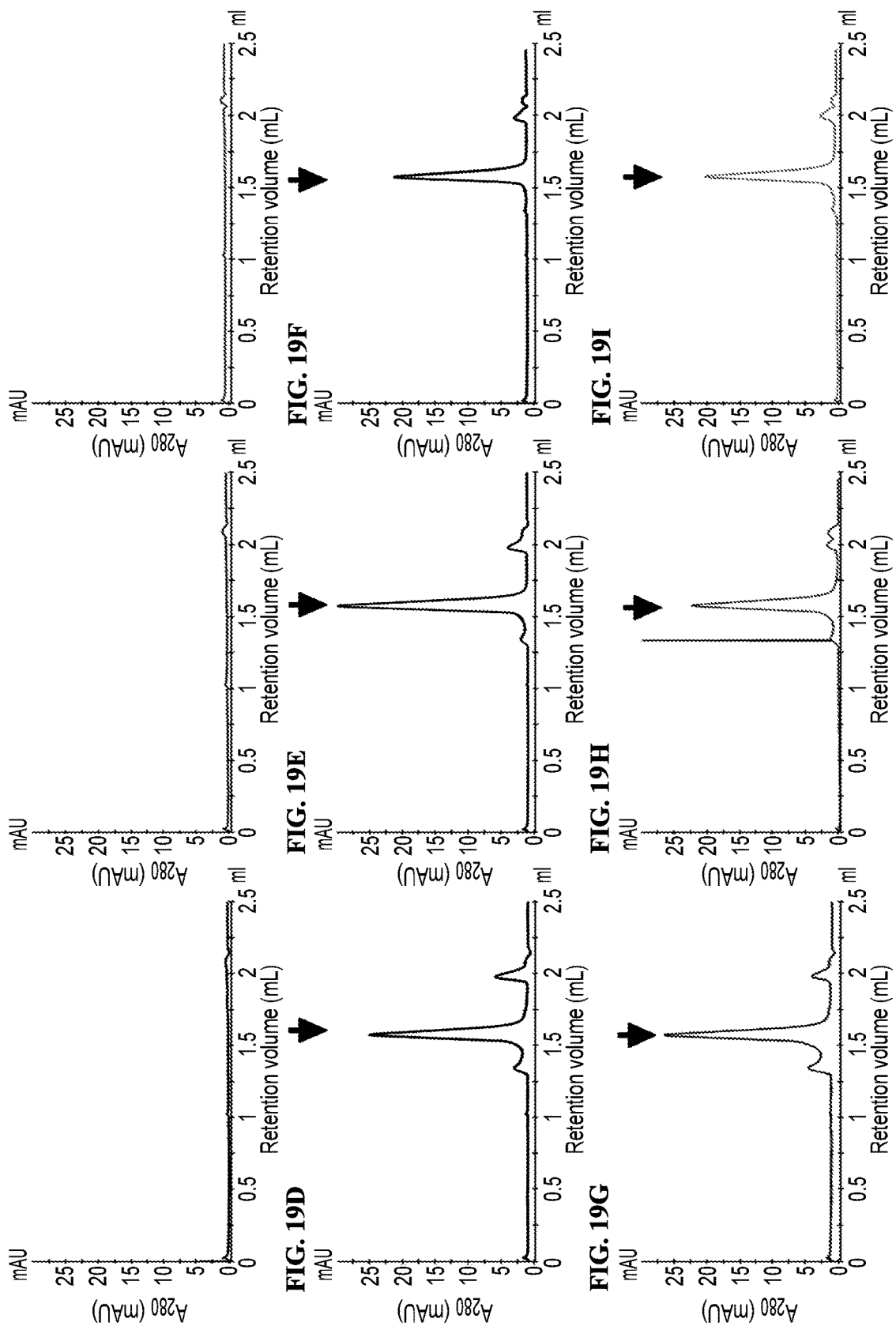

FIG. 27A

```
SEQ_ID_NO:7    MLEGEESVVYVGKKGVIASLIVETLDQSYYDETELKSYVDAEVEDYTAEHGKNAVKVESL    60
SEQ_ID_NO:11   MLEGEESVVYVGKKGVIASLIVETLDQSYYDETELKSYVDAEVEDYTAEHGKNAVKVESL    60
SEQ_ID_NO:13   MLEGEESVVYVGKKGVIASLIVETLDQSYYDETELKSYVDAEVEDYTAEHGKNAVKVESL    60
SEQ_ID_NO:15   MLEGEESVVYVGKKGVIASLIVETLDQSYYDETELKSYVDAEVEDYTAEHGKNAVKVESL    60
SEQ_ID_NO:17   MLEGEESVVYVGKKGVIASLIVETLDQSYYDETELKSYVDAEVEDYTAEHGKNAVKVESL    60
SEQ_ID_NO:19   MLEGEESVVYVGKKGVIASLIVETLDQSYYDETELKSYVDAEVEDYTAEHGKNAVKVESL    60
               ************************************************************

SEQ_ID_NO:7    KVEDGVAKLKKYKTPEDYTAFNGIELYQGKVVASLAAGYVYDGEFARVEEGKVVGAATK   120
SEQ_ID_NO:11   KVEDGVAKLKKYKTPEDYTAFNGIELYQGKVVASLAAGYVYDGEFARVEEGKVVGAATK   120
SEQ_ID_NO:13   KVEDGVAKLKKYKTPEDYTAFNGIELYQGKVVASLAAGYVYDGEFARVEEGKVVGAATK   120
SEQ_ID_NO:15   KVEDGVAKLKKYKTPEDYTAFNGIELYQGKVVASLAAGYVYDGEFARVEEGKVVGAATK   120
SEQ_ID_NO:17   KVEDGVAKLKKYKTPEDYTAFNGIELYQGKVVASLAAGYVYDGEFARVEEGKVVGAATK   120
SEQ_ID_NO:19   KVEDGVAKLKKYKTPEDYTAFNGIELYQGKVVASLAAGYVYDGEFARVEEGKVVGAATK   120
               ************************************************************

SEQ_ID_NO:7    QDIYSEDDLKVAIIRANTDVKVDGEICYVSCQNVKLTGKDSVSIRDGYYLETGSVTASVD   180
SEQ_ID_NO:11   QDIYSEDDLKVAIIRANTDVKVDGEICYVSCQNVKLTGKDSVSIRDGYYLETGSVTASVD   180
SEQ_ID_NO:13   QDIYSEDDLKVAIIRANTDVKVDGEICYVSCQNVKLTGKDSVSIRDGYYLETGSVTASVD   180
SEQ_ID_NO:15   QDIYSEDDLKVAIIRANTDVKVDGEICYVSCQNVKLTGKDSVSIRDGYYLETGSVTASVD   180
SEQ_ID_NO:17   QDIYSEDDLKVAIIRANTDVKVDGEICYVSCQNVKLTGKDSVSIRDGYYLETGSVTASVD   180
SEQ_ID_NO:19   QDIYSEDDLKVAIIRANTDVKVDGEICYVSCQNVKLTGKDSVSIRDGYYLETGSVTASVD   180
               ************************************************************

SEQ_ID_NO:7    VTGQESVGTEQLSGTEQMEMTGEPVNADDTEQTEAAAGDGSFETDVYTFIVYK         233
SEQ_ID_NO:11   VTGQESVGTEQLSGTEQMEMTGEPVNADDTEQTEAAAGDGSFETDVYTFIVYK         233
SEQ_ID_NO:13   VTGQESVGTEQLSGTEQMEMTGEPVNADDTEQTEAAAGDGSFETDVYTFIVYK         233
SEQ_ID_NO:15   VTGQESVGTEQLSGTEQMEMTGEPVNADDTEQTEAAAGDGSFETDVYTFIVYK         233
SEQ_ID_NO:17   VTGQESVGTEQLSGTEQMEMTGEPVNADDTEQTEAAAGDGSFETDVYTFIVYK         233
SEQ_ID_NO:19   VTGQESVGTEQLSGTEQMEMTGEPVNADDTEQTEAAAGDGSFETDVYTFIVYK         233
               *****************************************************
```

FIG. 27B

|   | | SEQ ID NO:7 | SEQ ID NO:11 | SEQ ID NO:13 | SEQ ID NO:15 | SEQ ID NO:17 | SEQ ID NO:19 |
|---|---|---|---|---|---|---|---|
| 1: | SEQ_ID_NO_7  | 100.00 | 99.14  | 98.71  | 98.71  | 98.28  | 98.28  |
| 2: | SEQ_ID_NO_11 | 99.14  | 100.00 | 99.57  | 99.57  | 99.14  | 99.14  |
| 3: | SEQ_ID_NO_13 | 98.71  | 99.57  | 100.00 | 99.14  | 99.57  | 98.71  |
| 4: | SEQ_ID_NO_15 | 98.71  | 99.57  | 99.14  | 100.00 | 98.71  | 99.57  |
| 5: | SEQ_ID_NO_17 | 98.28  | 99.14  | 99.57  | 98.71  | 100.00 | 99.14  |
| 6: | SEQ_ID_NO_19 | 98.28  | 99.14  | 98.71  | 99.57  | 99.14  | 100.00 |

SEQUENCE LISTING

```
<160> NUMBER OF SEQ ID NOS: 34

<210> SEQ ID NO 1
<211> LENGTH: 256
<212> TYPE: PRT
<213> ORGANISM: Roseburia hominis

<400> SEQUENCE: 1

Met Lys Arg Leu Val Cys Thr Val Cys Ser Val Leu Leu Cys Ala Gly
1               5                   10                  15

Leu Leu Ser Gly Cys Gly Thr Ser Leu Glu Gly Glu Glu Ser Val Val
            20                  25                  30

Tyr Val Gly Lys Lys Gly Val Ile Ala Ser Leu Asp Val Glu Thr Leu
        35                  40                  45

Asp Gln Ser Tyr Tyr Asp Glu Thr Glu Leu Lys Ser Tyr Val Asp Ala
    50                  55                  60

Glu Val Glu Asp Tyr Thr Ala Glu His Gly Lys Asn Ala Val Lys Val
65                  70                  75                  80

Glu Ser Leu Lys Val Glu Asp Gly Val Ala Lys Leu Lys Met Lys Tyr
                85                  90                  95

Lys Thr Pro Glu Asp Tyr Thr Ala Phe Asn Gly Ile Glu Leu Tyr Gln
            100                 105                 110

Gly Lys Val Val Ala Ser Leu Ala Ala Gly Tyr Val Tyr Asp Gly Glu
        115                 120                 125

Phe Ala Arg Val Glu Glu Gly Lys Val Val Gly Ala Ala Thr Lys Gln
    130                 135                 140

Asp Ile Tyr Ser Glu Asp Asp Leu Lys Val Ala Ile Ile Arg Ala Asn
145                 150                 155                 160

Thr Asp Val Lys Val Asp Gly Glu Ile Cys Tyr Val Ser Cys Gln Asn
                165                 170                 175

Val Lys Leu Thr Gly Lys Asp Ser Val Ser Ile Arg Asp Gly Tyr Tyr
            180                 185                 190

Leu Glu Thr Gly Ser Val Thr Ala Ser Val Asp Val Thr Gly Gln Glu
        195                 200                 205

Ser Val Gly Thr Glu Gln Leu Ser Gly Thr Glu Gln Met Glu Met Thr
    210                 215                 220

Gly Glu Pro Val Asn Ala Asp Asp Thr Glu Gln Thr Glu Ala Ala Ala
225                 230                 235                 240

Gly Asp Gly Ser Phe Glu Thr Asp Val Tyr Thr Phe Ile Val Tyr Lys
                245                 250                 255

<210> SEQ ID NO 2
<211> LENGTH: 768
<212> TYPE: DNA
<213> ORGANISM: Roseburia hominis

<400> SEQUENCE: 2
atgaagagat tagtgtgcac ggtctgcagt gtactgttgt gtgcgggact tctctccgga      60
tgcggtacct cgctggaggg agaggaaagt gtcgtgtacg tgggaaagaa aggcgtgata     120
```

-continued

```
gcgtcgctgg atgtggagac gctcgatcag tcctactacg atgagacgga actgaagtcc    180
tatgtggatg cagaggtgga agattacacc gcggagcatg gtaaaaatgc agtcaaggtg    240
gagagcctta aggtggaaga cggtgtggcg aagcttaaga tgaagtacaa gacaccggag    300
gattataccg catttaatgg aattgaactc tatcagggga agtcgttgc ttccctggcg     360 gcaggatacg tctacgacgg ggagttcgcc cgcgtggagg aaggcaaggt tgtgggagct    420
gccacaaaac aggatattta ctctgaggat gatttgaaag ttgccatcat ccgtgccaat    480
acggatgtga aggtggacgg tgagatctgc tatgtctcct gtcagaatgt gaagctgacc    540
ggaaaagaca gtgtgtcgat ccgtgacgga tattatcttg agacgggaag cgtgacggca    600
tccgtggatg tgaccggaca ggagagcgtc gggaccgagc agctttcggg aaccgaacag    660
atggagatga ccggggagcc ggtgaatgcg gatgataccg agcagacaga ggcggcggcc    720
ggtgacggtt cgttcgagac agacgtatat actttcattg tctacaaa                768
```

<210> SEQ ID NO 3
<211> LENGTH: 232
<212> TYPE: PRT
<213> ORGANISM: Roseburia hominis

<400> SEQUENCE: 3

```
Leu Glu Gly Glu Glu Ser Val Val Tyr Val Gly Lys Lys Gly Val Ile
1               5                   10                  15

Ala Ser Leu Asp Val Glu Thr Leu Asp Gln Ser Tyr Tyr Asp Glu Thr
                20                  25                  30

Glu Leu Lys Ser Tyr Val Asp Ala Glu Val Glu Asp Tyr Thr Ala Glu
            35                  40                  45

His Gly Lys Asn Ala Val Lys Val Glu Ser Leu Lys Val Glu Asp Gly
        50                  55                  60

Val Ala Lys Leu Lys Met Lys Tyr Lys Thr Pro Glu Asp Tyr Thr Ala
65                  70                  75                  80

Phe Asn Gly Ile Glu Leu Tyr Gln Gly Lys Val Val Ala Ser Leu Ala
                85                  90                  95

Ala Gly Tyr Val Tyr Asp Gly Glu Phe Ala Arg Val Glu Glu Gly Lys
            100                 105                 110

Val Val Gly Ala Ala Thr Lys Gln Asp Ile Tyr Ser Glu Asp Asp Leu
        115                 120                 125

Lys Val Ala Ile Ile Arg Ala Asn Thr Asp Val Lys Val Asp Gly Glu
    130                 135                 140

Ile Cys Tyr Val Ser Cys Gln Asn Val Lys Leu Thr Gly Lys Asp Ser
145                 150                 155                 160

Val Ser Ile Arg Asp Gly Tyr Tyr Leu Glu Thr Gly Ser Val Thr Ala
                165                 170                 175

Ser Val Asp Val Thr Gly Gln Glu Ser Val Gly Thr Glu Gln Leu Ser
            180                 185                 190

Gly Thr Glu Gln Met Glu Met Thr Gly Glu Pro Val Asn Ala Asp Asp
        195                 200                 205

Thr Glu Gln Thr Glu Ala Ala Ala Gly Asp Gly Ser Phe Glu Thr Asp
    210                 215                 220

Val Tyr Thr Phe Ile Val Tyr Lys
225                 230
```

<210> SEQ ID NO 4
<211> LENGTH: 696
<212> TYPE: DNA

<213> ORGANISM: Roseburia hominis

<400> SEQUENCE: 4

```
ctggagggag aggaaagtgt cgtgtacgtg ggaaagaaag gcgtgatagc gtcgctggat    60
gtggagacgc tcgatcagtc ctactacgat gagacggaac tgaagtccta tgtggatgca   120
gaggtggaag attacaccgc ggagcatggt aaaaatgcag tcaaggtgga gagccttaag   180
gtggaagacg gtgtggcgaa gcttaagatg aagtacaaga caccggagga ttataccgca   240
tttaatggaa ttgaactcta tcaggggaaa gtcgttgctt ccctggcggc aggatacgtc   300
tacgacgggg agttcgcccg cgtggaggaa ggcaaggttg tgggagctgc cacaaaacag   360
gatatttact ctgaggatga tttgaaagtt gccatcatcc gtgccaatac ggatgtgaag   420
gtggacggtg agatctgcta tgtctcctgt cagaatgtga agctgaccgg aaaagacagt   480
gtgtcgatcc gtgacggata ttatcttgag acgggaagcg tgacggcatc cgtggatgtg   540
accggacagg agagcgtcgg gaccgagcag ctttcgggaa ccgaacagat ggagatgacc   600
ggggagccgg tgaatgcgga tgataccgag cagacagagg cggcggccgg tgacggttcg   660
ttcgagacag acgtatatac tttcattgtc tacaaa                             696
```

<210> SEQ ID NO 5
<211> LENGTH: 241
<212> TYPE: PRT
<213> ORGANISM: Artificial Sequence
<220> FEATURE:
<223> OTHER INFORMATION: SG11 expressed in pGEX6 vector and cleaved by Precision protease

<400> SEQUENCE: 5

```
Gly Pro Leu Gly Ser Leu Glu Gly Glu Glu Ser Val Val Tyr Val Gly
 1               5                  10                  15

Lys Lys Gly Val Ile Ala Ser Leu Asp Val Glu Thr Leu Asp Gln Ser
            20                  25                  30

Tyr Tyr Asp Glu Thr Glu Leu Lys Ser Tyr Val Asp Ala Glu Val Glu
        35                  40                  45

Asp Tyr Thr Ala Glu His Gly Lys Asn Ala Val Lys Val Glu Ser Leu
    50                  55                  60

Lys Val Glu Asp Gly Val Ala Lys Leu Lys Met Lys Tyr Lys Thr Pro
65                  70                  75                  80

Glu Asp Tyr Thr Ala Phe Asn Gly Ile Glu Leu Tyr Gln Gly Lys Val
                85                  90                  95

Val Ala Ser Leu Ala Ala Gly Tyr Val Tyr Asp Gly Glu Phe Ala Arg
            100                 105                 110

Val Glu Glu Gly Lys Val Val Gly Ala Ala Thr Lys Gln Asp Ile Tyr
        115                 120                 125

Ser Glu Asp Asp Leu Lys Val Ala Ile Ile Arg Ala Asn Thr Asp Val
    130                 135                 140

Lys Val Asp Gly Glu Ile Cys Tyr Val Ser Cys Gln Asn Val Lys Leu
145                 150                 155                 160

Thr Gly Lys Asp Ser Val Ser Ile Arg Asp Gly Tyr Tyr Leu Glu Thr
                165                 170                 175

Gly Ser Val Thr Ala Ser Val Asp Thr Gly Gln Glu Ser Val Gly
            180                 185                 190

Thr Glu Gln Leu Ser Gly Thr Glu Gln Met Glu Met Thr Gly Glu Pro
        195                 200                 205

Val Asn Ala Asp Asp Thr Glu Gln Thr Glu Ala Ala Ala Gly Asp Gly
```

210                 215                 220
Ser Phe Glu Thr Asp Val Tyr Thr Phe Ile Val Tyr Lys Ala Ala Ala
225                 230                 235                 240

Ser

<210> SEQ ID NO 6
<211> LENGTH: 723
<212> TYPE: DNA
<213> ORGANISM: Artificial Sequence
<220> FEATURE:
<223> OTHER INFORMATION: SG11 expressed in pGEX6 vector and cleaved by
      Precision protease

<400> SEQUENCE: 6
gggcccctgg gatccctgga gggagaggaa agtgtcgtgt acgtgggaaa gaaaggcgtg    60
atagcgtcgc tggatgtgga gacgctcgat cagtcctact acgatgagac ggaactgaag   120
tcctatgtgg atgcagaggt ggaagattac accgcggagc atggtaaaaa tgcagtcaag   180
gtggagagcc ttaaggtgga agacggtgtg gcgaagctta agatgaagta caagacaccg   240
gaggattata ccgcatttaa tggaattgaa ctctatcagg ggaaagtcgt tgcttccctg   300
gcggcaggat acgtctacga cggggagttc gcccgcgtgg aggaaggcaa ggttgtggga   360
gctgccacaa acaggatat ttactctgag gatgatttga agttgccat catccgtgcc    420 aatacggatg tgaaggtgga cggtgagatc tgctatgtct cctgtcagaa tgtgaagctg   480
accggaaaag acagtgtgtc gatccgtgac ggatattatc ttgagacggg aagcgtgacg   540
gcatccgtgg atgtgaccgg acaggagagc gtcgggaccg agcagctttc gggaaccgaa   600
cagatggaga tgaccgggga gccggtgaat gcggatgata ccgagcagac agaggcggcg   660
gccggtgacg gttcgttcga gacagacgta tatactttca ttgtctacaa agcggccgca   720
tcg                                                                723

<210> SEQ ID NO 7
<211> LENGTH: 233
<212> TYPE: PRT
<213> ORGANISM: Artificial Sequence
<220> FEATURE:
<223> OTHER INFORMATION: SG11 with start methionine

<400> SEQUENCE: 7

Met Leu Glu Gly Glu Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
            20                  25                  30

Thr Glu Leu Lys Ser Tyr Val Asp Ala Glu Val Glu Asp Tyr Thr Ala
        35                  40                  45

Glu His Gly Lys Asn Ala Val Lys Val Glu Ser Leu Lys Val Glu Asp
    50                  55                  60

Gly Val Ala Lys Leu Lys Met Lys Tyr Lys Thr Pro Glu Asp Tyr Thr
65                  70                  75                  80

Ala Phe Asn Gly Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly

Glu Ile Cys Tyr Val Ser Cys Gln Asn Val Lys Leu Thr Gly Lys Asp
145                 150                 155                 160

Ser Val Ser Ile Arg Asp Gly Tyr Tyr Leu Glu Thr Gly Ser Val Thr
                165                 170                 175

Ala Ser Val Asp Val Thr Gly Gln Glu Ser Val Gly Thr Glu Gln Leu
            180                 185                 190

Ser Gly Thr Glu Gln Met Glu Met Thr Gly Glu Pro Val Asn Ala Asp
        195                 200                 205

Asp Thr Glu Gln Thr Glu Ala Ala Ala Gly Asp Gly Ser Phe Glu Thr
    210                 215                 220

Asp Val Tyr Thr Phe Ile Val Tyr Lys
225                 230

<210> SEQ ID NO 8
<211> LENGTH: 699
<212> TYPE: DNA
<213> ORGANISM: Artificial Sequence
<220> FEATURE:
<223> OTHER INFORMATION: SG11 with start methionine

<400> SEQUENCE: 8
atgttggagg gtgaagagtc tgttgtctat gtgggtaaga aggtgtgat cgcgtccctg     60
gacgtcgaga ctctggacca gtcttactat gatgaaaccg agctgaagtc gtatgtggac   120
gccgaagttg aggattacac ggccgagcac ggcaaaaatg ccgtcaaagt tgagagcttg   180
aaagttgagg acggcgtggc aaagctgaag atgaaataca gaccccaga ggactacacg    240
gcgttcaatg gtatcgagct gtatcagggc aaagtcgtcg catccctggc agcgggctat   300
gtgtacgacg tgagtttgc gcgcgtcgaa gaaggcaaaa ttgtgggtgc ggctacgaaa   360
caagatatct acagcgaaga tgacctgaaa gtcgcgatta ttcgtgctaa caccgatgtt   420
aaagttgatg gcgagatttg ctacgttagc tgtcaaaacg taaagctgac gggtaaagat   480
agcgtgagca ttcgtgatgg ctattatctg gaaaccggta gcgttacggc gagcgtcgat   540
gttaccggtc aagagagcgt gggtaccgaa cagctgagcg gcaccgaaca gatggaaatg   600
accggtgaac cggttaacgc agacgacacg gaacaaaccg aagccgcggc aggcgacggt   660
agcttcgaga ctgacgtgta cacctttatc gtgtacaag                         699

<210> SEQ ID NO 9
<211> LENGTH: 246
<212> TYPE: PRT
<213> ORGANISM: Artificial Sequence
<220> FEATURE:
<223> OTHER INFORMATION: SG11 with N-terminal FLAG tag

<400> SEQUENCE: 9

Met Asp Tyr Lys Asp Asp Asp Lys Gly Ser Ser His Met Leu Glu
1               5                   10                  15

Gly Glu Glu Ser Val Val Tyr Val Gly Lys Lys Gly Val Ile Ala Ser
            20                  25                  30

Leu Asp Val Glu Thr Leu Asp Gln Ser Tyr Tyr Asp Glu Thr Glu Leu
        35                  40                  45

Lys Ser Tyr Val Asp Ala Glu Val Glu Asp Tyr Thr Ala Glu His Gly
    50                  55                  60

Lys Asn Ala Val Lys Val Glu Ser Leu Lys Val Glu Asp Gly Val Ala
65                  70                  75                  80

```
Lys Leu Lys Met Lys Tyr Lys Thr Pro Glu Asp Tyr Thr Ala Phe Asn
                 85                  90                  95

Gly Ile Glu Leu Tyr Gln Gly Lys Val Val Ala Ser Leu Ala Ala Gly
            100                 105                 110

Tyr Val Tyr Asp Gly Glu Phe Ala Arg Val Glu Glu Gly Lys Val Val
        115                 120                 125

Gly Ala Ala Thr Lys Gln Asp Ile Tyr Ser Glu Asp Leu Lys Val
    130                 135                 140

Ala Ile Ile Arg Ala Asn Thr Asp Val Lys Val Asp Gly Glu Ile Cys
145                 150                 155                 160

Tyr Val Ser Cys Gln Asn Val Lys Leu Thr Gly Lys Asp Ser Val Ser
                165                 170                 175

Ile Arg Asp Gly Tyr Tyr Leu Glu Thr Gly Ser Val Thr Ala Ser Val
            180                 185                 190

Asp Val Thr Gly Gln Glu Ser Val Gly Thr Glu Gln Leu Ser Gly Thr
        195                 200                 205

Glu Gln Met Glu Met Thr Gly Glu Pro Val Asn Ala Asp Asp Thr Glu
    210                 215                 220

Gln Thr Glu Ala Ala Ala Gly Asp Gly Ser Phe Glu Thr Asp Val Tyr
225                 230                 235                 240

Thr Phe Ile Val Tyr Lys
                245

<210> SEQ ID NO 10
<211> LENGTH: 738
<212> TYPE: DNA
<213> ORGANISM: Artificial Sequence
<220> FEATURE:
<223> OTHER INFORMATION: SG11 with N-terminal FLAG tag (not codon
      optimized)

<400> SEQUENCE: 10
atggactaca aagacgatga cgacaagggc agcagccata tgctggaggg agaggaaagt      60
gtcgtgtacg tgggaaagaa aggcgtgata gcgtcgctgg atgtggagac gctcgatcag     120
tcctactacg atgagacgga actgaagtcc tatgtggatg cagaggtgga agattacacc     180
gcggagcatg gtaaaaatgc agtcaaggtg gagagcctta aggtggaaga cggtgtggcg     240
aagcttaaga tgaagtacaa gacaccggag gattataccg catttaatgg aattgaactc     300
tatcagggga aagtcgttgc ttccctggcg gcaggatacg tctacgacgg ggagttcgcc     360
cgcgtggagg aaggcaaggt tgtgggagct gccacaaaac aggatattta ctctgaggat     420
gatttgaaag ttgccatcat ccgtgccaat acggatgtga aggtggacgg tgagatctgc     480
tatgtctcct gtcagaatgt gaagctgacc ggaaaagaca gtgtgtcgat ccgtgacgga     540
tattatcttg agacgggaag cgtgacggca tccgtggatg tgaccggaca ggagagcgtc     600
gggaccgagc agctttcggg aaccgaacag atggagatga ccggggagcc ggtgaatgcg     660
gatgataccg agcagacaga ggcggcggcc ggtgacggtt cgttcgagac agacgtatat     720
actttcattg tctacaaa                                                   738

<210> SEQ ID NO 11
<211> LENGTH: 233
<212> TYPE: PRT
<213> ORGANISM: Artificial Sequence
<220> FEATURE:
<223> OTHER INFORMATION: Artificial variant of SG11  (C147V, C151S)

<400> SEQUENCE: 11
```

Met Leu Glu Gly Glu Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
            20                  25                  30

Thr Glu Leu Lys Ser Tyr Val Asp Ala Glu Val Glu Asp Tyr Thr Ala
        35                  40                  45

Glu His Gly Lys Asn Ala Val Lys Val Glu Ser Leu Lys Val Glu Asp
    50                  55                  60

Gly Val Ala Lys Leu Lys Met Lys Tyr Lys Thr Pro Glu Asp Tyr Thr
65                  70                  75                  80

Ala Phe Asn Gly Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly
    130                 135                 140

Glu Ile Val Tyr Val Ser Ser Gln Asn Val Lys Leu Thr Gly Lys Asp
145                 150                 155                 160

Ser Val Ser Ile Arg Asp Gly Tyr Tyr Leu Glu Thr Gly Ser Val Thr
                165                 170                 175

Ala Ser Val Asp Val Thr Gly Gln Glu Ser Val Gly Thr Glu Gln Leu
            180                 185                 190

Ser Gly Thr Glu Gln Met Glu Met Thr Gly Glu Pro Val Asn Ala Asp
        195                 200                 205

Asp Thr Glu Gln Thr Glu Ala Ala Ala Gly Asp Gly Ser Phe Glu Thr
    210                 215                 220

Asp Val Tyr Thr Phe Ile Val Tyr Lys
225                 230

<210> SEQ ID NO 12
<211> LENGTH: 699
<212> TYPE: DNA
<213> ORGANISM: Artificial Sequence
<220> FEATURE:
<223> OTHER INFORMATION: Artificial variant of SG11   (C147V, C151S)
      (codon optimized)

<400> SEQUENCE: 12
atgttggagg gtgaagagtc tgttgtctat gtgggtaaga aaggtgtgat cgcgtccctg      60
gacgtcgaga ctctggacca gtcttactat gatgaaaccg agctgaagtc gtatgtggac     120
gccgaagttg aggattacac ggccgagcac ggcaaaaatg ccgtcaaagt tgagagcttg     180
aaagttgagg acggcgtggc aaagctgaag atgaaataca gaccccagag gactacacg     240 gcgttcaatg gtatcgagct gtatcagggc aaagtcgtcg catccctggc agcgggctat     300
gtgtacgacg gtgagtttgc gcgcgtcgaa gaaggcaaag ttgtgggtgc ggctacgaaa     360
caagatatct acagcgaaga tgacctgaaa gtcgcgatta ttcgtgctaa caccgatgtt     420
aaagttgatg gcgagattgt gtacgttagc agccaaaacg taaagctgac gggtaaagat     480
agcgtgagca ttcgtgatgg ctattatctg gaaaccggta gcgttacggc gagcgtcgat     540
gttaccggtc aagagagcgt gggtaccgaa cagctgagcg gcaccgaaca gatggaaatg     600
accggtgaac cggttaacgc agacgacacg gaacaaaccg aagccgcggc aggcgacggt     660
agcttcgaga ctgacgtgta caccttatc gtgtacaag　　　　　　　　　　　　　　699

<210> SEQ ID NO 13
<211> LENGTH: 233
<212> TYPE: PRT
<213> ORGANISM: Artificial Sequence
<220> FEATURE:
<223> OTHER INFORMATION: Artificial variant of SG11 (G84D, C147V, C151S)

<400> SEQUENCE: 13

```
Met Leu Glu Gly Glu Glu Ser Val Val Tyr Val Gly Lys Lys Gly Val
1               5                   10                  15
Ile Ala Ser Leu Asp Val Glu Thr Leu Asp Gln Ser Tyr Tyr Asp Glu
                20                  25                  30
Thr Glu Leu Lys Ser Tyr Val Asp Ala Glu Val Glu Asp Tyr Thr Ala
            35                  40                  45
Glu His Gly Lys Asn Ala Val Lys Val Glu Ser Leu Lys Val Glu Asp
        50                  55                  60
Gly Val Ala Lys Leu Lys Met Lys Tyr Lys Thr Pro Glu Asp Tyr Thr
65                  70                  75                  80
Ala Phe Asn Asp Ile Glu Leu Tyr Gln Gly Lys Val Val Ala Ser Leu
                85                  90                  95
Ala Ala Gly Tyr Val Tyr Asp Gly Glu Phe Ala Arg Val Glu Glu Gly
            100                 105                 110
Lys Val Val Gly Ala Ala Thr Lys Gln Asp Ile Tyr Ser Glu Asp Asp
        115                 120                 125
Leu Lys Val Ala Ile Ile Arg Ala Asn Thr Asp Val Lys Val Asp Gly
    130                 135                 140
Glu Ile Val Tyr Val Ser Ser Gln Asn Val Lys Leu Thr Gly Lys Asp
145                 150                 155                 160
Ser Val Ser Ile Arg Asp Gly Tyr Tyr Leu Glu Thr Gly Ser Val Thr
                165                 170                 175
Ala Ser Val Asp Val Thr Gly Gln Glu Ser Val Gly Thr Glu Gln Leu
            180                 185                 190
Ser Gly Thr Glu Gln Met Glu Met Thr Gly Glu Pro Val Asn Ala Asp
        195                 200                 205
Asp Thr Glu Gln Thr Glu Ala Ala Ala Gly Asp Gly Ser Phe Glu Thr
    210                 215                 220
Asp Val Tyr Thr Phe Ile Val Tyr Lys
225                 230
```

<210> SEQ ID NO 14
<211> LENGTH: 699
<212> TYPE: DNA
<213> ORGANISM: Artificial Sequence
<220> FEATURE:
<223> OTHER INFORMATION: Artificial variant of SG11 (G84D, C147V, C151S) (codon optimized)

<400> SEQUENCE: 14
atgttggagg gtgaagagtc tgttgtctat gtgggtaaga aggtgtgat cgcgtccctg　　60 gacgtcgaga ctctggacca gtcttactat gatgaaaccg agctgaagtc gtatgtggac　120 gccgaagttg aggattacac ggccgagcac ggcaaaaatg ccgtcaaagt tgagagcttg　180 aaagttgagg acggcgtggc aaagctgaag atgaaataca agaccccaga ggactacacg　240 gcgttcaatg acatcgagct gtatcagggc aaagtcgtcg catccctggc agcgggctat　300

```
gtgtacgacg gtgagtttgc gcgcgtcgaa gaaggcaaag ttgtgggtgc ggctacgaaa    360
caagatatct acagcgaaga tgacctgaaa gtcgcgatta ttcgtgctaa caccgatgtt    420
aaagttgatg gcgagattgt gtacgttagc agccaaaacg taaagctgac gggtaaagat    480
agcgtgagca ttcgtgatgg ctattatctg gaaaccggta gcgttacggg gagcgtcgat    540
gttaccggtc aagagagcgt gggtaccgaa cagctgagcg gcaccgaaca gatggaaatg    600
accggtgaac cggttaacgc agacgacacg gaacaaaccg aagccgcggc aggcgacggt    660
agcttcgaga ctgacgtgta cacctttatc gtgtacaag                           699
```

<210> SEQ ID NO 15
<211> LENGTH: 233
<212> TYPE: PRT
<213> ORGANISM: Artificial Sequence
<220> FEATURE:
<223> OTHER INFORMATION: Artificial variant of SG11 (N83S, C147V, C151S)

<400> SEQUENCE: 15

```
Met Leu Glu Gly Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
                20                  25                  30

Thr Glu Leu Lys Ser Tyr Val Asp Ala Glu Val Glu Asp Tyr Thr Ala
            35                  40                  45

Glu His Gly Lys Asn Ala Val Lys Val Glu Ser Leu Lys Val Glu Asp
        50                  55                  60

Gly Val Ala Lys Leu Lys Met Lys Tyr Lys Thr Pro Glu Asp Tyr Thr
65                  70                  75                  80

Ala Phe Ser Gly Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly
    130                 135                 140

Glu Ile Val Tyr Val Ser Ser Gln Asn Val Lys Leu Thr Gly Lys Asp
145                 150                 155                 160

Ser Val Ser Ile Arg Asp Gly Tyr Tyr Leu Glu Thr Gly Ser Val Thr
                165                 170                 175

Ala Ser Val Asp Val Thr Gly Gln Glu Ser Val Gly Thr Glu Gln Leu
            180                 185                 190

Ser Gly Thr Glu Gln Met Glu Met Thr Gly Glu Pro Val Asn Ala Asp
        195                 200                 205

Asp Thr Glu Gln Thr Glu Ala Ala Ala Gly Asp Gly Ser Phe Glu Thr
    210                 215                 220

Asp Val Tyr Thr Phe Ile Val Tyr Lys
225                 230
```

<210> SEQ ID NO 16
<211> LENGTH: 699
<212> TYPE: DNA
<213> ORGANISM: Artificial Sequence
<220> FEATURE:
<223> OTHER INFORMATION: Artificial variant of SG11 (N83S, C147V, C151S) (codon optimized)

<400> SEQUENCE: 16

```
atgttggagg gtgaagagtc tgttgtctat gtgggtaaga aaggtgtgat cgcgtccctg    60
gacgtcgaga ctctggacca gtcttactat gatgaaaccg agctgaagtc gtatgtggac   120
gccgaagttg aggattacac ggccgagcac ggcaaaaatg ccgtcaaagt tgagagcttg   180
aaagttgagg acggcgtggc aaagctgaag atgaaataca agaccccaga ggactacacg   240
gcgttcagcg gtatcgagct gtatcagggc aaagtcgtcg catccctggc agcgggctat   300
gtgtacgacg gtgagtttgc gcgcgtcgaa gaaggcaaag ttgtgggtgc ggctacgaaa   360
caagatatct acagcgaaga tgacctgaaa gtcgcgatta ttcgtgctaa caccgatgtt   420
aaagttgatg gcgagattgt gtacgttagc agccaaaacg taaagctgac gggtaaagat   480
agcgtgagca ttcgtgatgg ctattatctg gaaaccggta gcgttacggc gagcgtcgat   540
gttaccggtc aagagagcgt gggtaccgaa cagctgagcg gcaccgaaca gatggaaatg   600
accggtgaac cggttaacgc agacgacacg gaacaaaccg aagccgcggc aggcgacggt   660
agcttcgaga ctgacgtgta caccttatcg gtgtacaag              699
```

<210> SEQ ID NO 17
<211> LENGTH: 233
<212> TYPE: PRT
<213> ORGANISM: Artificial Sequence
<220> FEATURE:
<223> OTHER INFORMATION: Artificial variant of SG11 (N53S, G84D, C147V, C151S)

<400> SEQUENCE: 17

```
Met Leu Glu Gly Glu Glu Ser Val Val Tyr Val Gly Lys Lys Gly Val
1               5                   10                  15
Ile Ala Ser Leu Asp Val Glu Thr Leu Asp Gln Ser Tyr Tyr Asp Glu
            20                  25                  30
Thr Glu Leu Lys Ser Tyr Val Asp Ala Glu Val Glu Asp Tyr Thr Ala
        35                  40                  45
Glu His Gly Lys Ser Ala Val Lys Val Glu Ser Leu Lys Val Glu Asp
    50                  55                  60
Gly Val Ala Lys Leu Lys Met Lys Tyr Lys Thr Pro Glu Asp Tyr Thr
65                  70                  75                  80
Ala Phe Asn Asp Ile Glu Leu Tyr Gln Gly Lys Val Val Ala Ser Leu
                85                  90                  95
Ala Ala Gly Tyr Val Tyr Asp Gly Glu Phe Ala Arg Val Glu Glu Gly
            100                 105                 110
Lys Val Val Gly Ala Ala Thr Lys Gln Asp Ile Tyr Ser Glu Asp Asp
        115                 120                 125
Leu Lys Val Ala Ile Ile Arg Ala Asn Thr Asp Val Lys Val Asp Gly
    130                 135                 140
Glu Ile Val Tyr Val Ser Ser Gln Asn Val Lys Leu Thr Gly Lys Asp
145                 150                 155                 160
Ser Val Ser Ile Arg Asp Gly Tyr Tyr Leu Glu Thr Gly Ser Val Thr
                165                 170                 175
Ala Ser Val Asp Val Thr Gly Gln Glu Ser Val Gly Thr Glu Gln Leu
            180                 185                 190
Ser Gly Thr Glu Gln Met Glu Met Thr Gly Glu Pro Val Asn Ala Asp
        195                 200                 205
Asp Thr Glu Gln Thr Glu Ala Ala Ala Gly Asp Gly Ser Phe Glu Thr
    210                 215                 220
```

Asp Val Tyr Thr Phe Ile Val Tyr Lys
225                 230

<210> SEQ ID NO 18
<211> LENGTH: 699
<212> TYPE: DNA
<213> ORGANISM: Artificial Sequence
<220> FEATURE:
<223> OTHER INFORMATION: Artificial variant of SG11 (N53S, G84D, C147V, C151S) (codon optimized)

<400> SEQUENCE: 18

```
atgttggagg gtgaagagtc tgttgtctat gtgggtaaga aggtgtgat cgcgtccctg     60
gacgtcgaga ctctggacca gtcttactat gatgaaaccg agctgaagtc gtatgtggac   120
gccgaagttg aggattacac ggccgagcac ggcaaatccg ccgtcaaagt tgagagcttg   180
aaagttgagg acggcgtggc aaagctgaag atgaaataca gaccccaga ggactacacg    240
gcgttcaatg acatcgagct gtatcagggc aaagtcgtcg catccctggc agcgggctat   300
gtgtacgacg gtgagtttgc gcgcgtcgaa gaaggcaaag ttgtgggtgc ggctacgaaa   360
caagatatct acagcgaaga tgacctgaaa gtcgcgatta ttcgtgctaa caccgatgtt   420
aaagttgatg gcgagattgt gtacgttagc agccaaaacg taaagctgac gggtaaagat   480
agcgtgagca ttcgtgatgg ctattatctg gaaaccggta gcgttacggc gagcgtcgat   540
gttaccggtc aagagagcgt gggtaccgaa cagctgagcg caccgaaca gatggaaatg    600
accggtgaac cggttaacgc agacgacacg gaacaaaccg aagccgcggc aggcgacggt   660
agcttcgaga ctgacgtgta cacctttatc gtgtacaag                         699
```

<210> SEQ ID NO 19
<211> LENGTH: 233
<212> TYPE: PRT
<213> ORGANISM: Artificial Sequence
<220> FEATURE:
<223> OTHER INFORMATION: Artificial variant of SG11 (N53S, N83S, C147V, C151S)

<400> SEQUENCE: 19

Met Leu Glu Gly Glu Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
            20                  25                  30

Thr Glu Leu Lys Ser Tyr Val Asp Ala Glu Val Glu Asp Tyr Thr Ala
        35                  40                  45

Glu His Gly Lys Ser Ala Val Lys Val Glu Ser Leu Lys Val Glu Asp
    50                  55                  60

Gly Val Ala Lys Leu Lys Met Lys Tyr Lys Thr Pro Glu Asp Tyr Thr
65                  70                  75                  80

Ala Phe Ser Gly Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly
    130                 135                 140

Glu Ile Val Tyr Val Ser Ser Gln Asn Val Lys Leu Thr Gly Lys Asp
145                 150                 155                 160

Ser Val Ser Ile Arg Asp Gly Tyr Tyr Leu Glu Thr Gly Ser Val Thr
            165                 170                 175

Ala Ser Val Asp Val Thr Gly Gln Glu Ser Val Gly Thr Glu Gln Leu
        180                 185                 190

Ser Gly Thr Glu Gln Met Glu Met Thr Gly Glu Pro Val Asn Ala Asp
            195                 200                 205

Asp Thr Glu Gln Thr Glu Ala Ala Ala Gly Asp Gly Ser Phe Glu Thr
        210                 215                 220

Asp Val Tyr Thr Phe Ile Val Tyr Lys
225                 230

<210> SEQ ID NO 20
<211> LENGTH: 699
<212> TYPE: DNA
<213> ORGANISM: Artificial Sequence
<220> FEATURE:
<223> OTHER INFORMATION: Artificial variant of SG11 (N53S, N83S, C147V,
      C151S) (codon optimized)

<400> SEQUENCE: 20
atgttggagg gtgaagagtc tgttgtctat gtgggtaaga aagtgtgat cgcgtccctg      60
gacgtcgaga ctctggacca gtcttactat gatgaaaccg agctgaagtc gtatgtggac    120
gccgaagttg aggattacac ggccgagcac ggcaaatccg ccgtcaaagt tgagagcttg    180
aaagttgagg acggcgtggc aaagctgaag atgaaataca agaccccaga ggactacacg    240
gcgttcagcg gtatcgagct gtatcagggc aaagtcgtcg catccctggc agcgggctat    300
gtgtacgacg tgagtttgc gcgcgtcgaa gaaggcaaag ttgtgggtgc ggctacgaaa    360
caagatatct acagcgaaga tgacctgaaa gtcgcgatta ttcgtgctaa caccgatgtt    420
aaagttgatg cgagagattgt gtacgttagc agccaaaacg taaagctgac gggtaaagat    480
agcgtgagca ttcgtgatgg ctattatctg gaaaccggta gcgttacggc gagcgtcgat    540
gttaccggtc aagagagcgt gggtaccgaa cagctgagcg gcaccgaaca gatggaaatg    600
accggtgaac cggttaacgc agacgacacg gaacaaaccg aagccgcggc aggcgacggt    660
agcttcgaga ctgacgtgta caccttttatc gtgtacaag                         699

<210> SEQ ID NO 21
<211> LENGTH: 227
<212> TYPE: PRT
<213> ORGANISM: Roseburia intestinalis

<400> SEQUENCE: 21

Met Leu Asp Ala Asp Thr Asp Thr Val Tyr Val Gln Lys Asn Gly Thr
1               5                   10                  15

Val Leu Ser Val Asp Val Glu Thr Leu Asp Lys Asp Tyr Tyr Asp Glu
            20                  25                  30

Thr Glu Leu Lys Asp Tyr Val Thr Asp Ala Val Ser Thr Tyr Thr Gly
        35                  40                  45

Glu His Gly Lys Ser Ala Val Lys Leu Glu Asn Leu Ser Val Lys Asp
    50                  55                  60

Gly Thr Ala Thr Leu Lys Met Lys Tyr Lys Thr Pro Glu Asp Tyr Thr
65                  70                  75                  80

Gly Phe Asn Gly Ile Glu Leu Tyr Glu Gly Lys Val Val Lys Ala Leu
            85                  90                  95

Ala Ala Gly Tyr Asp Phe Lys Thr Asp Phe Val Ser Val Glu Asp Gly
        100                 105                 110

```
Lys Val Thr Gly Thr Ala Thr Lys Glu Glu Ile Tyr Ser Gly Glu Asp
            115                 120                 125

Leu Lys Val Val Ile Ile Lys Ala Asn Arg Asp Val Lys Val Asp Gly
        130                 135                 140

Thr Ile Cys Tyr Val Ser Ser Glu Asn Val Lys Leu Thr Gly Thr Asp
145                 150                 155                 160

Ser Val Ser Ile Arg Asp Gly Tyr Ser Leu Asn Ser Gly Ser Thr Ala
                165                 170                 175

Asp Glu Ser Asp Ser Asp Glu Asn Ile Ala Asp Gly Thr Glu Ser Ile
            180                 185                 190

Gly Gly Ser Thr Glu Val Ser Asp Thr Asp Val Asn Asp Asp Thr Thr
        195                 200                 205

Tyr Val Lys Asp Asp Gly Ala Phe Glu Thr Asp Val Tyr Thr Tyr Ile
210                 215                 220

Ile Tyr Lys
225

<210> SEQ ID NO 22
<211> LENGTH: 215
<212> TYPE: PRT
<213> ORGANISM: Roseburia sp. 831b

<400> SEQUENCE: 22

Met Leu Asp Val Glu Glu Ser Thr Val Tyr Val Gln Lys Asn Gly Ser
1               5                   10                  15

Val Ile Ser Thr Asp Ile Glu Asp Phe Ser Ala Asp Tyr Tyr Asp Glu
            20                  25                  30

Asp Glu Leu Lys Asp Tyr Ile Gly Asp Glu Ile Ser Ser Tyr Thr Ser
        35                  40                  45

Glu Asn Gly Lys Lys Ser Val Ser Leu Glu Ser Val Ser Val Lys Asp
    50                  55                  60

Ser Val Ala Lys Leu Thr Met Lys Tyr Lys Thr Ala Glu Asp Tyr Thr
65                  70                  75                  80

Asn Phe Asn Gly Val Glu Leu Tyr Thr Gly Thr Ile Val Lys Ala Met
                85                  90                  95

Ala Ala Gly Tyr Asp Phe Gly Val Asp Phe Val Ser Val Lys Asp Gly
            100                 105                 110

Ala Val Thr Gly Thr Ala Thr Lys Asp Glu Ile Val Asp His Asp Asp
        115                 120                 125

Tyr Lys Val Ala Val Ile Lys Ala Asn Thr Asp Val Lys Val Asp Gly
    130                 135                 140

Thr Ile Val Tyr Val Ser Ser Gln Asn Val Lys Val Thr Gly Lys Asn
145                 150                 155                 160

Thr Val Ser Ile Arg Glu Gly Tyr Leu Ala Ala Asp Thr Thr Asn Val
                165                 170                 175

Val Gly Ser Thr Glu Thr Val Ala Glu Thr Ala Glu Glu Ala Asn
            180                 185                 190

Gln Thr Glu Ala Val Leu Glu Asp Glu Phe Ala Ser Glu Ser Asp Val
        195                 200                 205

Tyr Thr Tyr Val Ile Phe Lys
    210                 215

<210> SEQ ID NO 23
<211> LENGTH: 236
<212> TYPE: PRT
<213> ORGANISM: Roseburia inulinivorans
```

<400> SEQUENCE: 23

```
Met Leu Glu Ala Asp Thr Asn Thr Val Tyr Val Ser Lys His Gly Lys
1               5                   10                  15

Val Val Ser Met Asp Val Glu Gln Leu Asp Gln Ser Tyr Tyr Asp Glu
            20                  25                  30

Thr Glu Leu Lys Glu Phe Val Asp Ser Ala Val Asp Glu Tyr Asn Thr
        35                  40                  45

Glu Asn Gly Lys Asn Ser Val Lys Val Asp Asp Leu Thr Val Glu Asp
50                  55                  60

Gly Thr Ala Lys Leu Arg Met Asp Tyr Glu Thr Val Asp Asp Tyr Thr
65                  70                  75                  80

Ala Phe Asn Gly Val Glu Leu Tyr Gly Gly Lys Ile Val Gln Ala Leu
                85                  90                  95

Ala Ala Gly Tyr Asp Phe Asp Thr Asp Phe Ala Gly Val Asp Lys Asp
            100                 105                 110

Gly Cys Val Thr Gly Val Thr Arg Gly Asp Ile Leu Ala Gln Glu Asp
        115                 120                 125

Leu Lys Val Val Ile Ile Lys Ala Asn Thr Asp Val Lys Ile Asp Gly
130                 135                 140

Lys Ile Leu Tyr Val Ser Cys Asp Asn Val Thr Val Thr Gly Lys Asp
145                 150                 155                 160

Ser Val Ser Ile Lys Glu Gly Thr Gly Ile Glu Lys Thr Trp Ile Thr
                165                 170                 175

Glu Ala Glu Glu Val Pro Ser Thr Glu Ala Val Leu Glu Thr Glu Ser
            180                 185                 190

Thr Glu Asp Ala Gly Asp Val Ile Glu Gly Glu Val Ile Ile Gly Thr
        195                 200                 205

Glu Glu Ala Ser Gly Asn Asp Val Val Thr Asn Leu Ser Gly Gly Ser
210                 215                 220

Ser Gly Thr Asp Val Tyr Thr Tyr Ile Ile Tyr Lys
225                 230                 235
```

<210> SEQ ID NO 24
<211> LENGTH: 13
<212> TYPE: PRT
<213> ORGANISM: Artificial Sequence
<220> FEATURE:
<223> OTHER INFORMATION: Fragment of SG11 with start methionine

<400> SEQUENCE: 24

```
Met Leu Glu Gly Glu Glu Ser Val Val Tyr Val Gly Lys
1               5                   10
```

<210> SEQ ID NO 25
<211> LENGTH: 22
<212> TYPE: PRT
<213> ORGANISM: Roseburia hominis

<400> SEQUENCE: 25

```
Gly Val Ile Ala Ser Leu Asp Val Glu Thr Leu Asp Gln Ser Tyr Tyr
1               5                   10                  15

Asp Glu Thr Glu Leu Lys
            20
```

<210> SEQ ID NO 26
<211> LENGTH: 17
<212> TYPE: PRT

<213> ORGANISM: Roseburia hominis

<400> SEQUENCE: 26

Thr Pro Glu Asp Tyr Thr Ala Phe Asn Gly Ile Glu Leu Tyr Gln Gly
1               5                   10                  15
Lys

<210> SEQ ID NO 27
<211> LENGTH: 6
<212> TYPE: PRT
<213> ORGANISM: Roseburia hominis

<400> SEQUENCE: 27

Ala Asn Thr Asp Val Lys
1               5

<210> SEQ ID NO 28
<211> LENGTH: 14
<212> TYPE: PRT
<213> ORGANISM: Roseburia hominis

<400> SEQUENCE: 28

Val Asp Gly Glu Ile Cys Tyr Val Ser Cys Gln Asn Val Lys
1               5                   10

<210> SEQ ID NO 29
<211> LENGTH: 67
<212> TYPE: PRT
<213> ORGANISM: Roseburia hominis

<400> SEQUENCE: 29

Gly Tyr Tyr Leu Glu Thr Gly Ser Val Thr Ala Ser Val Asp Val Thr
1               5                   10                  15

Gly Gln Glu Ser Val Gly Thr Glu Gln Leu Ser Gly Thr Glu Gln Met
                20                  25                  30

Glu Met Thr Gly Glu Pro Val Asn Ala Asp Thr Glu Gln Thr Glu
            35                  40                  45

Ala Ala Ala Gly Asp Gly Ser Phe Glu Thr Asp Val Tyr Thr Phe Ile
        50                  55                  60

Val Tyr Lys
65

<210> SEQ ID NO 30
<211> LENGTH: 4
<212> TYPE: PRT
<213> ORGANISM: Roseburia hominis

<400> SEQUENCE: 30

Asn Ala Val Lys
1

<210> SEQ ID NO 31
<211> LENGTH: 17
<212> TYPE: PRT
<213> ORGANISM: Roseburia hominis

<400> SEQUENCE: 31

Thr Pro Glu Asp Tyr Thr Ala Phe Ser Gly Ile Glu Leu Tyr Gln Gly
1               5                   10                  15
Lys

```
<210> SEQ ID NO 32
<211> LENGTH: 8
<212> TYPE: PRT
<213> ORGANISM: Artificial Sequence
<220> FEATURE:
<223> OTHER INFORMATION: FLAG tag

<400> SEQUENCE: 32

Asp Tyr Lys Asp Asp Asp Asp Lys
1               5

<210> SEQ ID NO 33
<211> LENGTH: 233
<212> TYPE: PRT
<213> ORGANISM: Artificial Sequence
<220> FEATURE:
<223> OTHER INFORMATION: Artificial variant of SG11
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid

<400> SEQUENCE: 33

Met Leu Glu Gly Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
                20                  25                  30

Thr Glu Leu Lys Ser Tyr Val Asp Ala Glu Val Glu Asp Tyr Thr Ala
            35                  40                  45

Glu His Gly Lys Xaa Ala Val Lys Val Glu Ser Leu Lys Val Glu Asp
        50                  55                  60

Gly Val Ala Lys Leu Lys Met Lys Tyr Lys Thr Pro Glu Asp Tyr Thr
65                  70                  75                  80

Ala Phe Xaa Xaa Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly
    130                 135                 140

Glu Ile Xaa Tyr Val Ser Xaa Gln Asn Val Lys Leu Thr Gly Lys Asp
145                 150                 155                 160

Ser Val Ser Ile Arg Asp Gly Tyr Tyr Leu Glu Thr Gly Ser Val Thr
                165                 170                 175

Ala Ser Val Asp Val Thr Gly Gln Glu Ser Val Gly Thr Glu Gln Leu
            180                 185                 190

Ser Gly Thr Glu Gln Met Glu Met Thr Gly Glu Pro Val Asn Ala Asp
        195                 200                 205

Asp Thr Glu Gln Thr Glu Ala Ala Ala Gly Asp Gly Ser Phe Glu Thr
    210                 215                 220
```

Asp Val Tyr Thr Phe Ile Val Tyr Lys
225                 230

<210> SEQ ID NO 34
<211> LENGTH: 233
<212> TYPE: PRT
<213> ORGANISM: Artificial Sequence
<220> FEATURE:
<223> OTHER INFORMATION: Artificial variant of SG11
<220> FEATURE:
<221> NAME/KEY: misc_feature
<222> LOCATION: (53)..(53)
<223> OTHER INFORMATION: Xaa is any amino acid other than Asn
<220> FEATURE:
<221> NAME/KEY: misc_feature
<222> LOCATION: (83)..(83)
<223> OTHER INFORMATION: Xaa is any amino acid other than Asn
<220> FEATURE:
<221> NAME/KEY: misc_feature
<222> LOCATION: (84)..(84)
<223> OTHER INFORMATION: Xaa is any amino acid other than Gly
<220> FEATURE:
<221> NAME/KEY: misc_feature
<222> LOCATION: (147)..(147)
<223> OTHER INFORMATION: Xaa is any amino acid other than Cys
<220> FEATURE:
<221> NAME/KEY: misc_feature
<222> LOCATION: (151)..(151)
<223> OTHER INFORMATION: Xaa is any amino acid other than Cys

<400> SEQUENCE: 34

Met Leu Glu Gly Glu Glu Ser Val Val Tyr Val Gly Lys Lys Gly Val
1               5                   10                  15

Ile Ala Ser Leu Asp Val Glu Thr Leu Asp Gln Ser Tyr Tyr Asp Glu
            20                  25                  30

Thr Glu Leu Lys Ser Tyr Val Asp Ala Glu Val Glu Asp Tyr Thr Ala
        35                  40                  45

Glu His Gly Lys Xaa Ala Val Lys Val Glu Ser Leu Lys Val Glu Asp
    50                  55                  60

Gly Val Ala Lys Leu Lys Met Lys Tyr Lys Thr Pro Glu Asp Tyr Thr
65                  70                  75                  80

Ala Phe Xaa Xaa Ile Glu Leu Tyr Gln Gly Lys Val Val Ala Ser Leu
                85                  90                  95

Ala Ala Gly Tyr Val Tyr Asp Gly Glu Phe Ala Arg Val Glu Glu Gly
            100                 105                 110

Lys Val Val Gly Ala Ala Thr Lys Gln Asp Ile Tyr Ser Glu Asp Asp
        115                 120                 125

Leu Lys Val Ala Ile Ile Arg Ala Asn Thr Asp Val Lys Val Asp Gly
    130                 135                 140

Glu Ile Xaa Tyr Val Ser Xaa Gln Asn Val Lys Leu Thr Gly Lys Asp
145                 150                 155                 160

Ser Val Ser Ile Arg Asp Gly Tyr Tyr Leu Glu Thr Gly Ser Val Thr
                165                 170                 175

Ala Ser Val Asp Val Thr Gly Gln Glu Ser Val Gly Thr Glu Gln Leu
            180                 185                 190

Ser Gly Thr Glu Gln Met Glu Met Thr Gly Glu Pro Val Asn Ala Asp
        195                 200                 205

Asp Thr Glu Gln Thr Glu Ala Ala Ala Gly Asp Gly Ser Phe Glu Thr
    210                 215                 220

Asp Val Tyr Thr Phe Ile Val Tyr Lys
225                 230

PROTEINS FOR THE TREATMENT OF EPITHELIAL BARRIER FUNCTION DISORDERS

CROSS-REFERENCE TO RELATED APPLICATIONS

This application is a National Stage Application under 35 U.S.C. §371 and claims the benefit of International Application No. PCT/US2018/026447, filed on Apr. 6, 2018, which claims the benefit of priority to U.S. provisional application No. 62/611,334 filed on Dec. 28, 2017, U.S. provisional application No. 62/607,706 filed on Dec. 19, 2017, and U.S. provisional application No. 62/482,963 filed on Apr. 7, 2017, each of which is hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: SEGE_001_03WO_SeqList_ST25.txt, date created, Apr. 4, 2018, file size≈45.3 kilobytes.

FIELD

The present disclosure relates to novel proteins and pharmaceutical compositions comprising said proteins that have application, inter alia, in the treatment of gastrointestinal inflammatory diseases and epithelial barrier function disorders. In some embodiments, the proteins and pharmaceutical compositions described herein have particular application in the treatment or prevention of disease states associated with abnormally permeable epithelial barriers as well as inflammatory bowel diseases or disorders.

BACKGROUND

Inflammatory bowel disease (IBD) is a heterogeneous disease of unknown etiology resulting in frequent and bloody bowel movements accompanied with histopathological damage to the gastrointestinal mucosa (Zhang et al., 2017, Front Immunol, 8:942). While specific triggers of disease remain poorly defined, one proposal of disease progression suggests a breakdown of intestinal barrier function allows bacteria or bacterial components to translocate into mucosal tissue (Coskun, 2014, Front Med (Lausanne), 1:24; Martini et al., 2017, Cell Mol Gastroenterol Hepatol, 4:33-46). Bacterial translocation results in activation of inflammatory signaling which triggers additional barrier disruption, resulting in a cyclic amplification loop of barrier disruption, bacterial translocation and inflammation. While many current therapies target inflammation, the lack of therapies promoting mucosal healing provides an opportunity for novel therapies promoting epithelial repair and intestinal barrier integrity.

Expanding upon the hypothesis that bacterial translocation can trigger IBD, more recent studies have demonstrated detrimental changes in intestinal microbiota, or dysbiosis, may promote development of IBD.

Currently, many IBD therapeutics available in the market merely aim to target and suppress the discussed inflammatory response associated with IBD. While helpful, this narrow therapeutic mode of action disregards the important contribution that epithelial barrier integrity plays in the etiology of the disease.

Thus, there is a great need in the art for the development of a therapeutic, which not only suppresses the immune system's inflammatory response, but that also acts in concert to restore the epithelial barrier function in an individual. Also, there is a need for the production of a protein therapeutic such as that described herein which is stable through the manufacturing and/or processing of the protein therapeutic as well as under long term storage conditions.

SUMMARY OF THE DISCLOSURE

The present disclosure addresses the important need in the medical community for a therapeutic which can effectively treat a subject suffering from a gastrointestinal disorder such as an inflammatory bowel disease (IBD). In one aspect, novel protein therapeutics are provided which can maintain epithelial barrier integrity and/or improve epithelial barrier repair. In some embodiments, the epithelial barrier is intestinal epithelial barrier. These protein therapeutics can also reduce inflammation of the intestine of the subject and/or decrease symptoms associated with inflammation of the intestine.

The protein therapeutics provided herein are useful in treating the numerous diseases and/or symptoms that may be associated with decreased gastrointestinal epithelial cell barrier function or integrity.

In some embodiments, the disclosure teaches novel protein therapeutics derived from the microbiome and methods of utilizing said protein therapeutics. In a particular embodiment, a protein derived from the microbiome and comprising an amino acid sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%, sequence identity to SEQ ID NO:19 is provided. In some embodiments, the therapeutic protein does not comprise an amino acid sequence identical to SEQ ID NO:3. In yet other embodiments, the therapeutic protein comprises an amino acid sequence which is not naturally occurring.

In some embodiments, the protein comprises the amino acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. In other embodiments, the protein comprises the amino acid sequence of SEQ ID NO:3. In still other embodiments, the protein comprises the amino acid sequence of SEQ ID NO:19.

In some embodiments, the protein comprises an amino acid sequence which is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or 100% identical to SEQ ID NO:19, wherein the amino acid sequence has at least 1, 2, 3 or 4 amino acid substitutions relative to SEQ ID NO:19 or to SEQ ID NO:3. In other embodiments, the amino acid sequence has at least 2 and less than 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid substitutions relative to SEQ ID NO:3. In still other embodiments, the therapeutic protein comprises an amino acid sequence which is not naturally occurring.

In some embodiments, the protein comprises the amino acid sequence of SEQ ID NO:3. In other embodiments with respect to SEQ ID NO:3, X53 is N, S, T, M, R, Q and/or X83 is N, R or K, and/or X84 is G or A, and/or X147 is C, S, T, M, V, L, A, or G, and/or X151 is C, S, T, M, V, L, A, or G. In still other embodiments, X53 is N, S or K and/or X83 is N or R and/or X84 is G or A and/or X147 is C, V, L or A and/or X151 is C, S, V, L or A.

In some embodiments, the protein is about 200 to 250 amino acids, 210 to 250 amino acids, 220 to 250 amino acids, 220 to 240 amino acids, 230 to 250 amino acids, 230 to 240 amino acids, or 230 to 235 amino acids, 220 to 275 amino acids, 220 to 260 amino acids, 230 to 260 amino acids, 240 to 250 amino acids, 250 to 260 amino acids, 230 to 256 amino acids, 240 amino acids to 256 amino acids, 245 amino acids to 256 amino acids in length. In other embodiments, the therapeutic protein is 220, 221, 222, 223, 224, 225, 226, 227, 228, 229, 230, 231, 232, 233, 234, 235, 236, 237, 238, 239, 240, 250, 251, 252, 253, 254, 255, 256, 257, 258, 259 or 260 amino acids in length.

In some embodiments, the disclosure teaches an antibody or fragment thereof which specifically binds the therapeutic protein comprising SEQ ID NO:19 or a variant thereof. In other embodiments, the antibody or fragment thereof does not bind a protein comprising an amino acid sequence identical to SEQ ID NO:3. In still other embodiments, the antibody or fragment thereof binds a protein comprising an amino acid sequence identical to SEQ ID NO:19 but does not bind a protein comprising an amino acid sequence identical to SEQ ID NO:3.

In some embodiments, the protein increases the barrier function of an epithelial cell layer in an in vitro assay, wherein the increase is relative to the barrier function in the assay in the absence of the protein. In other embodiments, the in vitro assay is a transepithelial electrical resistance (TEER) assay. In still other embodiments, the increase in barrier function is an increase in electrical resistance of at least 5%, 10%, 20%, 30%, 40%, 50%, 60%, 70%, 80%, or 90% greater than the electrical resistance in the assay in the absence of the protein. In some embodiments, the epithelial cell layer is an intestinal epithelial cell layer. In still other embodiments, the intestinal epithelial cell layer is a cell layer which comprises enterocytes and goblet cells.

In some embodiments, the protein decreases the secretion of a pro-inflammatory cytokine from a cell in an in vitro assay. In other embodiments, the in vitro assay comprises incubation of monocytic cells with heat killed *E. coli* in the presence and absence of the protein. In still other embodiments, the at least one pro-inflammatory cytokine is selected from the group consisting of TNF-α, IL-17, IL-10, IL-2, IFN-γ, IL-6, IL-12, IL-25, IL-33, IL-8, MCP-1, MIP-3α, CXCL1, and IL-23.

In some embodiments, the protein increases secretion of an anti-inflammatory cytokine from a cell in an in vitro assay. In other embodiments, the in vitro assay comprises incubation of a monocyte with heat killed *E. coli* in the presence and absence of the protein. In still embodiments, the at least one anti-inflammatory cytokine is selected from the group consisting of IL-4, IL-10, IL-13, IFN-α, and TGF-β.

In some embodiments, the protein reduces intestinal tissue pathology in a subject administered the protein. In some embodiments, the subject was induced to have intestinal tissue damage by treatment with a chemical. In other embodiments, the subject was treated with the chemical dextran sodium sulfate (DSS) to induce intestinal tissue damage. In still other embodiments, the subject is a mammal. In yet other embodiments, the animal is a rodent. In other embodiments, the subject is a non human primate.

In some embodiments, the therapeutic protein reduces gastrointestinal inflammation in a subject administered the protein. In other embodiments, the protein reduces intestinal mucosa inflammation in the subject. In still other embodiments, the protein improves intestinal epithelial cell barrier function or integrity in the subject.

In some embodiments, the protein increases the amount of mucin in intestinal tissue in a subject administered said protein.

In some embodiments, the protein increases intestinal epithelial cell wound healing in a subject administered the protein. In other embodiments, the protein increases intestinal epithelial cell wound healing in an in vitro assay.

In some embodiments, the protein prevents or reduces colon shortening in a subject administered the protein.

In some embodiments, the therapeutic protein modulates (i.e. increases or decreases) a cytokine in the blood, plasma, serum, tissue and/or mucosa of a subject administered the protein.

In some embodiments, the protein decreases the levels of at least one pro-inflammatory cytokine in the blood, plasma, serum, tissue and/or mucosa of the subject. In other embodiments, the at least one pro-inflammatory cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the protein increases the levels of at least one anti-inflammatory cytokine in the blood, plasma, serum, tissue and/or mucosa of the subject. In other embodiments, the at least one anti-inflammatory cytokine is selected from the group consisting of IL-4, IL-10, IL-13, IFN-α, and TGF-β.

In some embodiments, the protein decreases the level of at least one anti-inflammatory cytokine in the blood, plasma, serum, tissue and/or mucosa of the subject. In other embodiments, the at least one anti-inflammatory cytokine is selected from the group consisting of IL-4, IL-10, IL-13, IFN-α, and TGF-β.

In some embodiments, the disclosure teaches polynucleotides encoding a novel protein therapeutic and methods of expressing said nucleic acids in a host cell. In a particular embodiment, the polynucleotide comprises a sequence which encodes a protein that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or 100% identical to SEQ ID NO:19. In other embodiments, the polynucleotide comprises a sequence which encodes a protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identical to SEQ ID NO:19 and less than 100% identical to SEQ ID NO:3. In still other embodiments, the polynucleotide encodes a protein which is a non-naturally occurring variant of SEQ ID NO:1 or SEQ ID NO:3. In still other embodiments, the polynucleotide is codon-optimized for expression in a recombinant host cell. In yet other embodiments, the polynucleotide is codon-optimized for expression in *E. coli*.

In some embodiments, the disclosure teaches a nucleic acid which comprises a sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:20. In other embodiments, the nucleic acid comprises a sequence which is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:20 and less than 100% identical to SEQ ID NO:4. In still other embodiments, the nucleic acid comprises a sequence which is a non-naturally occurring variant of SEQ ID NO:2 or SEQ ID NO:4.

In some embodiments, the protein is chemically modified at the N-terminus and/or the C-terminus. In other embodiments, the N-terminus of the protein is chemically modified by acetylation. In still other embodiments, the C-terminus is chemically modified by amidation.

In some embodiments, the protein is pegylated.

In some embodiments, the protein is substantially purified and which is modified by glycosylation, ubiquitination, nitrosylation, methylation, acetylation, or lipidation.

In some embodiments, the protein is fused to second protein. In other embodiments, the second protein is an immunoglobulin Fc domain or a human serum albumin protein domain.

In some aspects, the disclosure provides a pharmaceutical composition for treating an inflammatory bowel disease, comprising: a therapeutic protein comprising an amino acid sequence having at least 70%, 75%, 80%, 85%, 90%, 91%, 92%, 93% 94%, 95%, 96%, 97%, 98%, 99%, 99.5%, 99.6%, 99.7%, 99.8% or 100% sequence identity to SEQ ID NO:19 and a pharmaceutically acceptable carrier. In some embodiments, the therapeutic protein is purified or substantially purified. In some embodiments, the protein comprises the amino acid sequence of SEQ ID NO:3. In an alternative embodiment, the protein does not comprise a sequence which is identical to SEQ ID NO:3 or the protein is a non-naturally occurring variant of SEQ ID NO:3. In other embodiments, the protein comprises an amino acid sequence selected from the group consisting of SEQ ID NO:5, SEQ ID NO:7, SEQ ID NO:9, SEQ ID NO:11, SEQ ID NO:13, SEQ ID NO:15, SEQ ID NO:17, and SEQ ID NO:19. In yet other embodiments, the protein comprises an amino acid sequence of SEQ ID NO:3, SEQ ID NO:7 or SEQ ID NO:19.

In some embodiments, the pharmaceutical composition is formulated for rectal, parenteral, intravenous, topical, oral, dermal, transdermal, or subcutaneous administration. In other embodiments, the pharmaceutical composition is a liquid, a gel, or a cream. In still other embodiments, the pharmaceutical composition is a solid composition comprising an enteric coating.

In some embodiments, the pharmaceutical composition is a cream, a capsule, a liquid, a gel, or an emulsion.

In some embodiments, the pharmaceutical composition is formulated to provide delayed release. In other embodiments, the delayed release is release into the gastrointestinal tract. In yet other embodiments, the delayed release is into the mouth, the small intestine, the large intestine and/or the rectum.

In some embodiments, the pharmaceutical composition is formulated to provide sustained release. In other embodiments, the sustained release is release into the gastrointestinal tract. In yet other embodiments, the sustained release is into the mouth, the small intestine, the large intestine and/or the rectum. In still other embodiments, the sustained release composition releases the therapeutic formulation over a time period of about 1 to 20 hours, 1 to 10 hours, 1 to 8 hours, 4 to 12 hours or 5 to 15 hours.

In some embodiments, the pharmaceutical composition further comprises a second therapeutic agent. In other embodiments, the second therapeutic agent is selected from the group consisting of an anti-diarrheal, a 5-aminosalicylic acid compound, an anti-inflammatory agent, an antibiotic, an anti-cytokine agent, an anti-inflammatory cytokine agent, a steroid, a corticosteroid, an immunosuppressant, a JAK inhibitor, an anti-integrin biologic, an anti-IL12/23R biologic, and a vitamin.

In some embodiments, the pharmaceutical composition further comprises a protease inhibitor. In still other embodiments, the protease inhibitor inhibits degradation of the therapeutic protein in the presence of fecal matter and/or in the presence of blood.

As aforementioned, these novel protein therapeutics are able to promote epithelial barrier function and integrity in a subject. In some embodiments, the epithelial barrier function is intestinal epithelial barrier function. Additionally, the therapeutic effect of the proteins includes suppression of an inflammatory immune response in an IBD individual. Thus, the disclosure provides detailed guidance for methods of utilizing the taught therapeutic proteins to treat a host of gastrointestinal inflammatory conditions, and disease states involving compromised gastrointestinal epithelial barrier integrity.

In some embodiments, a method for treating an inflammatory bowel disease or disorder in a patient in thereof is provided, comprising: administering to the patient a pharmaceutical composition, comprising: i) a therapeutic protein comprising an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or 100% sequence identity to SEQ ID NO:3, SEQ ID NO:9, SEQ ID NO:11, SEQ ID NO:13, SEQ ID NO:15, SEQ ID NO:17, or SEQ ID NO:19; and ii) a pharmaceutically acceptable carrier. In other embodiments of the method, the protein comprises an amino acid sequence identical to SEQ ID NO:3, SEQ ID NO:9, SEQ ID NO:11, SEQ ID NO:13, SEQ ID NO:15, SEQ ID NO:17, or SEQ ID NO:19. In still other embodiments, the protein is not identical to SEQ ID NO:3 or is a non-naturally occurring variant of SEQ ID NO:3.

In some embodiments, the patient has been diagnosed with intestinal inflammation. In other embodiments, the intestinal inflammation is in the small intestine and/or the large intestine. In still other embodiments, the intestinal inflammation is in the rectum. In still other embodiments, the patient has been diagnosed with pouchitis.

In some embodiments, the patient has been diagnosed with intestinal ulcers. In other embodiments, the patient has been diagnosed with draining enterocutaneous and/or rectovaginal fistulas.

In some embodiments, the patient has been diagnosed with Crohn's disease (CD). In other embodiments, the CD is mildly active CD. In still other embodiments, the CD is moderately to severely active CD. In yet other embodiments, the patient has been diagnosed with pediatric CD.

In some embodiments, the patient has been diagnosed with short bowel syndrome or irritable bowel syndrome.

In some embodiments, the patient has been diagnosed with mucositis. In other embodiments, the mucositis is oral mucositis. In still other embodiments, the mucositis is chemotherapy-induced mucositis, radiation therapy-induced mucositis, chemotherapy-induced oral mucositis, or radiation therapy-induced oral mucositis. In yet other embodiments, the mucositis is gastrointestinal mucositis. In still other embodiments, the gastrointestinal mucositis is mucositis of the small intestine, the large intestine, or the rectum.

In some embodiments, the administering to a patient diagnosed with CD resulted in a reduced number of draining enterocutaneous and/or rectovaginal fistulas. In other embodiments, the administering maintains fistula closure in adult patients with fistulizing disease.

In other embodiments, the patient has been diagnosed with ulcerative colitis (UC). In other embodiments, the UC is mildly active UC. In still other embodiments, the UC is moderately to severely active UC. In still other embodiments, the patient has been diagnosed with pediatric UC.

In some embodiments, the patient is in clinical remission from an IBD. In other embodiments, the patient is in clinical remission from UC, pediatric UC, CD or pediatric CD.

In some embodiments, the patient has an inflammatory bowel disease or disorder other than Crohn's disease or ulcerative colitis. In other embodiments, the patient has at least one symptom associated with inflammatory bowel disease.

In some embodiments, the administering reduces gastrointestinal inflammation and/or reduces intestinal mucosa inflammation associated with inflammatory bowel disease in the patient. In other embodiments, the administering improves intestinal epithelial cell barrier function or integrity in the patient.

In some embodiments, after the administering the patient experiences a reduction in at least one symptom associated with an inflammatory bowel disease or disorder. In other embodiments, the at least one symptom is selected from the group consisting of abdominal pain, blood in stool, pus in stool, fever, weight loss, frequent diarrhea, fatigue, reduced appetite, nausea, cramps, anemia, tenesmus, and rectal bleeding. In still other embodiments, after the administering the patient experiences reduced frequency of diarrhea, reduced blood in stool and/or reduced rectal bleeding.

In some embodiments, the patient has experienced inadequate response to conventional therapy. In other embodiments, the conventional therapy is treatment with an aminosalicylate, a corticosteroid, a thiopurine, methotrexate, a JAK inhibitor, a sphingosine 1-phosphate (SIP) receptor inhibitor, an anti-integrin biologic, an anti-IL12/23R or anti-IL23/p10 biologic, and/or an anti-tumor necrosis factor agent or biologic.

In some embodiments, the administering modulates (i.e. increases or decreases) levels of a cytokine in the blood, plasma, serum, mucosa or tissue of the patient.

In some embodiments, the administering suppresses the levels of at least one pro-inflammatory cytokine in the patient. In other embodiments, the at least one pro-inflammatory cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the administering increases the levels of at least one anti-inflammatory cytokine in the blood, plasma, serum, mucosa or tissue of the patient. In other embodiments, the at least one anti-inflammatory cytokine is selected from the group consisting of IL-4, IL-10, IL-13, IFN-α, and TGF-β.

In some embodiments, the administering decreases the level of at least one anti-inflammatory cytokine in the blood, plasma, serum, mucosa or tissue of the patient. In other embodiments, the at least one anti-inflammatory cytokine is selected from the group consisting of IL-4, IL-10, IL-13, IFN-α, and TGF-β.

In some embodiments, the administering increases the amount of mucin in intestinal lumen of the patient.

In some embodiments, the administering increases intestinal epithelial cell wound healing in the patient.

In some embodiments, the administering prevents or reduces colon shortening in the patient.

In some embodiments, the administering comprises rectal, intravenous, parenteral, oral, topical, dermal, transdermal or subcutaneous administering of the pharmaceutical composition to the patient. In other embodiments, the administering is to the gastrointestinal lumen.

In some embodiments, the patient is also administered at least one second therapeutic agent. In other embodiments, the at least one second therapeutic agent is selected from the group consisting of an anti-diarrheal, an anti-inflammatory agent, an antibody, an antibiotic, or an immunosuppressant. In still other embodiments, the at least one second therapeutic agent is an aminosalicylate, a steroid, or a corticosteroid. In other embodiments, the at least one second therapeutic agent is selected from the group consisting of adalimumab, pegol, golimumab, infliximab, vedolizumab, ustekinumab, tofacitinib, and certolizumab or certolizumab pegol.

In some aspects, an expression vector is provided, comprising an exogenous polynucleotide that encodes a protein comprising an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:19.

In some embodiments, the polynucleotide encodes a protein comprising an amino acid sequence having at least 99% or 100% identity to SEQ ID NO:5, SEQ ID NO:7, SEQ ID NO:9 SEQ ID NO:11, SEQ ID NO:13, SEQ ID NO:15, SEQ ID NO:17, or SEQ ID NO:19. In other embodiments, the polynucleotide encodes a protein comprising the amino acid sequence of SEQ ID NO:3. In still other embodiments, the polynucleotide encodes a protein comprising an amino acid sequence that is not identical to SEQ ID NO:3.

In some aspects, an expression system is provided, comprising a host cell and the expression vector comprising the aforementioned exogenous polynucleotide.

In some embodiments, the host cell is prokaryotic or eukaryotic. In other embodiments, the host cell is mammalian cell, a yeast cell or a bacterial cell. In still other embodiments, the bacterial cell is *Escherichia coli*. In yet other embodiments, the mammalian cell is a CHO cell.

In some aspects, a method of producing the protein is provided.

In some embodiments, the method for producing the protein comprises transforming or transfecting the aforementioned host cell with the aforementioned expression vector, culturing the transformed or transfected host cell under conditions sufficient for the expression of the aforementioned protein encoded by the aforementioned exogenous polynucleotide. In other embodiments, the method further comprises purifying the protein from the transformed or transfected host cell and culture media.

In some embodiments, methods of treating a disease—such as an intestinal epithelium barrier function associated disease—are provided, which utilize any sequence disclosed in the current application and sequence listing.

BRIEF DESCRIPTION OF THE DRAWINGS

FIG. 17 shows results of the multiple sequence alignment analysis of SG-11 (SEQ ID NO:7) with similar protein sequences from *Roseburia* species.

FIG. 18 shows effects of conditions from FIG. 18A, FIG. 18B, FIG. 18C, FIG. 18D, FIG. 18E, FIG. 18F, FIG. 18G, FIG. 18H, and FIG. 18I on SG-11 stability. See Example 14 for the conditions associated with FIG. 18A to FIG. 18I.

FIG. 19 shows effects of conditions from FIG. 19A, FIG. 19B, FIG. 19C, FIG. 19D, FIG. 19E, FIG. 19F, FIG. 19G, FIG. 19H, and FIG. 19I on SG-11V5 stability. See Example 14 for the conditions associated with FIG. 19A to FIG. 19I.

FIG. 27A shows results of the multiple sequence alignment analysis of SG-11 (SEQ ID NO:7) with SG-11 variants (SEQ ID NO:11, SEQ ID NO:13, SEQ ID NO:15, SEQ ID NO:17, SEQ ID NO:19), and FIG. 27B shows results of the percent identity matrix based on the multiple sequence alignment analysis. The Clustal Omega program provided by EMBL-EBI was used for the multiple alignment analysis described herein.

DETAILED DESCRIPTION

Figure 1A:
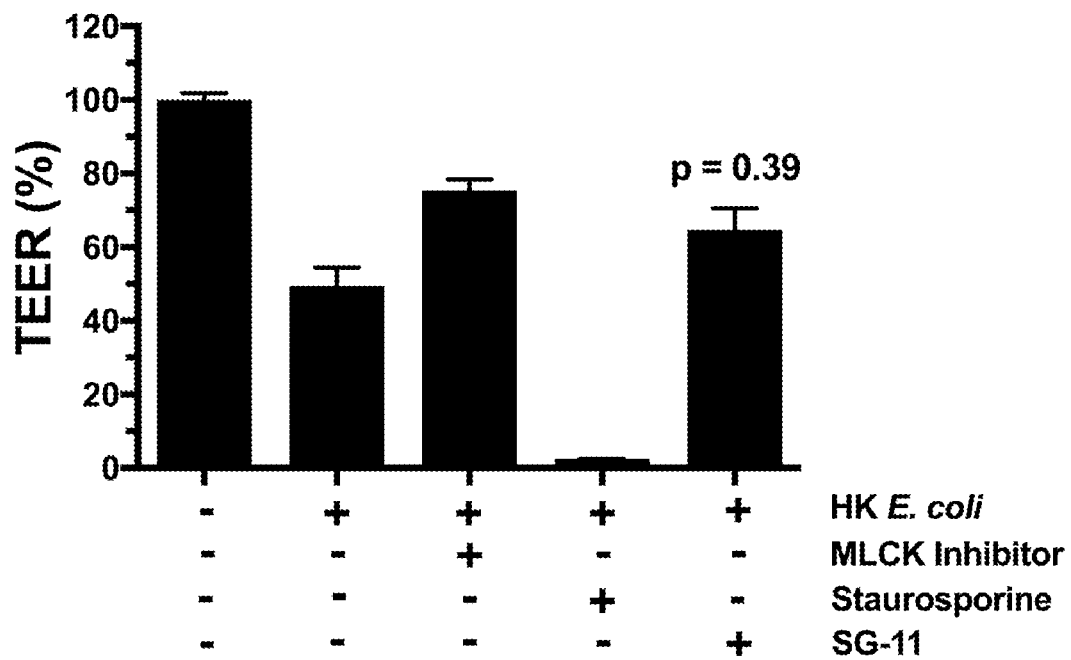
FIG. 1A and FIG. 1B show restoration, by SG-11, of epithelial barrier integrity following inflammation induced disruption, as described in Example 2.

The present disclosure provides novel protein therapeutics that are useful in the treatment of subjects suffering from symptoms associated with gastrointestinal disorders. For example, these proteins can promote or enhance epithelial barrier function and/or integrity.

The protein may also suppress the inflammatory immune response in an IBD individual. The protein therapeutic provided herein is useful in treating the numerous diseases that are associated with decreased gastrointestinal epithelial cell barrier function or integrity and inflammation of the intestine.

In the present disclosure, provided are also protein variants that have therapeutic activity comparable to or superior to the original protein, but the protein variants have enhanced stability through the manufacturing and processing of the protein therapeutic products as well as under long-term storage conditions.

Definitions

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art. Thus, while the following terms are believed to be well understood by one of ordinary skill in the art, the following definitions are set forth to facilitate explanation of the presently disclosed subject matter.

Throughout this specification, the word "comprise" or variations such as "comprises" or "comprising" will be understood to imply the inclusion of a stated component, or group of components, but not the exclusion of any other components, or group of components.

The term "a" or "an" refers to one or more of that entity, i.e. can refer to a plural referents. As such, the terms "a" or "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

The term "including" is used to mean "including but not limited to." "Including" and "including but not limited to" are used interchangeably.

The terms "gastrointestinal" or "gastrointestinal tract," "alimentary canal," and "intestine," as used herein, may be used interchangeably to refer to the series of hollow organs extending from the mouth to the anus and including the mouth, esophagus, stomach, small intestine, large intestine, rectum and anus. The terms "gastrointestinal" or "gastrointestinal tract," "alimentary canal," and "intestine" are not always intended to be limited to a particular portion of the alimentary canal.

The term "SG-11" as used herein refers to a protein comprising the amino acid sequence of SEQ ID NO:3 and also to variants thereof having the same or similar functional activity as described herein. Accordingly, SG-11 can refer herein to proteins comprising or consisting of SEQ ID NO:1, SEQ ID NO:3, SEQ ID NO:5, SEQ ID NO:7, or SEQ ID NO:9, or variants or fragments thereof. Examples of SG-11 variants include but are not limited to SEQ ID NO:11 (SG-11V1), SEQ ID NO:13 (SG-11V2), SEQ ID NO:15 (SG-11V3), SEQ ID NO:17 (SG-11V4), and SEQ ID NO:19 (SG-11V5). In U.S. provisional patent applications (62/482, 963, filed Apr. 7, 2017; 62/607,706, filed Dec. 19, 2017; 62/611,334, filed Dec. 28, 2017, to which the present specification claims priority and each of which is incorporated herein by reference in its entirety) the term "Experimental Protein 1" and variants thereof was used and is synonymous with SG-11 as used herein or variants thereof.

A "signal sequence" (also termed "presequence," "signal peptide," "leader sequence," or "leader peptide") refers to a sequence of amino acids located at the N-terminus of a nascent protein, and which can facilitate the secretion of the protein from the cell. The resultant mature form of the extracellular protein lacks the signal sequence, which is cleaved off during the secretion process.

The recitations "sequence identity," "percent identity," "percent homology," or for example, comprising a "sequence 50% identical to," as used herein, refer to the extent that sequences are identical on a nucleotide-by-nucleotide or amino acid-by-amino acid basis, over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The phrases "substantially similar" and "substantially identical" in the context of at least two nucleic acids or polypeptides typically means that a polynucleotide or polypeptide comprises a sequence that has at least about 70%, 75%, 80%, 85%, 86%, 87%, 88%, 89%, 90%, 91%, 92%, 93%, 94%, 95%, 96%, 97%, 98%, 99%, 99.5%, 99.6%, 99.7% or even 99.8% sequence identity, in comparison with a reference polynucleotide or polypeptide. In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

Related (and derivative) proteins encompass "variant" proteins. Variant proteins can differ from another (i.e., parental) protein and/or from one another by a small number of amino acid residues. A variant may include one or more amino acid mutations (e.g., amino acid deletion, insertion or substitution) as compared to the parental protein from which it is derived.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more "conservative substitutions." An example of a conservative substitution is the exchange of an amino acid in one of the following groups for another amino acid of the same group (see U.S. Pat. No. 5,767,063; Kyte and Doolittle (1982) J. Mol. Biol. 157:105-132). (1) Hydrophobic: Norleucine, Ile, Val, Leu, Phe, Cys, Met; (2) Neutral hydrophilic: Cys, Ser, Thr; (3) Acidic: Asp, Glu; (4) Basic: Asn, Gln, His, Lys, Arg;

(5) Residues that influence chain orientation: Gly, Pro; (6) Aromatic: Trp, Tyr, Phe; and (7) Small amino acids: Gly, Ala, Ser. Thus, the term "conservative substitution" with respect to an amino acid denotes that one or more amino acids are replaced by another, chemically similar residue, wherein said substitution does not generally affect the functional properties of the protein. Examples include substitution of amino acid residues with similar characteristics, e.g., small amino acids, acidic amino acids, polar amino acids, basic amino acids, hydrophobic amino acids and aromatic amino acids. In some embodiments, the disclosure provides for proteins that have at least one non-naturally occurring, conservative amino acid substitution relative to the amino acid sequence identified in SEQ ID NO:3 or SEQ ID NO:17. Some common exemplary examples of conservative amino acid substitutions are found below.

The term "amino acid" or "any amino acid" refers to any and all amino acids, including naturally occurring amino acids (e.g., α-amino acids), unnatural amino acids, modified amino acids, and unnatural or non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur, e.g., in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 unnatural amino acids are known and thousands of more combinations are possible. "Modified" amino acids include amino acids (e.g., natural amino acids) that have been chemically modified to include a group, groups, or chemical moiety not naturally present on the amino acid.

As used herein, a "synthetic nucleotide sequence" or "synthetic polynucleotide sequence" is a nucleotide sequence that is not known to occur in nature, or that is not naturally occurring. Generally, such a synthetic nucleotide sequence will comprise at least one nucleotide difference when compared to any other naturally occurring nucleotide sequence. As used herein, a "synthetic amino acid sequence" or "synthetic peptide sequence" or "synthetic polypeptide sequence" or "synthetic protein sequence" is an amino acid sequence that is not known to occur in nature, or that is not naturally occurring. Generally, such a synthetic amino acid sequence will comprise at least one amino acid difference when compared to any other naturally occurring amino acid sequence.

As used herein, a "synthetic protein" or "synthetic therapeutic protein" means a protein that comprises an amino acid sequence that contains one or more amino acids substituted with different amino acids relative to a naturally occurring amino acid sequence. That is, a "synthetic protein" comprises an amino acid sequence that has been altered to contain at least one non-naturally occurring substitution modification at a given amino acid position(s) relative to a naturally occurring amino acid sequence.

The term "about" as used herein with respect to % sequence identity, or % sequence homology, of a nucleic acid sequence, or amino acid sequence, means up to and including ±1.0% in 0.1% increments. For example "about 90%" sequence identity includes 89.0%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, and 91%. If not used in the context of % sequence identity, then "about" means ±1%, 2%, 3%, 4%, 5%, 6%, 7%, 8%, 9%, or 10%, depending upon context of the value in question.

For the most part, the names of natural and non-natural aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader.

Throughout the present specification, unless natural amino acids are referred to by their full name (e.g., alanine, arginine, etc.), they are designated by their conventional three-letter or single-letter abbreviations (e.g., Ala or A for alanine, Arg or R for arginine, etc.). Unless otherwise indicated, three-letter and single-letter abbreviations of amino acids refer to the L-isomeric form of the amino acid. The term "L-amino acid," as used herein, refers to the "L" isomeric form of a peptide, and conversely the term "D-amino acid" refers to the "D" isomeric form of a peptide (e.g., Dasp, (D)Asp or D-Asp; Dphe, (D)Phe or D-Phe). Amino acid residues in the D isomeric form can be substituted for any L-amino acid residue, as long as the desired function is retained by the peptide. D-amino acids may be indicated as customary in lower case when referred to using single-letter abbreviations.

In the case of less common or non-natural amino acids, unless they are referred to by their full name (e.g., sarcosine, ornithine, etc.), three- or four-character codes are frequently employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (α-glutamic acid), Gaba (γ-aminobutanoic acid), β-Pro (pyrrolidine-3-carboxylic acid), and 8Ado (8-amino-3,6-dioxaoctanoic acid), Abu (2-amino butyric acid), βhPro (β-homoproline), βhPhe (β-homophenylalanine) and Bip (β,β diphenylalanine), and Ida (Iminodiacetic acid).

Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the disclosure, a C-terminal "—OH" moiety may be substituted for a C-terminal "—NH$_2$" moiety, and vice-versa.

The term "Ac," as used herein, refers to acetyl protection through acylation of the C- or N-terminus of a polypeptide. In certain peptides shown herein, the NH$_2$ locates at the C-terminus of the peptide indicates an amino group. The term "carboxy," as used herein, refers to —CO$_2$H.

The term "pharmaceutically acceptable salt," as used herein, represents salts or zwitterionic forms of the peptides, proteins, or compounds of the present disclosure, which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present disclosure can be quatemized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties. Selection, and Use* by Stahl and Wermuth (Wiley-VCH, 2002).

As used herein, the term "at least a portion" or "fragment" of a nucleic acid or polypeptide means a portion having the minimal size characteristics of such sequences, or any larger fragment of the full length molecule, up to and including the full length molecule.

The term "primer" as used herein refers to an oligonucleotide which is capable of annealing to a target polynucleotide.

As used herein, the phrases "recombinant construct," "expression construct," "chimeric construct," "construct," and "recombinant DNA construct" are used interchangeably herein and are well-known to the ordinarily skilled artisan.

As used herein, the term "host cell" refers to a cell or cell line into which a recombinant expression vector for production of a polypeptide may be introduced for expression of the polypeptide.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system.

The terms "patient," "subject," and "individual" may be used interchangeably and refer to either a human or a non-human animal. These terms include mammals such as humans, non-human primates, livestock animals (e.g., bovines, porcines), companion animals (e.g., canines, felines) and rodents (e.g., mice and rats). In certain embodiments, the terms refer to a human patient. In exemplary embodiments, the terms refer to a human patient that suffers from a gastrointestinal inflammatory condition.

As used herein, "improved" should be taken broadly to encompass improvement in an identified characteristic of a disease state, said characteristic being regarded by one of skill in the art to generally correlate, or be indicative of, the disease in question, as compared to a control, or as compared to a known average quantity associated with the characteristic in question. For example, "improved" epithelial barrier function associated with application of a protein of the disclosure can be demonstrated by comparing the epithelial barrier integrity of a human treated with a protein of the disclosure, as compared to the epithelial barrier integrity of a human not treated. Alternatively, one could compare the epithelial barrier integrity of a human treated with a protein of the disclosure to the average epithelial barrier integrity of a human, as represented in scientific or medical publications known to those of skill in the art. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments. Thus, an "inhibited immune response" or the "inhibition of inflammatory cytokines" does not require absolute inhibition.

Thus, as used herein, the terms "increase," "suppress" or "reduce," or grammatical equivalents thereof, indicate values that are relative to a reference (e.g., baseline) measurement, such as a measurement taken under comparable conditions (e.g., in the same individual prior to initiation of treatment described herein, or a measurement in a control individual (or multiple control individuals) in the absence of treatment) described herein. In some embodiments, a suitable control is a baseline measurement, such as a measurement in the same individual prior to initiation of the treatment described herein, or a measurement in a control individual (or multiple control individuals) in the absence of the treatment described herein.

As used herein, the term "IBD" or "inflammatory bowel disease" refers to conditions in which individuals have chronic or recurring immune response and inflammation of the gastrointestinal (GI) tract. The two most common inflammatory bowel diseases are ulcerative colitis (UC) and Crohn's disease (CD).

As used herein, the term "therapeutically effective amount" refers to an amount of a therapeutic agent (e.g., a peptide, polypeptide, or protein of the disclosure), which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of, or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular patient may depend upon a variety of factors including the particular form of disease being treated; the severity of the condition or pre-condition; the activity of the specific therapeutic agent employed; the specific composition employed; the age, body weight, general health, sex and diet of the patient; the time of administration, route of administration, and/or rate of excretion or metabolism of the specific therapeutic agent employed; the duration of the treatment; and like factors as is well known in the medical arts. The current disclosure utilizes therapeutically effective amounts of novel proteins, and compositions comprising same, to treat a variety of diseases, such as: gastrointestinal inflammatory diseases or diseases involving gastrointestinal epithelial barrier malfunction. The therapeutically effective amounts of the administered protein, or compositions comprising same, will in some embodiments reduce inflammation associated with IBD or repair gastrointestinal epithelial barrier integrity and/or function.

As used herein, the term "treatment" (also "treat" or "treating") refers to any administration of a therapeutic agent (e.g., a peptide, polypeptide, or protein of the disclosure), according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., chronic or recurring immune response and inflammation of the gastrointestinal (GI) tract); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

"Pharmaceutical" implies that a composition, reagent, method, and the like, are capable of a pharmaceutical effect, and also that the composition is capable of being administered to a subject safely. "Pharmaceutical effect," without limitation, can imply that the composition, reagent, or method, is capable of stimulating a desired biochemical, genetic, cellular, physiological, or clinical effect, in at least one individual, such as a mammalian subject, for example, a human, in at least 5% of a population of subjects, in at least 10%, in at least 20%, in at least 30%, in at least 50% of subjects, and the like. "Pharmaceutically acceptable" means approved by a regulatory agency of the Federal or a state government or listed in the U.S. Pharmacopoeia or other generally recognized pharmacopoeia for safe use in animals, and more particularly safe use in humans. "Pharmaceutically acceptable vehicle" or "pharmaceutically acceptable excipient" refers to a diluent, adjuvant, excipient or carrier with which a protein as described herein is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease, or causing the symptom to develop with less severity than in absence of the treatment). "Prevention" or "prophylaxis" may refer to delaying the onset of the disease or disorder.

The therapeutic pharmaceutical compositions taught herein may comprise one or more natural products. However, in certain embodiments, the therapeutic pharmaceutical compositions themselves do not occur in nature. Further, in certain embodiments, the therapeutic pharmaceutical compositions possess markedly different characteristics, as compared to any individual naturally occurring counterpart, or composition component, which may exist in nature. That is, in certain embodiments, the pharmaceutical compositions taught herein—which comprise a therapeutically effective amount of a purified protein—possess at least one structural and/or functional property that impart markedly different characteristics to the composition as a whole, as compared to any single individual component of the composition as it may exist naturally. The courts have determined that compositions comprising natural products, which possess markedly different characteristics as compared to any individual component as it may exist naturally, are statutory subject matter. Thus, the taught therapeutic pharmaceutical compositions as a whole possess markedly different characteristics. These characteristics are illustrated in the data and examples taught herein.

Details of the disclosure are set forth herein. Although methods and materials similar or equivalent to those described herein can be used in the practice or testing of the present disclosure, illustrative methods and materials are now described. Other features, objects, and advantages of the disclosure will be apparent from the description and from the claims.

Therapeutic Proteins Derived from the Microbiome—Overview of the Disclosure

Numerous diseases and disorders are associated with decreased gastrointestinal epithelial cell barrier function or integrity. These diseases and disorders are multifaceted and present diagnostically in a myriad of ways. One such disease is inflammatory bowel disease (IBD), the incidence and prevalence of which is increasing with time and in different regions around the world, indicating its emergence as a global disease. (Molodecky et al., Gastroenterol 142:46-54, 2012). IBD is a collective term that describes conditions with chronic or recurring immune response and inflammation of the gastrointestinal (GI) tract. The two most common inflammatory bowel diseases are ulcerative colitis (UC) and Crohn's disease (CD). Both are marked by an abnormal response of the GI immune system. Normally, immune cells protect the body from infection. In people with IBD, however, this immune system mistakes food, bacteria, and other materials in the intestine for pathogens and an inflammatory response is launched into the lining of the intestines, creating chronic inflammation. When this happens, the patient experiences the symptoms of IBD.

IBD involves chronic inflammation of all, or part, of the digestive tract. Both UC and CD usually involve, for example, severe diarrhea, abdominal pain, fatigue, and weight loss. IBD and associated disorders can be debilitating and sometimes lead to life-threatening complications.

With respect to intestinal barrier integrity, loss of integrity of the intestinal epithelium plays a key pathogenic role in IBD. Maloy, Kevin J.; Powrie. Fiona, "Intestinal homeostasis and its breakdown in inflammatory bowel disease," (2011) Nature. 474 (7351): 298-306. It is hypothesized that detrimental changes in the intestinal microbiota induce an inappropriate or uncontrolled immune response that results in damage to the intestinal epithelium. Breaches in this critical intestinal epithelium barrier allow further infiltration of microbiota that, in turn, elicit further immune responses. Thus, IBD is a multifactorial disease that is driven in part by an exaggerated immune response to gut microbiota that can cause defects in epithelial barrier function.

Microbiome profiling of IBD patients has revealed distinct profiles such as increased Proteobacteria, including adherent-invasive *E. coli*, often at the expense of potentially beneficial microbes such as *Roseburia* spp (Machiels et al., 2014, Gut, 63:1275-1283; Patterson et al., 2017, Front Immunol, 8:1166; Shawki and McCole, 2017, Cell Mol Gastroenterol Hepatol, 3:41-50). Moreover, a decrease in *Roseburia hominis* was linked with dysbiosis in patients with ulcerative colitis. IBD affected individuals have been found to have 30-50 percent reduced biodiversity of commensal bacteria, such as decreases in Firmicutes (namely Lachnospiraceae) and Bacteroidetes. Further evidence of the role of gut flora in the cause of inflammatory bowel disease is that IBD affected individuals are more likely to have been prescribed antibiotics in the 2-5 year period before their diagnosis than unaffected individuals. See, Aroniadis O C, Brandt L J, "Fecal microbiota transplantation: past, present and future," (2013) Curr. Opin. Gastroenterol. 29 (1) (2013): 79-84.

Protective bacterial communities, probiotics and bacterially derived metabolites have been demonstrated to improve disease in various clinical and pre-clinical studies. For example, fecal microbial transfer (FMT) experiments have shown some success in IBD patients, although challenges still exist with FMT (Moayyedi et al., 2015, Gastroenterology, 149:102-109 e106; Qazi et al., 2017, Gut Microbes, 8:574-588; Narula et al., 2017, Inflamm Bowel Dis, 23:1702-1709). In other studies treatment with probiotics including VSL #3, *Lactobacillus* spp. and *Bifidobacterium* spp. have also shown to have beneficial effects in humans and animal models (Srutkova et al., 2015, PLoS One, 10:e0134050; Pan et al., 2014, Benef Microbes, 5:315-322; Huynh et al., 2009, Inflamm Bowel Dis, 15:760-768; Bibiloni et al., 2005, Am J Gastroenterol, 100:1539-1546). Furthermore, bacterial products such as p40 from *L. rhamnosus* GG and Amuc-1100 from *A. muciniphila* have been shown to promote barrier function and protect in animal models of IBD and metabolic disease, receptively (Yan et al., 2011, J Clin Invest, 121:2242-2253; Plovier et al., Nat Med, 23:107-113).

While uses of live microbial populations to treat diseases is increasingly common, such methods rely on the ability of the administered bacteria to survive in the host or patient and to interact with the host tissues in a beneficial and therapeutic way. An alternative approach, provided here, is to identify microbially-encoded proteins and variants thereof which can affect cellular functions in the host and provide therapeutic benefit. Such proteins can be administered, for example, as pharmaceutical compositions comprising a substantially isolated or purified therapeutic, bacterially-derived protein or as a live biotherapeutic (bacterium) engineered to express the therapeutic protein as an exogenous protein. Moreover, methods of treatment comprising administration of the therapeutic protein are not limited to the gut (small intestine, large intestine, rectum) but may also include treatment of other disorders within the alimentary canal such as oral mucositis.

To identify microbially-derived proteins which may have therapeutic application in gastrointestinal inflammatory disorders, mucosal biopsies from humans who were healthy or who were diagnosed with IBD (UC) were analyzed to determine the microbial compositions of these mucosal biopsies. A comparison of the bacterial profiles from healthy vs. diseased subjects identified bacteria that were either likely to be beneficial (greater numbers in healthy vs. diseased) or detrimental (lower numbers in healthy vs. diseased). Among the bacterial species identified as beneficial was *Roseburia hominis*, consistent with studies referenced above. Extensive bioinformatics analysis was then performed to predict proteins encoded by the bacterium and then to identify those proteins which are likely to be secreted by the bacterium. Proteins which were predicted to be secreted proteins were then characterized using a series of in vitro assays to study the effect of each protein on epithelial barrier integrity, cytokine production and/or release, and wound healing. Proteins identified as functioning to increase epithelial barrier integrity were then assessed in an in vivo mouse model for colitis. One such protein, identified herein as "SG-11," demonstrated both in vitro and in vivo activity indicative of its ability to provide therapeutic benefit for improving epithelial barrier integrity and for treating diseases and disorders associated with epithelial barrier integrity as well as treating inflammatory gastrointestinal diseases such as IBDs, as described in more detail below.

The SG-11 Protein

The protein referred to herein as SG-11 is encoded within a 768 nucleotide sequence (SEQ ID NO:2) present in the genome of *Roseburia hominis*. A complete genomic sequence for *R. hominis* strain can be found at GenBank accession number CP003040 (the sequence incorporated herein by reference in its entirety). A 16S rRNA gene sequence for the *Roseburia hominis* strain can be found at GenBank accession number AJ270482. The full-length protein encoded by the *R. hominis* genomic sequence is 256 amino acids in length (SEQ ID NO:1), wherein residues 1-24 are predicted to be a signal peptide which is cleaved in vivo to produce a mature protein of 232 amino acids (SEQ ID NO:3; encoded by SEQ ID NO:4). Recombinant SG-11 can be expressed with an N-terminal methionine (encoded by the codon ATG) to produce a mature protein of 233 amino acids (SEQ ID NO:7).

As detailed in the Examples, e.g., Example 1, SG-11 was recombinantly expressed in different commercially available and routinely used expression vectors. For example, SG-11 (a protein comprising SEQ ID NO:3), was expressed using a pGEX expression vector which expresses the protein of interest with a GST tag and protease site which is cleaved after expression and purification, a pET-28 expression vector which adds an N-terminal FLAG tag, and a pD451 expression vector which was used to express the SG-11 protein consisting of SEQ ID NO:7 and having no N-terminal tag. Experiments performed and repeated with these proteins showed that the minor N-terminal and/or C-terminal variations resulting from the use of the different protein expression systems and DNA constructs retained equivalent functional activity in in vivo and in vitro assays. It is understood that unless otherwise indicated, the term "SG-11" refers herein to the amino acid sequence depicted herein as SEQ ID NO:3 and such variants of the protein comprising the amino acid sequence of SEQ ID NO:3 (including but not limited to SEQ ID NO:1, SEQ ID NO:5, SEQ ID NO:7). SG-11 variants can include variations in amino acid residues (substitution, insertion, deletion) as well as modifications such as fusion constructs and post-translational modifications (phosphorylation, glycosylation, etc.). Some exemplary embodiments of the SG-11 protein and encoding nucleic acids are provided in Table 1 below.

TABLE 1

| Amino Acid Sequence | Encoding Nucleic Acid Sequence |
| --- | --- |
| SEQ ID NO: 1<br>MKRLVCTVCSVLLCAGLL<br>SGCGTSLEGEESVVYVGK<br>KGVIASLDVETLDQSYYDE<br>TELKSYVDAEVEDYTAEH<br>GKNAVKVESLKVEDGVAK<br>LKMKYKTPEDYTAFNGIEL<br>YQGKVVASLAAGYVYDG<br>EFARVEEGKVVGAATKQD<br>IYSEDDLKVAIIRANTDVK<br>VDGEICYVSCQNVKLTGK<br>DSVSIRDGYYLETGSVTAS<br>VDVTGQESVGTEQLSGTE<br>QMEMTGEPVNADDTEQTE<br>AAAGDGSFETDVYTFIVYK | SEQ ID NO: 2<br>ATGAAGAGATTAGTGTGCACGGTCTGCAGTGTACTGT<br>TGTGTGCGGGACTTCTCTCCGGATGCGGTACCTCGCT<br>GGAGGGAGAGGAAAGTGTCGTGTACGTGGGAAAGA<br>AAGGCGTGATAGCGTCGCTGGATGTGGAGACGCTCG<br>ATCAGTCCTACTACGATGAGACGGAACTGAAGTCCT<br>ATGTGGATGCAGAGGTGGAAGATTACACCGCGGAGC<br>ATGGTAAAAATGCAGTCAAGGTGGAGAGCCTTAAGG<br>TGGAAGACGGTGTGGCGAAGCTTAAGATGAAGTACA<br>AGACACCGGAGGATTATACCGCATTTAATGGAATTG<br>AACTCTATCAGGGGAAAGTCGTTGCTTCCCTGGCGGC<br>AGGATACGTCTACGACGGGGAGTTCGCCCGCGTGGA<br>GGAAGGCAAGGTTGTGGGAGCTGCCACAAAACAGGA<br>TATTTACTCTGAGGATGATTTGAAAGTTGCCATCATC<br>CGTGCCAATACGGATGTGAAGGTGGACGGTGAGATC<br>TGCTATGTCTCCTGTCAGAATGTGAAGCTGACCGGAA<br>AAGACAGTGTGTCGATCCGTGACGGATATTATCTTGA<br>GACGGGAAGCGTGACGGCATCCGTGGATGTGACCGG<br>ACAGGAGAGCGTCGGGACCGAGCAGCTTTCGGGAAC<br>CGAACAGATGGAGATGACCGGGGAGCCGGTGAATGC<br>GGATGATACCGAGCAGACAGAGGCGGCGGCCGGTGA<br>CGGTTCGTTCGAGACAGACGTATATACTTTCATTGTC<br>TACAAA |
| SEQ ID NO: 3<br>LEGEESVVYVGKKGVIASL<br>DVETLDQSYYDETELKSY<br>VDAEVEDYTAEHGKNAVK<br>VESLKVEDGVAKLKMKYK<br>TPEDYTAFNGIELYQGKVV<br>ASLAAGYVYDGEFARVEE<br>GKVVGAATKQDIYSEDDL<br>KVAIIRANTDVKVDGEICY<br>VSCQNVKLTGKDSVSIRDG<br>YYLETGSVTASVDVTGQES<br>VGTEQLSGTEQMEMTGEP<br>VNADDTEQTEAAAGDGSF<br>ETDVYTFIVYK | SEQ ID NO: 4<br>CTGGAGGGAGAGGAAAGTGTCGTGTACGTGGGAAAG<br>AAAGGCGTGATAGCGTCGCTGGATGTGGAGACGCTC<br>GATCAGTCCTACTACGATGAGACGGAACTGAAGTCC<br>TATGTGGATGCAGAGGTGGAAGAnACACCGCGGAG<br>CATGGTAAAAATGCAGTCAAGGTGGAGAGCCTTAAG<br>GTGGAAGACGGTGTGGCGAAGCTTAAGATGAAGTAC<br>AAGACACCGGAGGATTATACCGCATTTAATGGAATT<br>GAACTCTATCAGGGGAAAGTCGTTGCTTCCCTGGCGG<br>CAGGATACGTCTACGACGGGGAGTTCGCCCGCGTGG<br>AGGAAGGCAAGGTTGTGGGAGCTGCCACAAAACAGG<br>ATATTTACTCTGAGGATGATTTGAAAGTTGCCATCAT<br>CCGTGCCAATACGGATGTGAAGGTGGACGGTGAGAT<br>CTGCTATGTCTCCTGTCAGAATGTGAAGCTGACCGGA<br>AAAGACAGTGTGTCGATCCGTGACGGATATTATCTTG<br>AGACGGGAAGCGTGACGGCATCCGTGGATGTGACCG<br>GACAGGAGAGCGTCGGGACCGAGCAGCTTTCGGGAA<br>CCGAACAGATGGAGATGACCGGGGAGCCGGTGAATG<br>CGGATGATACCGAGCAGACAGAGGCGGCGGCCGGTG<br>ACGGTTCGTTCGAGACAGACGTATATACTTTCATTGT<br>CTACAAA |
| SEQ ID NO: 7<br>MLEGEESVVYVGKKGVIA<br>SLDVETLDQSYYDETELKS<br>YVDAEVEDYTAEHGKNAV<br>KVESLKVEDGVAKLKMKY<br>KTPEDYTAFNGIELYQGKV<br>VASLAAGYVYDGEFARVE<br>EGKVVGAATKQDIYSEDD<br>LKVAIIRANTDVKVDGEIC<br>YVSCQNVKLTGKDSVSIRD<br>GYYLETGSVTASVDVTGQ<br>ESVGTEQLSGTEQMEMTG<br>EPVNADDTEQTEAAAGDG<br>SFETDVYTFIVYK | SEQ ID NO: 8<br>ATGTTGGAGGGTGAAGAGTCTGTTGTCTATGTGGGTA<br>AGAAAGGTGTGATCGCGTCCCTGGACGTCGAGACTC<br>TGGACCAGTCTTACTATGATGAAACCGAGCTGAAGT<br>CGTATGTGGACGCCGAAGTTGAGGATTACACGGCCG<br>AGCACGGCAAAAATGCCGTCAAAGTTGAGAGCTTGA<br>AAGTTGAGGACGGCGTGGCAAAGCTGAAGATGAAAT<br>ACAAGACCCCAGAGGACTACACGGCGTTCAATGGTA<br>TCGAGCTGTATCAGGGCAAAGTCGTCGCATCCCTGGC<br>AGCGGGCTATGTGTACGACGGTGAGTTTGCGCGCGT<br>CGAAGAAGGCAAAGTTGTGGGTGCGGCTACGAAACA<br>AGATATCTACAGCGAAGATGACCTGAAAGTCGCGAT<br>TATTCGTGCTAACACCGATGTTAAAGTTGATGGCGAG<br>ATTTGCTACGTTAGCTGTCAAAACGTAAAGCTGACGG<br>GTAAAGATAGCGTGAGCATTCGTGATGGCTATTATCT<br>GGAAACCGGTAGCGTTACGGCGAGCGTCGATGTTAC<br>CGGTCAAGAGAGCGTGGGTACCGAACAGCTGAGCGG<br>CACCGAACAGATGGAAATGACCGGTGAACCGGTTAA<br>CGCAGACGACACGGAACAAACCGAAGCCGCGGCAG<br>GCGACGGTAGCTTCGAGACTGACGTGTACACCTTTAT<br>CGTGTACAAG |

TABLE 1-continued

| Amino Acid Sequence | Encoding Nucleic Acid Sequence |
|---|---|
| SEQ ID NO: 9<br>MDYKDDDDKGSSHMLEG<br>EESVVYVGKKGVIASLDVE<br>TLDQSYYDETELKSYVDA<br>EVEDYTAEHGKNAVKVES<br>LKVEDGVAKLKMKYKTPE<br>DYTAFNGIELYQGKVVASL<br>AAGYVYDGEFARVEEGKV<br>VGAATKQDIYSEDDLKVAI<br>IRANTDVKVDGEICYVSCQ<br>NVKLTGKDSVSIRDGYYLE<br>TGSVTASVDVTGQESVGTE<br>QLSGTEQMEMTGEPVNAD<br>DTEQTEAAAGDGSFETDV<br>YTFIVYK | SEQ ID NO: 10<br>ATGGACTACAAAGACGATGACGACAAGGGCAGCAGC<br>CATATGCTGGAGGGAGAGGAAAGTGTCGTGTACGTG<br>GGAAAGAAAGGCGTGATAGCGTCGCTGGATGTGGAG<br>ACGCTCGATCAGTCCTACTACGATGAGACGGAACTG<br>AAGTCCTATGTGGATGCAGAGGTGGAAGATTACACC<br>GCGGAGCATGGTAAAAATGCAGTCAAGGTGGAGAGC<br>CTTAAGGTGGAAGACGGTGTGGCGAAGCTTAAGATG<br>AAGTACAAGACACCGGAGGATTATACCGCATTTAAT<br>GGAATTGAACTCTATCAGGGGAAAGTCGTTGCTTCCC<br>TGGCGGCAGGATACGTCTACGACGGGGAGTTCGCCC<br>GCGTGGAGGAAGGCAAGGTTGTGGGAGCTGCCACAA<br>AACAGGATATTTACTCTGAGGATGATTTGAAAGTTGC<br>CATCATCCGTGCCAATACGGATGTGAAGGTGGACGG<br>TGAGATCTGCTATGTCTCCTGTCAGAATGTGAAGCTG<br>ACCGGAAAAGACAGTGTGTCGATCCGTGACGGATAT<br>TATCTTGAGACGGGAAGCGTGACGGCATCCGTGGAT<br>GTGACCGGACAGGAGAGCGTCGGGACCGAGCAGCTT<br>TCGGGAACCGAACAGATGGAGATGACCGGGGAGCCG<br>GTGAATGCGGATGATACCGAGCAGACAGAGGCGGCG<br>GCCGGTGACGGTTCGTTCGAGACAGACGTATATACTT<br>TCATTGTCTACAAA |
| SEQ ID NO: 19<br>MLEGEESVVYVGKKGVIA<br>SLDVETLDQSYYDETELKS<br>YVDAEVEDYTAEHGKSAV<br>KVESLKVEDGVAKLKMKY<br>KTPEDYTAFSGIELYQGKV<br>VASLAAGYVYDGEFARVE<br>EGKVVGAATKQDIYSEDD<br>LKVAIIRANTDVKVDGEIV<br>YVSSQNVKLTGKDSVSIRD<br>GYYLETGSVTASVDVTGQ<br>ESVGTEQLSGTEQMEMTG<br>EPVNADDTEQTEAAAGDG<br>SFETDYTTFIVYK | SEQ ID NO: 20<br>ATGTTGGAGGGTGAAGAGTCTGTTGTCTATGTGGGTA<br>AGAAAGGTGTGATCGCGTCCCTGGACGTCGAGACTC<br>TGGACCAGTCTTACTATGATGAAACCGAGCTGAAGT<br>CGTATGTGGACGCCGAAGTTGAGGATTACACGGCCG<br>AGCACGGCAAATCCGCCGTCAAAGTTGAGAGCTTGA<br>AAGTTGAGGACGGCGTGGCAAAGCTGAAGATGAAAT<br>ACAAGACCCCAGAGGACTACACGGCGTTCAGCGGTA<br>TCGAGCTGTATCAGGGCAAAGTCGTCGCATCCCTGGC<br>AGCGGGCTATGTGTACGACGGTGAGTTTGCGCGCGT<br>CGAAGAAGGCAAAGTTGTGGGTGCGGCTACGAAACA<br>AGATATCTACAGCGAAGATGACCTGAAAGTCGCGAT<br>TATTCGTGCTAACACCGATGTTAAAGTTGATGGCGAG<br>ATTGTGTACGTTAGCAGCCAAAACGTAAAGCTGACG<br>GGTAAAGATAGCGTGAGCATTCGTGATGGCTATTATC<br>TGGAAACCGGTAGCGTTACGGCGAGCGTCGATGTTA<br>CCGGTCAAGAGAGCGTGGGTACCGAACAGCTGAGCG<br>GCACCGAACAGATGGAAATGACCGGTGAACCGGTTA<br>ACGCAGACGACACGGAACAAACCGAAGCCGCGGCA<br>GGCGACGGTAGCTTCGAGACTGACGTGTACACCTTTA<br>TCGTGTACAAG |

Epithelial Barrier Function in Disease

Studies in recent years have identified a major role of both genetic and environmental factors in the pathogenesis of IBD. Markus Neurath, "Cytokines in Inflammatory Bowel Disease," Nature Reviews Immunology, Vol. 14, 329-342 (2014). A combination of these IBD risk factors seems to initiate detrimental changes in epithelial barrier function, thereby allowing the translocation of luminal antigens (for example, bacterial antigens from the commensal microbiota) into the bowel wall. Id. Subsequently, aberrant and excessive responses, such as increased pro-inflammatory cytokine release, to such environmental triggers cause subclinical or acute mucosal inflammation in a genetically susceptible host. Id. Thus, the importance of proper epithelial barrier function in IBD is apparent, for in subjects that fail to resolve acute intestinal inflammation, chronic intestinal inflammation develops that is induced by the uncontrolled activation of the mucosal immune system. In particular, mucosal immune cells, such as macrophages, T cells, and the subsets of innate lymphoid cells (ILCs), seem to respond to microbial products or antigens from the commensal microbiota by, e.g., producing cytokines that can promote chronic inflammation of the gastrointestinal tract. Consequently, restoring proper epithelial barrier function to patients may be critical in resolving IBD.

The therapeutic activity of SG-11 was identified in part by its beneficial effects on epithelial barrier function both in vitro and in vivo. As shown in Example 2, SG-11 was active in increasing epithelial barrier integrity as shown by an in vitro trans-epithelial electrical resistance (TEER) assay. TEER assays are well-known methods for measuring effects on the structural and functional integrity of an epithelial cell layer (Srinivasan et al., 2015, J Lab Autom, 20:107-126; Beduneau et al., 2014, Eur J Pharm Biopharm, 87:290-298; Zolotarevsky et al., 2002, Gastroenterology, 123:163-172; Dewi, et al. (2004) J. Virol. Methods. 121:171-180, and in Mandic, et al. (2004) Clin. Exp. Metast. 21:699-704.). The assay performed and described herein consists of an epithelial monolayer made up of enterocyte and goblets cells to more accurately model the structural and functional components of the intestinal epithelium. The cells are cultured until tight junction formation occurs and barrier function capacity is assessed by a measurement of trans-epithelial electrical resistance. Upon addition of an insult, such as heat killed E. coli, there is a decrease in electrical resistance across the epithelial layer. Control reagents useful in the TEER assay include staurosporine and a myosin light chain kinase inhibitor. Staurosporine is a broad spectrum kinase inhibitor, originating from Streptomyces staurosporeus, which induces apoptosis. This reagent disrupts about 98% of the gap junctions leading to a decrease in electrical resistance in a TEER assay. Myosin light chain kinase (MLCK) is the terminal effector in a signaling cascade induced by pro-inflammatory cytokines, which results in contraction of the perijunctional actomyosin ring, resulting in separation of the gap junctions. By inhibiting MLCK, disruption of tight junctions is prevented. MLCK inhibitor in a TEER assay should reduce or prevent the reduction of electrical resistance in a TEER assay.

In some embodiments, the SG-11 protein or variant or fragment thereof as described herein can be characterized by its ability to increase epithelial barrier function integrity as assessed by an in vitro TEER assay. The SG-11 protein or variant or fragment thereof may increase electrical resistance in a TEER assay by at least about 10%, 20%, 30%, 40%, 50%, 60%, 70%, 80% or 90% as compared to the TEER assay performed in the absence of the protein.

In addition, Example 6 shows that SG-11 protein can enhance or facilitate epithelial wound healing, an activity that can play a role in the maintenance or repair of and epithelial barrier such as an intestinal or mucosal epithelial barrier.

In view of the effect of SG-11 to repair barrier function integrity in vitro, SG-11 was analyzed in vivo for its ability to reduce damage in a rodent model of IBD. Examples 7 and 8 (SG-11) and 16 (SG-11 variant) describe studies done using a DSS (dextran sodium sulfate) animal model, a model well accepted for the study of agents on IBDs (Chassaign et al., 2014, Curr Protoc Imunol, 104:Unit-15.25; Kiesler et al., 2015, Cell Mol Gastroenterol Hepatol). DSS is a sulfated polysaccharide that is directly toxic to colonic epithelium and causes epithelial cell injury leading to loss of barrier function due to disrupted gap junctions. In these experiments, animals were treated with SG-11 either prior to (Example 7) or after (Example 8) induction of colitis in the mouse. As a positive control, the mice were also treated with Gly2-GLP2, a stable analog of glucagon-like peptide 2 (GLP2). Gly2-GLP2 is known to promote epithelial cell growth and reduce colonic injury in experiment mouse colitis models. Results of the DSS studies show that SG-11 protein was effective in reducing weight loss in the DSS models, an important indicator of clinical efficacy for IBD therapeutics. SG-11 treatment also reduced scores in gross pathology and intestinal histopathology analyses.

It is noted that while SG-11 treatment improved the 4Kda-FITC intestinal permeability readout and reduced serum levels of LPS binding protein (LBP—a marker of LPS exposure) in Example 7, no significant effects upon treatment with SG-11 or Gly2-GLP2 were observed in Example 8. This is not surprising when considering that animals in Example 8 were treated with DSS for 7 days prior to replacement with normal drinking water and treatment with SG-11 or Gly2-GLP2. This prior exposure to DSS results in damage to the intestinal epithelium, translocation of LPS across a disrupted epithelial barrier, and induction of LBP secretion. However, based on 4KDa-FITC dextran measurements, epithelial barrier repair appears to occur rapidly, within 3-4 days, following replacement of DSS with normal drinking water (data not shown, FIG. 12). Accordingly, it is difficult to detect improvements in 4KDa-FITC permeability readouts in treated vs. untreated animals at the time of measurement (after 6 days of treatment). Additionally, levels of LBP in the serum may be independent of barrier function repair in animals exposed to DSS for an extended period of time prior to therapeutic treatment (Example 8). For instance, hepatocytes activated by translocating LPS during the DSS exposure produce and secrete large amounts of LPB. Accordingly, and without being bound by theory, the short time period of the study may not allow sufficient time for inactivation of the hepatocytes and clearance of LBP from the serum of the DSS-treated animals. It is considered, therefore, that continuation of the study with measurement of serum LBP at later time points would show a decrease in serum LBP levels, however, the decrease in serum LBP may be similar in both treated and untreated animals if barrier function is restored in both animals before LBP can be cleared from the serum.

Variants of SG-11

In view of the therapeutic value of SG-11 and its use for treating disease, the protein was further characterized and its sequence modified to change its primary structure in ways that would optimize pharmaceutical formulation and long-term storage of the protein.

As described in Example 9, SEQ ID NO:7 was used to perform a BLAST search the GenBank non-redundant protein database in order to identify proteins with similar amino acid sequences and which may be functional homologs or have function(s) similar to those of SG-11. Three such proteins were identified and the predicted mature sequence of each (without an N-terminal signal peptide) was aligned with SEQ ID NO:7 to identify regions and individual positions within the proteins which were relatively conserved. These 3 proteins are disclosed herein as SEQ ID NO:21 (derived from GenBank Acc. No. WP_006857001), SEQ ID NO:22 (derived from GenBank Acc. No. WP_075679733), and SEQ ID NO:23 (derived from GenBank Acc. No. WP_055301040) (FIG. 17) and accordingly, provided herein are pharmaceutical compositions comprising 1 of these 3 proteins or variant or fragment thereof, as well as methods for treating diseases associated with barrier function disorders and/or gastrointestinal diseases or disorders comprising administering to a subject in need thereof a pharmaceutical composition comprising any one of SEQ ID NO:21, SEQ ID NO:22 and SEQ ID NO:23 or variant or fragment thereof.

An exemplary embodiment of SG-11 variants, SG-11V5 amino acid sequence and an encoding nucleic acid sequence is provided in Table 2 below.

TABLE 2

| Amino Acid Sequence | Encoding Nucleic Acid Sequence |
|---|---|
| SEQ ID NO: 19 (SG-11V5) | SEQ ID NO: 20 |
| MLEGEESVVYVGKKGVIA | ATGTTGGAGGGTGAAGAGTCTGTTGTCTATGTGGGTA |
| SLDVETLDQSYYDETELKS | AGAAAGGTGTGATCGCGTCCCTGGACGTCGAGACTC |
| YVDAEVEDYTAEHGKSAV | TGGACCAGTCTTACTATGATGAAACCGAGCTGAAGT |
| KVESLKVEDGVAKLKMKY | CGTATGTGGACGCCGAAGTTGAGGATTACACGGCCG |
| KTPEDYTAFSGIELYQGKV | AGCACGGCAAATCCGCCGTCAAAGTTGAGAGCTTGA |
| VASLAAGYVYDGEFARVE | AAGTTGAGGACGGCGTGGCAAAGCTGAAGATGAAAT |
| EGKVVGAATKQDIYSEDD | ACAAGACCCCAGAGGACTACACGGCGTTCAGCGGTA |
| LKVAIIRANTDVKVDGEIV | TCGAGCTGTATCAGGGCAAAGTCGTCGCATCCCTGGC |
| YVSSQNVKLTGKDSVSIRD | AGCGGGCTATGTGTACGACGGTGAGTTTGCGCGCGT |

TABLE 2-continued

| Amino Acid Sequence | Encoding Nucleic Acid Sequence |
|---|---|
| GYYLETGSVTASVDVTGQ<br>ESVGTEQLSGTEQMEMTG<br>EPVNADDTEQTEAAAGDG<br>SFETDVYTFIVYK | CGAAGAAGGCAAAGTTGTGGGTGCGGCTACGAAACA<br>AGATATCTACAGCGAAGATGACCTGAAAGTCGCGAT<br>TATTCGTGCTAACACCGATGTTAAAGTTGATGGCGAG<br>ATTGTGTACGTTAGCAGCCAAAACGTAAAGCTGACG<br>GGTAAAGATAGCGTGAGCATTCGTGATGGCTATTATC<br>TGGAAACCGGTAGCGTTACGGCGAGCGTCGATGTTA<br>CCGGTCAAGAGAGCGTGGGTACCGAACAGCTGAGCG<br>GCACCGAACAGATGGAAATGACCGGTGAACCGGTTA<br>ACGCAGACGACACGGAACAAACCGAAGCCGCGGCA<br>GGCGACGGTAGCTTCGAGACTGACGTGTACACCTTTA<br>TCGTGTACAAG |

Figure 23A:
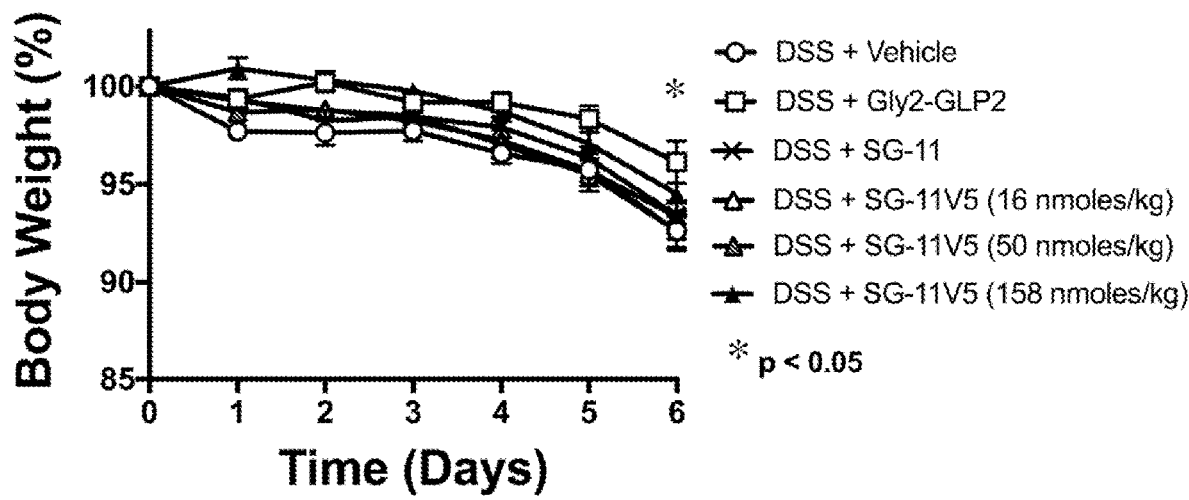
FIG. 23A and FIG. 23B show effects of treatment with SG-11 or a variant of SG-11 on weight loss in a DSS model of inflammatory bowel disease, as described in Example 16.
Figure 23B:
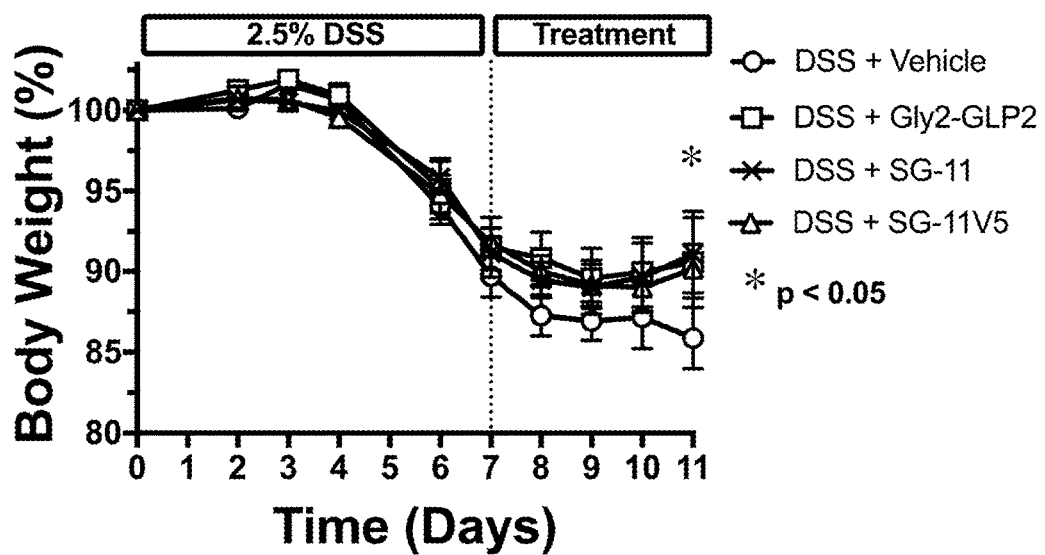
Figure 24:
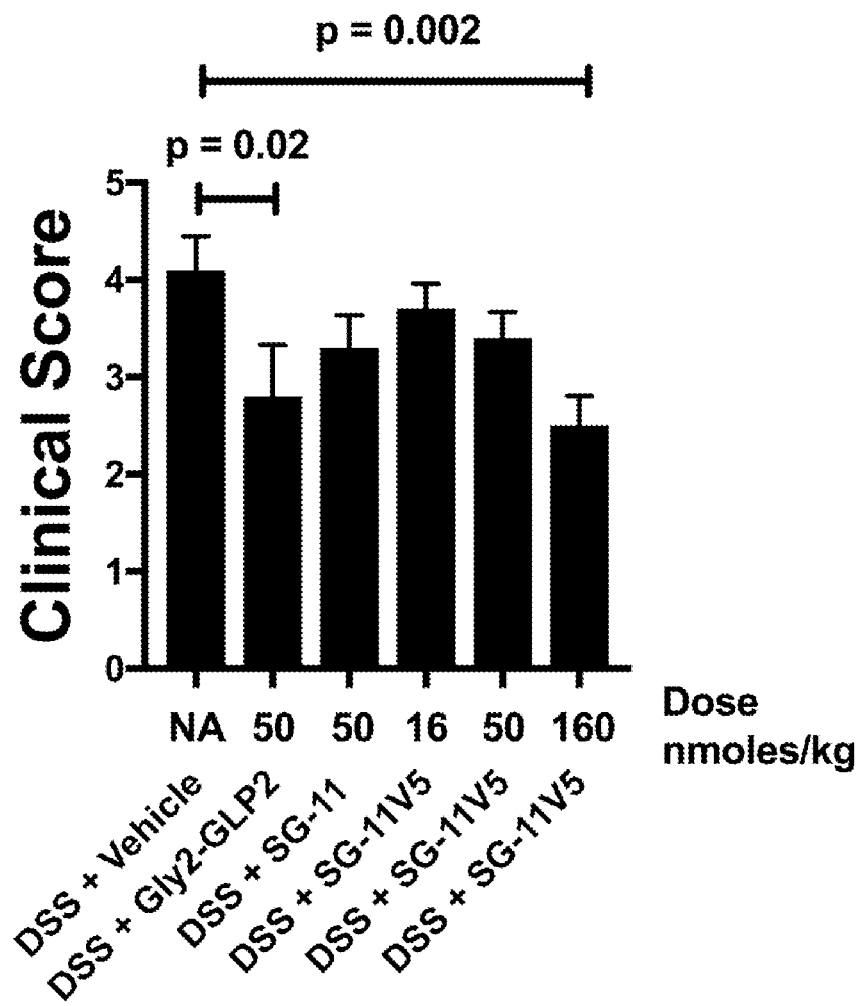
FIG. 24 shows effects of administering SG-11 or a variant of SG-11 on gross pathology in a DSS model of inflammatory bowel disease, as described in Example 16.

In the interest of enhancing the stability of SG-11 proteins for use in pharmaceutical formulations and clinical applications, studies were performed to identify and characterize post translational modifications (PTMs) of purified SG-11 protein. These experiments are described in Examples 10-11. Such analysis shows that the SG-11 protein can undergo at least the PTMs of methionine oxidation, and asparagine deamidation. Moreover, experiments described in Example 12 the cysteines in SG-11 are unlikely to form disulfide bonds in the purified, functional conformation of the active protein, suggesting that the free sulfhydryl groups in SG-11 may cause aggregation in a solution containing the purified protein. Based on these stability studies and despite the conserved nature of the residues in SG-11 as seen in the multiple sequence alignment (FIG. 17) it was decided to test whether or not the cysteines at positions 147 and/or 151 (with reference to SEQ ID NO:7) could be substituted with a different amino acid. Also, substitution of conserved asparagines at positions 53 and 83 were considered. In an exemplary embodiment, the SG-11 sequence of SEQ ID NO:7 is modified to introduce the substitutions of C147V and C151S to generate SEQ ID NO:11 (SG-11V1). The C147V and C151S substitutions are also present in the provided SG-11 variants SG-11V2 (SEQ ID NO:13; comprising G84D, C147V, C151S), SG-11V3 (SEQ ID NO:15; comprising N83S, C147V, C151S), SG-11V4 (SEQ ID NO:17; comprising N53S, G84D, C147V, C151S) and SG-11V5 (SEQ ID NO:19; comprising N53S, N83S, C147V, C151S).

Example 13 shows that PTMs (methionine oxidation and asparagine deamidation) is significantly reduced in SG-11V5 as compared to SG-11 (SEQ ID NO:7). The reductions were observed both at different temperatures and in different storage buffers. Example 14 describes an experiment performed to determine if an SG-11 variant comprising the cysteine substitutions (SG-11V5, SEQ ID NO:19) would affect aggregation of the protein in a storage buffer. The results show that the SG-11V5 variant has reduced aggregation compared to SG-11 (SEQ ID NO:7) when tested in different storage buffers.

Notably, although the amino acids substituted to generate SG-11V5 are present in a relatively conserved region of the SG-11 protein, it was possible to substitute these 4 residues without losing functional activity (Examples 15 and 16, described in more detail below).

Based on the experimental data and analysis described herein, contemplated are variants of SG-11 (e.g., SEQ ID NO:3 or SEQ ID NO:5) were designed to substitute any one or more of amino acids N53, N83, G84, C147 and C151 of SEQ ID NO:7 (wherein noted substitutions are at residue positions with respect to SEQ ID NO:7). An embodiment of this variant is provided below in Table 3, as SEQ ID NO:33, wherein the residue at each of positions 53, 83, 84, 147 and 151 is denoted as X indicating that one or more of these 5 residues can each be substituted for any possible 20 amino acids. In some embodiments, the protein comprises the amino acid sequence of SEQ ID NO:33. In other embodiments, X53 is N, S, T, M, R, Q and/or X83 is N, R or K, and/or X84 is G or A, and/or X147 is C, S, T, M, V, L, A, or G, and/or X151 is C, S, T, M, V, L, A, or G. In still other embodiments, X53 is N, S or K and/or X83 is N or R and/or X84 is G or A and/or X147 is C, V, L or A and/or X151 is C, S, V, L or A.

In some embodiments, the protein comprises the amino acid sequence of SEQ ID NO:34, wherein X53 is any amino acid other than N, X83 is any amino acid other than N, X84 is any amino acid other than G, X147 is any amino acid other than C, and/or X151 is any amino acid other than C.

TABLE 3

| Amino Acid Sequence for SEQ ID NO: 33 and SEQ ID NO: 34 (See definitions above) |
|---|
| MLEGEESVVYVGKKGVIASLDVETLDQSYYDETELKSYVDAEVEDYTAE<br>HGKXAVKVESLKVEDGVAKLKMKYKTPEDYTAFXXIELYQGKVVASLAA<br>GYVYDGEFARVEEGKVVGAATKQDIYSEDDLKVAIIRANTDVKVDGEIX<br>YVSXQNVKLTGKDSVSIRDGYYLETGSVTASVDVTGQESVGTEQLSGTE<br>QMEMTGEPVNADDTEQTEAAAGDGSFETDVYTFIVYK |

In another example, certain amino acids of the taught proteins may be substituted for other amino acids in a protein structure without appreciable loss of interactive binding capacity with structures such as, for example, binding sites on substrate molecules, receptors, antigen-binding regions of antibodies, and the like. Thus, these proteins would be biologically functional equivalents of the disclosed proteins (e.g. comprising SEQ ID NO:3 or variants thereof). So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the present disclosure.

Also provided herein are variants of SG-11: SEQ ID NO:11 (C147V, C151S, "SG11-V1"), SEQ ID NO:13 (G84D, C147V, C151S "SG11-V2"), SEQ ID NO:15 (N83S, C147V, C151S "SG11-V3"), SEQ ID NO:17 (N53S, G84D, C147V, C151S "SG11-V4"), and SEQ ID NO:19 (N53S, N83S, C147V, C151S "SG11-V5").

Importantly, the SG-11 variant protein comprising SEQ ID NO:19 maintained its activity both with respect to the TEER assay (Example 15) and in vivo DSS mouse models (Example 16), showing that variants of SG-11 can maintain therapeutic function equivalent to that of wild type SG-11. Specifically, in vitro TEER and in vivo DSS model experiments were performed in which SG-11 (SEQ ID NO:7) and SG-11V5 (SEQ ID NO:19) were used in parallel. Example 15 shows that SG-11 and SG-11V5 has essentially the same functional ability to reduce TEER in vitro. As described in Examples 7 and 8 in which DSS model mice were treated with SG-11 before or after DSS treatment, Example 16 was performed to compare in vivo efficacy of SG-11 and the SG-11 variant Example 16 also compares administration to the mice with the protein before DSS (described as Example 16A) and after DSS (described as Example 16B) treatment. SG-11 and the SG-11 variant reduced weight loss (FIGS. 23A and 23B) as well as gross pathology clinical scores (FIG. 24). Again, SG-11 reduced intestinal permeability and serum LBP levels while SG-11V5 is shown to reduce intestinal permeability and serum LBP levels in a dose-dependent manner (FIG. 21A and FIG. 22A) in Example 16A. Similar to results observed in Examples 7 and 8, SG-11 and the SG-11 variant protein did not reduce intestinal permeability or serum LBP levels in Example 16B where the therapeutic protein was administered after a prolonged assault with DSS and results observed over a limited period of time. As discussed above, it is considered that continuation of the study would show a decrease in both permeability and serum LBP levels.

In view of these data provided herein is a therapeutic protein is at least 90%, 95%, 96%, 97%, 98%, 99% or 100% identical to a protein comprising the amino acid sequence of SEQ ID NO:3 or a fragment thereof. In an alternative embodiment, the therapeutic protein has at least 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100% sequence identity to SEQ ID NO:19 or to SEQ ID NO:7 or a fragment thereof. In some embodiments, the therapeutic protein comprises an amino acid sequence that is identical to SEQ ID NO:19 or SEQ ID NO:5. The therapeutic protein alternatively can be one which is a variant of SEQ ID NO:3 or SEQ ID NO:7, wherein the therapeutic protein has 1, 2, 3, 4, 5, 6, 7, 8, 9 or 10 amino acid substitutions relative to SEQ ID NO:7. In some embodiments, the variant therapeutic protein comprises a non-naturally occurring variant of SEQ ID NO:3. Alternatively stated, the therapeutic protein comprises 1, 2, 3, 4, 5, 6, 7, 8, 9 or 10 non-naturally occurring amino acid substitutions relative to SEQ ID NO:3. In some embodiments, the therapeutic protein does not comprise an amino acid sequence identical to the sequence of residues 2 to 233 of SEQ ID NO:7.

In some embodiments, the SG-11 protein can be modified or varied by one or more amino acid insertions or deletions. An insertion can be the addition of 1 or more (e.g., 1, 2, 3, 4, 5, 6, 7, 8, 9 or 1 to 10, 1 to 20, 1 to 30, 1 to 40 or 1 to 50) amino acids to the N-terminus and/or C-terminus of the protein and/or can be an insert of 1 or more (e.g., 1, 2, 3, 4, 5, 6, 7, 8, 9 or 1 to 10, 1 to 20, 1 to 30, 1 to 40 or 1 to 50) amino acids at a position located between the N- and C-terminal amino acids. Similarly, the deletion of the 1 or more (e.g., 1, 2, 3, 4, 5, 6, 7, 8, 9 or 1 to 10, 1 to 20, 1 to 30, 1 to 40 or 1 to 50) amino acids can occur at any of the N- and C-terminus and in the internal portion.

In some embodiments, a modified or variant protein is provided which contains at least one non-naturally occurring amino acid substitution relative to SEQ ID NO:3. In other embodiments, the variant protein comprises 1, 2, 3, 4, 5, 6, 7, 8, 9 or 10 amino acid substitutions relative to SEQ ID NO:3 or SEQ ID NO:7. In further embodiments, the modified protein contains the amino acid sequence as depicted in SEQ ID NO:5, SEQ ID NO:7, SEQ ID NO:9, SEQ ID NO:11 (SG-11V1), SEQ ID NO:13 (SG-11V2), SEQ ID NO:15 (SG-11V3), SEQ ID NO:17 (SG-11V4), or SEQ ID NO:19 (SG-11V5).

In some embodiments, a therapeutic protein according to the present disclosure encompasses any one of the variant proteins (e.g., SEQ ID NO:11, SEQ ID NO:13, SEQ ID NO:15, SEQ ID NO:17; or SEQ ID NO:19) that also retains one or more activities of the full length mature protein depicted in, for example, SEQ ID NO:3 or SEQ ID NO:7.

Also envisioned are polynucleotide sequences which encodes these proteins. It is well known to the ordinarily skilled artisan that 2 polynucleotide sequences which encode a single polypeptide sequence can share relatively low sequence identity due to the degenerative nature of the genetic code. For example, if every codon in the polynucleotide encoding a 233-amino acid sequence contained at least 1 substitution in its third position, that would calculate to about 67% sequence identity between the 2 polynucleotides. A polynucleotide of the present disclosure comprises a sequence that encodes a protein that is at least 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100% identical to SEQ ID NO:19. Accordingly, in some embodiments, the polynucleotide comprises a sequence that is at least 67% identical to SEQ ID NO:4 or SEQ ID NO:8, or is about 67% to 100%, 70% to 100%, 75% to 100%, 80% to 100%, 90% to 100% or 95% to 100% identical to SEQ ID NO:20 or a fragment thereof. In some embodiments, the polynucleotide comprises the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or a fragment thereof.

In some embodiments, the taught proteins have markedly different structural and/or functional characteristics, as compared to a protein comprising or consisting of SEQ ID NO:3.

The term "SG-11 variant" as used herein can include SG-11 proteins that are, e.g., identical to not identical to a protein comprising the sequence of SEQ ID NO:3 and which are further modified such as by a PTM or fusion or linkage to a second agent, e.g., a protein or peptide.

Protein PTMs occur in vivo and can increase the functional diversity of the proteome by the covalent addition of functional groups or proteins, proteolytic cleavage of regulatory subunits or degradation of entire proteins. Isolated proteins prepared according to the present disclosure can undergo 1 or more PTMs in vivo or in vitro. The type of modification(s) depends on host cell in which the protein is expressed and includes but is not limited to phosphorylation, glycosylation, ubiquitination, nitrosylation (e.g., S-nitrosylation), methylation, acetylation (e.g., N-acetylation), lipidation (myristoylation, N-myristoylation, S-palmitoylation, farnesylation, S-prenylation, S-palmitoylation) and proteolysis may influence almost all aspects of normal cell biology and pathogenesis. The isolated and/or purified SG-11 proteins or variants or fragments thereof as disclosed herein may comprise one or more the above recited post-translational modifications.

The SG-11 protein or variant or fragment thereof may be a fusion protein in which the N- and/or C-terminal domain is fused to a second protein via a peptide bond. Commonly used fusion partners well known to the ordinarily skilled artisan include but are not limited to human serum albumin and the crystallizable fragment, or constant domain of IgG, Fc. In some embodiments, the SG-11 protein or variant or fragment thereof is linked to a second protein or peptide via a disulfide bond, wherein the second protein or peptide comprises a cysteine residue.

As aforementioned, modifications and/or changes (e.g., substitutions, insertions, deletions) may be made in the structure of proteins disclosed herein. Thus, the present disclosure contemplates variation in sequence of these proteins, and nucleic acids coding therefore, where they are nonetheless able to retain substantial activity with respect to the functional activities assessed in various in vitro and in vivo assays as well as in therapeutic aspects of the present disclosure. In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity.

It is also contemplated that the SG-11 protein or variant or fragment thereof is one which, when administered to a subject, can reduce disease-associated weight loss, improve the clinical pathology score, and/or minimize colon shortening in the subject. In some embodiments, the subject is a mammal which has genetically or clinically induced inflammatory disorder or dysfunctional epithelial barrier function. Alternatively, the animal has an idiopathic gastrointestinal disorder involving a decrease in epithelial barrier function or intestinal inflammatory disorder. In other embodiments, the mammal is a human, non-human primate, or a rodent. The rodent may be a mouse or rat.

In some embodiments, the SG-11 protein or variant or fragment thereof according to the present disclosure is one which can modulate production of and/or secretion of a cytokine in an in vitro assay or in an subject administered the protein. In some embodiments, secretion of cytokines is reduced in vitro. Levels of cytokines produced and/or secreted in an in vitro assay or subject administered the protein are likely to be measured in the blood, serum, and/or plasma of the subject. Administration of the protein may result in a decrease in the serum levels of a pro-inflammatory cytokine such as one or more of TNF-α, IL-17, IL-1β, IL-2, IFN-γ, IL-6, IL-12, IL-25, IL-33, IL-8, MCP-1, MIP-3α, CXCL1, and IL-23. Alternatively, the cytokine may be an anti-inflammatory cytokine, in which case administration of the protein results in an increase in serum levels of an anti-inflammatory cytokine such as IL-4, IL-10, IL-13, IFN-α, and TGF-β.

In some embodiments, the SG-11 protein or variant or fragment thereof has the functional ability to reduce gastrointestinal inflammation when administered to a subject such as a mammal (e.g., rodent, non human primate, or human). In other embodiments, the protein has the functional ability to reduce inflammatory (i.e. pro-inflammatory) cytokines, when administered to the subject. In yet other embodiments, the protein is able to reduce TNF-α and/or IL-23, when administered to the subject. In still other embodiments, the protein has the functional ability to increase anti-inflammatory cytokines, when administered to the subject. In some aspects, a protein of the disclosure is able to increase IL-10, when administered to the subject.

A SG-11 protein or variant or fragment thereof according to the present disclosure is one which, when administered to a subject (e.g., rodent, non human primate, or human), can improve gastrointestinal epithelial cell barrier function, reduce disease-associated weight loss, improve clinical scores, improve colon length and/or colon weight-to-length readouts, induce or increase mucin gene expression (e.g., muc2 expression), increase the structural integrity and/or functionality of a gastrointestinal mucous barrier (e.g., in the small intestine, large intestine, mouth and/or esophagus), and/or reduce inflammation in the gastrointestinal tract.

In some embodiments, the SG-11 protein or variant or fragment thereof resulting from such a substitution, insertion and/or deletion of amino acids relative to SEQ ID NO:3 or SEQ ID NO:7 maintains a level of functional activity which is substantially the same as that of a protein of SEQ ID NO:7 or SEQ ID NO:19 (e.g., is able to increase electrical resistance in a TEER assay wherein an epithelial cell layer was disrupted by, e.g., heat-killed E. coli). The variant protein may be useful as a therapeutic for treatment or prevention of a variety of conditions, including, but not limited to inflammatory conditions and/or barrier function disorders, including, but not limited to, inflammation of the gastrointestinal (including oral, esophageal, and intestinal) mucosa, impaired intestinal epithelial cell gap junction integrity. In some embodiments, the modified protein has one or more of the following effects when administered to an individual suffering from, or predisposed to, an inflammatory condition and/or barrier function disorder: improvement of epithelial barrier integrity, e.g., following inflammation induced disruption; suppression of production of at least one pro-inflammatory cytokine (e.g., TNF-α and/or IL-23) by one or more immune cell(s); induction of mucin production in epithelial cells; and/or improvement of epithelial wound healing. Moreover, the modified or variant SG-11 protein may be used for treatment or prevention of a disorder or condition such as, but not limited to, inflammatory bowel disease, ulcerative colitis, Crohn's disease, short bowel syndrome, GI mucositis, oral mucositis, chemotherapy-induced mucositis, radiation-induced mucositis, necrotizing enterocolitis, pouchitis, a metabolic disease, celiac disease, inflammatory bowel syndrome, or chemotherapy associated steatohepatitis (CASH).

As demonstrated, e.g., in Example 6, the SG-11 protein can enhance epithelial wound healing. Accordingly, provided herein is a therapeutic protein comprising the amino acid sequence of SEQ ID NO:3 or SEQ ID NO:7 or a variant or fragment thereof, wherein the protein can increase wound healing in an in vitro assay.

Methods of Treatment

The SG-11 proteins described herein including variants (e.g., amino acid substitutions, deletions, insertions), modifications (e.g., glycosylation, acetylation), SG-11 fragments and fusions thereof are contemplated for use in treating a subject diagnosed with or suffering from a disorder related to inflammation within the gastrointestinal tract and/or malfunction of epithelial barrier function within the gastrointestinal tract.

Provided herein are methods for treating a subject in need thereof comprising administering to the subject a pharmaceutical composition comprising a SG-11 protein or fragment or variant thereof as described in the present disclosure. The subject can be one who has been diagnosed with inflammatory bowel disease, ulcerative colitis, pediatric UC, Crohn's disease, pediatric Crohn's disease, short bowel syndrome, mucositis GI mucositis, oral mucositis, mucositis of the esophagus, stomach, small intestine (duodenum, jejunum, ileum), large intestine (colon), and/or rectum, chemotherapy-induced mucositis, radiation-induced mucositis, necrotizing enterocolitis, pouchitis, a metabolic disease, celiac disease, irritable bowel syndrome, or chemotherapy associated steatohepatitis (CASH). Administration of the SG-11 pharmaceutical compositions described herein may also be useful for wound healing applications.

Inflammatory Bowel Disease

Inflammatory bowel disease (IBD) classically includes ulcerative colitis (UC) and Crohn's disease (CD). The pathogenesis of inflammatory bowel disease is not known. A genetic predisposition has been suggested, and a host of environmental factors, including bacterial, viral and, perhaps, dietary antigens, can trigger an ongoing enteric inflammatory cascade. Id. IBD can cause severe diarrhea, pain, fatigue, and weight loss. IBD can be debilitating and sometimes leads to life-threatening complications. Accordingly, in some embodiments, the method of treatment as described herein is effective to reduce, prevent or eliminate any one or more of the symptoms described above wherein the method comprises administering to a patient in need thereof a therapeutically effective amount of a pharmaceutical composition comprising the SG-11 protein or variant or fragment thereof. In some embodiments, the method of treatment results in remission.

Ulcerative Colitis

Ulcerative colitis is an inflammatory bowel disease that causes long-lasting inflammation and sores (ulcers), in the innermost lining of your large intestine (colon) and rectum.

Ulcerative colitis typically presents with shallow, continuous inflammation extending from the rectum proximally to include, in many patients, the entire colon. Fistulas, fissures, abscesses and small-bowel involvement are absent. Patients with limited disease (e.g., proctitis) typically have mild but frequently recurrent symptoms, while patients with pancolitis more commonly have severe symptoms, often requiring hospitalization. Botoman et al., "Management of Inflammatory Bowel Disease," Am. Fam. Physician, Vol. 57(1):57-68 (Jan. 1, 1998) (internal citations omitted). Thus, ulcerative colitis is an IBD that causes long-lasting inflammation and sores (ulcers) in the innermost lining of your large intestine (colon) and rectum.

Crohn's Disease

Unlike ulcerative colitis, Crohn's disease can involve the entire intestinal tract, from the mouth to the anus, with discontinuous focal ulceration, fistula formation and perianal involvement. The terminal ileum is most commonly affected, usually with variable degrees of colonic involvement. Subsets of patients have perianal disease with fissures and fistula formation. Only 2 to 3 percent of patients with Crohn's disease have clinically significant involvement of the upper gastrointestinal tract. Botoman et al., "Management of Inflammatory Bowel Disease," Am. Fam. Physician, Vol. 57(1):57-68 (Jan. 1, 1998) (internal citations omitted). Thus, Crohn's disease is an IBD that causes inflammation of the lining of your digestive tract. In Crohn's disease, inflammation often spreads deep into affected tissues. The inflammation can involve different areas of the digestive tract, i.e. the large intestine, small intestine, or both. Collagenous colitis and lymphocytic colitis also are considered inflammatory bowel diseases, but are usually regarded separately from classic inflammatory bowel disease.

Clinical Parameters of Inflammatory Bowel Disease

As previously discussed, inflammatory bowel disease encompasses ulcerative colitis and Crohn's disease. There are numerous scores and clinical markers known to one of skill in the art that can be utilized to access the efficacy of the administered proteins described herein in treating these conditions.

There are two general approaches to evaluating patients with IBD. The first involves the visual examination of the mucosa and relies on the observation of signs of damage to the mucosa, in view of the fact that IBD is manifested by the appearance of inflammation and ulcers in the GI tract. Any procedure that allows an assessment of the mucosa can be used. Examples include barium enemas, x-rays, and endoscopy. An endoscopy may be of the esophagus, stomach and duodenum (esophagogastroduodenoscopy), small intestine (enteroscopy), or large intestine/colon (colonoscopy, sigmoidoscopy). These techniques are used to identify areas of inflammation, ulcers and abnormal growths such as polyps.

Scoring systems based on this visual examination of the GI tract exist to determine the status and severity of IBD, and these scoring systems are intended to ensure that uniform assessment of different patients occurs, despite the fact that patients may be assessed by different medical professionals, in diagnosis and monitoring of these diseases as well as in clinical research evaluations. Examples of evaluations based on visual examination of UC are discussed and compared in Dapemo M et al (J Crohns Colitis. 2011 5:484-98).

Clinical scoring systems also exist, with the same purpose. The findings on endoscopy or other examination of the mucosa can be incorporated into these clinical scoring systems, but these scoring systems also incorporate data based on symptoms such as stool frequency, rectal bleeding and physician's global assessment. IBD has a variety of symptoms that affect quality of life, so certain of these scoring systems also take into account a quantitative assessment of the effect on quality of life as well as the quantification of symptoms.

One example of a scoring system for UC is the Mayo scoring system (Schroeder et al., N Eng J Med, 1987, 317:1625-1629), but others exist that have less commonly been used and include the Ulcerative Colitis Endoscopic Index of Severity (UCEIS) score (Travis et al, 2012, Gut, 61:535-542), Baron Score (Baron et al., 1964, BMJ, 1:89), Ulcerative Colitis Colonoscopic Index of Severity (UCCIS) (Thia et al., 2011, Inflamm Bowel Dis, 17:1757-1764), Rachmilewitz Endoscopic Index (Rachmilewitz, 1989, BMJ, 298:82-86), Sutherland Index (also known as the UC Disease Activity Index (UCDAI) scoring system; Sutherland et al., 1987, Gastroenterology, 92:1994-1998), Matts Score (Matts, 1961, QJM, 30:393-407), and Blackstone Index (Blackstone, 1984, Inflammatory bowel disease. In: Blackstone M O (ed.) Endoscopic interpretation: normal and pathologic appearances of the gastrointestinal tract, 1984, pp. 464-494). For a review, see Paine, 2014, Gastroenterol Rep 2:161-168. Accordingly, also contemplated herein is a method for treating a subject diagnosed with and suffering from UC, wherein the treatment comprises administering a SG-11 protein or variant or fragment thereof as described herein and wherein the treatment results in a decrease in the UC pathology as determined by measurement of the UCEIS score, the Baron score, the UCCIS score, the Rachmilewitz Endoscopic Index, the Sutherland Index, and/or the Blackstone Index.

An example of a scoring system for CD is the Crohn's Disease Activity Index (CDAI) (Sands B et al 2004, N Engl J Med 350 (9): 876-85); most major studies use the CDAI in order to define response or remission of disease. Calculation of the CDAI score includes scoring of the number of liquid stools over 7 days, instances and severity of abdominal pain over 7 days, general well-being over 7 days, extraintestinal complications (e.g., arthritis/arthralgia, iritis/uveitis, erythema nodosum, pyoderma gangrenosum, aphtous stomatitis, anal fissure/fistula/abscess, and/or fever >37.8° C.), use of antidiarrheal drugs over 7 days, present of abdominal mass, hematocrit, and body weight as a ratio of ideal/observed or percentage deviation from standard weight. Based on the CDAI score, the CD is classified as either asymptomatic remission (0 to 149 points), mildly to moderately active CD (150 to 220 points), moderately to severely active CD (221 to 450 points), or severely active fulminant disease (451 to 1000 points). In some embodiments, the method of treatment comprising administering to a patient diagnosed with CD a therapeutically effective amount of SG-11 protein or variant or fragment thereof results in a decrease in a diagnostic score of CD. For example, the score may change the diagnosis from severely active to mildly or moderately active or to asymptomatic remission.

The Harvey-Bradshaw index is a simpler version of the CDAI which consists of only clinical parameters (Harvey et al., 1980, Lancet 1(8178):1134-1135). The impact on quality of life is also addressed by the Inflammatory Bowel Disease Questionnaire (IBDQ) (Irvine et al., 1994, Gastroenterology 106: 287-296). Alternative methods further include CDEIS and SES CD (see, e.g., Levesque, et al. (2015) Gastroentrol. 148:37 57).

In some embodiments, a method of treating an IBD, e.g., UC, is provided wherein the treatment is effective in reducing the Mayo Score. The Mayo Score is a combined endoscopic and clinical scale used to assess the severity of UC and has a scale of 1-12 The Mayo Score is a composite of subscores for stool frequency, rectal bleeding, findings of flexible proctosigmoidoscopy or colonoscopy, and physician's global assessment (Paine, 2014, Gastroenterol Rep 2:161-168). With respect to rectal bleeding, blood streaks seen in the stool less than half the time is assigned 1 point, blood in most stools is assigned 2 points and pure blood passed is assigned 3 points. Regarding stool frequency, a normal number of daily stools is assigned 0 points, 1 or 2 more stools than normal is assigned 1 point, 3 or 4 more stools than normal is assigned 2 points, and 5 or more stools than usual is assigned 3 points. With respect to the endoscopy component, a score of 0 indicates normal mucosa or inactive UC, a score of 1 is given for mild disease with evidence of mild friability, reduced vascular pattern, and mucosal erythema, a score of 2 is given for moderate disease with friability, erosions, complete loss of vascular pattern, and significant erythema, and a score of 3 is given for ulceration and spontaneous bleeding (Schroeder et al., 1987, N Engl J Med, 317:1625-1629). Global assessment by a physician assigns 0 points for a finding of normal, 1 point for mild colitis, 2 points for moderate colitis and 3 points for severe colitis. Accordingly, in some embodiments, a patient treated with a SG-11 therapeutic protein or variant or fragment thereof is successfully treated when the patient experiences a reduction in the Mayo Score by at least 1, 2 or 3 points in at least one of: rectal bleeding, blood streaks seen in the stool, endoscopy subscore and physician's global assessment. In some embodiments, the method of treatment comprising administering to a patient diagnosed with UC a therapeutically effective amount of SG-11 protein or variant or fragment thereof results in a decrease in a diagnostic score of UC. For example, the score may change a diagnostic score, e.g., Mayo Score, by at least 1, 2, 3, 4, 5, 6, 7, 8, 9, 10 or 11 points.

Pouchitis

Additionally or alternatively, the compositions comprising a SG-11 therapeutic protein or variant and methods of administration as described herein can be used to treat pouchitis. Pouchitis is an inflammation of the lining of a pouch that is surgically created in the treatment of UC. Specifically, subjects having serious UC may have their diseased colon removed and the bowel reconnected by a procedure called ileoanal anastomosis (IPAA) or J-pouch surgery. Pouchitis cases can recur in many patients, manifesting either as acute relapsing pouchitis or chronic, unremitting pouchitis. Accordingly, provided herein are methods for treating pouchitis, acute pouchitis or recurrent pouchitis.

Pouchitis activity can be classified as remission (no active pouchitis), mild to moderately active (increased stool frequency, urgency, and/or infrequent incontinence), or severely active (frequent incontinence and/or the patient is hospitalized for dehydration). The duration of pouchitis can be defined as acute (less than or equal to four weeks) or chronic (four weeks or more) and the pattern classified as infrequent (1-2 acute episodes), relapsing (three or fewer episodes) or continuous. The response to medical treatment can be labeled as treatment responsive or treatment refractory, with the medication for either case being specified. Accordingly, in some embodiments, a method for treating a subject diagnosed with pouchitis is provided wherein treatment with a pharmaceutical composition comprising SG-11 or variant or fragment thereof results in a decrease in the severity of the pouchitis and/or results in remission.

Mucositis and Mucosal Barriers

The mucosa of the gastrointestinal (GI) tract is a complex microenvironment involving an epithelial barrier, immune cells, and microbes. A delicate balance is maintained in the healthy colon. Luminal microbes are physically separated from the host immune system by a barrier consisting of epithelium and mucus. The pathogenesis of IBD, although not fully elucidated, may involve an inappropriate host response to an altered commensal flora with a dysfunctional mucous barrier. See, Boltin et al., "Mucin Function in Inflammatory Bowel Disease An Update," J. Clin. Gastroenterol., Vol. 47(2):106-111 (February 2013).

Mucositis occurs when cancer treatments (particularly chemotherapy and radiation) break down the rapidly divided epithelial cells lining the intestinal tract (which goes from the mouth to the anus), leaving the mucosal tissue open to ulceration and infection. Mucosal tissue, also known as mucosa or the mucous membrane, lines all body passages that communicate with the air, such as the respiratory and alimentary tracts, and have cells and associated glands that secrete mucus. The part of this lining that covers the mouth, called the oral mucosa, is one of the most sensitive parts of the body and is particularly vulnerable to chemotherapy and radiation. The oral cavity is the most common location for mucositis. While the oral mucosa is the most frequent site of mucosal toxicity and resultant mucositis, it is understood that mucositis can also occur along the entire alimentary tract including the esophagus, stomach, small intestine (duodenum, jejunum, ileum), large intestine (colon), and rectum. In some embodiments, a pharmaceutical composition comprising SG-11 or a variant or fragment thereof is therapeutically effective to treat mucositis of the mouth, esophagus, stomach, small intestine (duodenum, jejunum, ileum), large intestine (colon), and/or rectum Oral mucositis can lead to several problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses). The World Health Organization has an oral toxicity scale for diagnosis of oral mucositis: Grade 1: soreness erythema, Grade 2: erythema, ulcers; patient can swallow solid food; Grade 3: ulcers with extensive erythema; patient cannot swallow solid food; Grade 4: mucositis to the extent that alimentation is not possible. Grade 3 and Grade 4 oral mucositis is considered severe mucositis. Accordingly, provided herein is a method for treating a subject diagnosed with oral mucositis, wherein administration of a pharmaceutical composition comprising SG-11 or a variant or fragment thereof reduces the grade of oral toxicity by at least 1 point of the grade scale of 1 to 4.

Colon Shortening

Ulcerative colitis is an idiopathic inflammatory bowel disease that affects the colonic mucosa and is clinically characterized by diarrhea, abdominal pain and hematochezia. The extent of disease is variable and may involve only the rectum (ulcerative proctitis), the left side of the colon to the splenic flexure, or the entire colon (pancolitis). The severity of the disease may also be quite variable histologically, ranging from minimal to florid ulceration and dysplasia. Carcinoma may develop. The typical histological (microscopic) lesion of ulcerative colitis is the crypt abscess, in which the epithelium of the crypt breaks down and the lumen fills with polymorphonuclear cells. The lamina propria is infiltrated with leukocytes. As the crypts are destroyed, normal mucosal architecture is lost and resultant scarring shortens and can narrow the colon. Thus, colon shortening can be a consequence of colitis disease and is often used diagnostically. For example, non-invasive plain abdominal x-rays can demonstrate the gaseous outline of the transverse colon in the acutely ill patient. Shortening of the colon and loss of haustral markings can also be demonstrated by plain films, as well as a double-contrast barium enema. Indications of ulcerative disease include loss of mucosal detail, cobblestone filling defects, and segmental areas of involvement See, "Ulcerative Colitis: Introduction—Johns Hopkins Medicine," found at: hopkinsmedicine.org/gastroenterology_hepatology/_pdfs/small_large_intestine/ulcerative_colitis.pdf on the World Wide Web.

Further, art recognized in vivo models of colitis will utilize shortening of colon length in scoring the severity of colitis in the model. See, Kim et al., "Investigating Intestinal Inflammation in DSS-induced Model of IBD," Journal of Visualized Experiments, Vol. 60, pages 2-6 (February 2012).

Epithelial Barrier Function in Non-IBD Disease

An improperly functioning epithelial barrier is increasingly implicated in, e.g., IBDs and mucositis. Moreover, there are numerous other diseases that studies have shown are also caused, linked, correlated, and/or exacerbated by, an improperly functioning epithelial barrier. These diseases include: (1) metabolic diseases, including—obesity, type 2 diabetes, non-alcoholic steatohepatitis (NASH), non-alcoholic fatty liver disease (NAFLD), liver disorders, and alcoholic steatohepatitis (ASH); (2) celiac disease; (3) necrotizing enterocolitis; (4) irritable bowel syndrome (IBS); (5) enteric infections (e.g. *Clostridium difficile*); (6) other gastro intestinal disorders in general; (7) interstitial cystitis; (8) neurological disorders or cognitive disorders (e.g. Alzheimer's, Parkinson's, multiple sclerosis, and autism); (9) chemotherapy associated steatohepatitis (CASH); and (10) pediatric versions of the aforementioned diseases. See, e.g.: Everard et al., "Responses of Gut Microbiota and Glucose and Lipid Metabolism to Prebiotics in Genetic Obese and Diet-Induced Leptin-Resistant Mice," Diabetes, Vol. 60, (November 2011), pgs. 2775-2786; Everard et al., "Cross-talk between *Akkermansia muciniphila* and intestinal epithelium controls diet-induced obesity," PNAS, Vol. 110, No. 22, (May 2013), pgs. 9066-9071; Cani et al., "Changes in Gut Microbiota Control Metabolic Endotoxemia-Induced Inflammation in High-Fat Diet-Induced Obesity and Diabetes in Mice," Diabetes, Vol. 57, (June 2008), pgs. 1470-1481; Delzenne et al., "Targeting gut microbiota in obesity: effects of prebiotics and probiotics," Nature Reviews, Vol. 7, (November 2011), pgs. 639-646. Consequently, restoring proper epithelial barrier function to patients may be critical in resolving the aforementioned disease states.

A properly functioning epithelial barrier in the lumen of the alimentary canal, including the mouth, esophagus, stomach, small intestine, large intestine, and rectum, is critical in controlling and maintaining the microbiome within the gastrointestinal tract and alimentary canal. The ecosystem for the microbiome includes the environment, barriers, tissues, mucus, mucin, enzymes, nutrients, food, and communities of microorganism, that reside in the gastrointestinal tract and alimentary canal. The integrity and permeability of the intestinal mucosal barrier impacts health in many critical ways.

A loss of integrity of the mucosal barrier in gastrointestinal disorders due to changes in mucin secretion may be related to host immune changes, luminal microbial factors, or directly acting genetic or environmental determinants. Thus, the disequilibrium of the mucous barrier may be central to the pathogenesis of IBD. Boltin et al., "Mucin Function in Inflammatory Bowel Disease An Update," J. Clin. Gastroenterol., Vol. 47(2):106-111 (February 2013).

Mucins are the primary constituent of the mucous layer lining the GI tract. There are at least 21 mucin (MUC) genes known in the human genome, encoding either secreted or membrane-bound mucins. The predominant mucins in the normal colorectum are MUC1, MUC2, MUC3A, MUC3B, MUC4, MUC13, and MUC17.1 MUC2 is the primary secretory, gel-forming component of intestinal mucus, produced in goblet cells. See, Boltin et al., "Mucin Function in Inflammatory Bowel Disease An Update," J. Clin. Gastroenterol., Vol. 47(2):106-111 (February 2013). Along with additional secreted mucins such as MUC1, 3A, 3B, 4, 13 and 17.1, goblet cell secretion of MUC2 forms a protective barrier on colonic epithelial cells reducing exposure to intestinal contents which may damage epithelial cells or prime immune responses.

Inflammatory Mechanisms in IBDs

There is significant evidence showing that certain cytokines are involved with IBD. Recent studies have demonstrated that cytokines play a crucial role in the pathogenesis of inflammatory bowel diseases (IBDs), such as Crohn's disease and ulcerative colitis, where they control multiple aspects of the inflammatory response. Markus Neurath, "Cytokines in Inflammatory Bowel Disease," Nature Reviews Immunology, Vol. 14, 329-342 (2014). In particular, the imbalance between pro-inflammatory and anti-inflammatory cytokines that occurs in IBD impedes the resolution of inflammation and instead leads to disease perpetuation and tissue destruction. Id. Recent studies suggest the existence of a network of regulatory cytokines that has important implications for disease progression. Id. Accordingly, experiments were performed to study the effects of SG-11 on production and/or secretion of pro-inflammatory and anti-inflammatory cytokines.

Pro-Inflammatory Cytokines

Briefly, pro-inflammatory cytokines are cytokines that are important in cell signaling and promote systemic inflammation. They are produced predominantly by activated macrophages and are involved in the upregulation of inflammatory reactions. Pro-inflammatory cytokines arise from genes that code for the translation of small mediator molecules that induce a response after upregulation. Interleukin-1 (IL-1), IL6, IL-12, IL-18, IL-23, CD40L, tumor necrosis factor (TNF) such as TNF-α, gamma-interferon (IFN-gamma), granulocyte-macrophage colony stimulating factor, and MCP-1 are well characterized as pro-inflammatory cytokines. Inflammation is characterized by an interplay between pro- and anti-inflammatory cytokines.

Reducing the biological activities of pro-inflammatory cytokines can be useful for the treatment of some diseases. For instance, blocking IL-1 or TNF-α has been successful in helping patients with rheumatoid arthritis, inflammatory bowel disease, or graft-vs-host disease. See, Strober W, Fuss I J (May 2011). "Proinflammatory cytokines in the pathogenesis of inflammatory bowel diseases," Gastroenterology, Vol. 140 (6): 1756-67.

Anti-Inflammatory Cytokines

Briefly, anti-inflammatory cytokines are a series of immunoregulatory molecules that regulate the proinflammatory cytokine response. These molecules thus modulate and help to decrease inflammatory responses triggered by pro-inflammatory cytokines. Anti-inflammatory cytokines include, e.g., IL4, IL-10, IL-13, IFN-α, and transforming growth factor-beta (TGF-β) are recognized as anti-inflammatory cytokines.

In some embodiments of the methods taught herein, administration of the pharmaceutical composition comprising a SG-11 protein or variant or fragment thereof is able to bring about reduced production of at least one pro-inflammatory cytokine (e.g., TNF-α and/or IL-23) by an immune cell in a patient administered the composition. In some embodiments, the administration is able to bring about an increase in the production of at least one anti-inflammatory cytokine (e.g., IL-10) by an immune cell in the patient. In some embodiments, the administration is able to bring about a decrease in the production of at least one anti-inflammatory cytokine (e.g., IL-10) by an immune cell in the patient In some embodiments, the administration is able to bring about an improvement of mucin production in epithelial cells and/or epithelial wound healing in the patient.

The dosing regimen used for treatment depends upon the desired therapeutic effect, on the route of administration, and on the duration of the treatment. The dose will vary from patient to patient, depending upon the nature and severity of disease, the patient's weight, special diets then being followed by a patient, concurrent medication, and other factors which those skilled in the art will recognize.

Generally, dosage levels of therapeutic protein between 0.0001 to 10 mg/kg of body weight daily are administered to the patient, e.g., patients suffering from inflammatory bowel disease. The dosage range will generally be about 0.5 mg to 100.0 g per patient per day, which may be administered in single or multiple doses.

In some aspects, the dosage range will be about 0.5 mg to 10 g per patient per day, or 0.5 mg to 9 g per patient per day, or 0.5 mg to 8 g per patient per day, or 0.5 mg to 7 g per patient per day, or 0.5 mg to 6 g per patient per day, or 0.5 mg to 5 g per patient per day, or 0.5 mg to 4 g per patient per day, or 0.5 mg to 3 g per patient per day, or 0.5 mg to 2 g per patient per day, or 0.5 mg to 1 g per patient per day.

In some aspects, the dosage range will be about 0.5 mg to 900 mg per patient per day, or 0.5 mg to 800 mg per patient per day, or 0.5 mg to 700 mg per patient per day, or 0.5 mg to 600 mg per patient per day, or 0.5 mg to 500 mg per patient per day, or 0.5 mg to 400 mg per patient per day, or 0.5 mg to 300 mg per patient per day, or 0.5 mg to 200 mg per patient per day, or 0.5 mg to 100 mg per patient per day, or 0.5 mg to 50 mg per patient per day, or 0.5 mg to 40 mg per patient per day, or 0.5 mg to 30 mg per patient per day, or 0.5 mg to 20 mg per patient per day, or 0.5 mg to 10 mg per patient per day, or 0.5 mg to 1 mg per patient per day.

Combination Therapies Comprising Therapeutic Proteins

The pharmaceutical compositions taught herein comprising a therapeutic protein may be combined with other treatment therapies and/or pharmaceutical compositions. For example, a patient suffering from an inflammatory bowel disease, may already be taking a pharmaceutical prescribed by their doctor to treat the condition. In embodiments, the pharmaceutical compositions taught herein, are able to be administered in conjunction with the patient's existing medicines.

For example, the therapeutic proteins taught herein may be combined with one or more of: an anti-diarrheal, a 5-aminosalicylic acid compound, an anti-inflammatory agent, an antibiotic, an antibody (e.g. antibodies targeting an inflammatory cytokine, e.g. antibodies targeting an anti-cytokine agent such as anti-TNF-α, (e.g., adalimumab, certolizumab pegol, golimumab, infliximab, V565) or anti-IL-12/IL-23 (e.g., ustekinumab, risankizumab, brazikumab, ustekinumab), a JAK inhibitor (e.g., tofacitinib, PF06700841, PF06651600, filgotinib, upadacitinib), an anti-integrin agent (e.g., vedolizumab, etrolizumab), a SiP inhibitor (e.g., etrasimod, ozanimod, amiselimod), a recombinant cell-based agent (e.g., Cx601), a steroid, a corticosteroid, an immunosuppressant (e.g., azathioprine and mercaptopurine), vitamins, and/or specialized diet.

Cancer patients undergoing chemotherapy or radiation therapy and suffering from or at risk of developing mucositis, e.g., oral mucositis, may be administered a pharmaceutical composition according to the present disclosure in combination with an agent used to treat mucositis such as oral mucositis. In some embodiments, a method of treatment comprises administering to a patient suffering from mucositis a combination of a pharmaceutical composition comprising SG-11 or a variant or fragment thereof and one or more second therapeutic agents selected from the group consisting of amifostine, benzocaine, benzydamine, ranitidine, omeprazole, capsaicin, glutamine, prostaglandin E2, Vitamin E, sucralfate, and allopurinol.

In some embodiments of the methods herein, the second therapeutic agent is administered in conjunction with the SG-11 protein described herein, either simultaneously or sequentially. In some embodiments, the protein and the second agent act synergistically for treatment or prevention of the disease, or condition, or symptom. In other embodiments, the protein and the second agent act additively for treatment or prevention of the disease, or condition, or symptom.

Pharmaceutical Compositions Comprising the SG-11 Therapeutic Protein

Pharmaceutical compositions are provided herein which comprise a SG-11 protein, variant or fragment thereof according to the present disclosure or pharmaceutically acceptable salt thereof and a pharmaceutically acceptable excipient. In some embodiments, the pharmaceutical composition is formulated for administration to the gastrointestinal lumen, including the mouth, esophagus, small intestine, large intestine, rectum and/or anus.

In some embodiments, the composition comprises one or more other substances which are associated with the source of the protein, for example, cellular components from a production host cell, or substance associated with chemical synthesis of the protein. In other embodiments, the pharmaceutical composition is formulated to include one or more second active agents as described herein. Moreover, the composition may comprise ingredients that preserve the structural and/or functional activity of the active agent(s) or of the composition itself. Such ingredients include but are not limited to antioxidants and various antibacterial and antifungal agents, including but not limited to parabens (e.g., methylparabens, propylparabens), chlorobutanol, phenol, sorbic acid, thimerosal or combinations thereof.

The terms "pharmaceutical" or pharmaceutically acceptable" refers compositions that do not or preferably do not produce an adverse, allergic, or other untoward reaction when administered to an animal, such as, for example, a human, as appropriate. The preparation of a pharmaceutical composition or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

The pharmaceutical compositions of the disclosure are formulated according to the intended route of administration and whether it is to be administered, e.g., in solid, liquid or aerosol form. In a preferred embodiment, the composition can be administered rectally, but may also be administered topically, by injection, by infusion, orally, intrathecally, intranasally, subcutaneously, mucosally, localized perfusion bathing target cells directly, via a catheter, via a lavage, or by other method or any combination of the foregoing as would be known to one of ordinary skill in the art. Liquid formulations comprising a therapeutically effective amount of the protein can be administered rectally by enema, catheter, use of a bulb syringe. A suppository is an example of a solid dosage form formulated for rectal delivery. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and or about 1% to about 2%. Injectable liquid compositions are typically based upon injectable sterile saline or phosphate-buffered saline or other injectable carriers known in the art. Other liquid compositions include suspensions and emulsions. Solid compositions such as for oral administration may be in the form of tablets, pills, capsules (e.g., hard or soft-shelled gelatin capsules), buccal compositions, troches, elixirs, suspensions, syrups, wafers, or combinations thereof. The active agent in such liquid and solid compositions, i.e., a protein as described herein, is typically a component, being about 0.05% to 10% by weight, with the remainder being the injectable carrier and the like.

The pharmaceutical composition may be formulated as a controlled or sustained release composition which provide release of the active agent(s) including the therapeutic protein of the present disclosure over an extended period of time, e.g., over 30-60 minutes, or over 1-10 hours, 2-8 hours, 8-24 hours, etc. Alternatively or additionally, the composition is formulated for release to a specific site in the host body. For example, the composition may have an enteric coating to prevent release of the active agent(s) in an acidic environment such as the stomach, allowing release only in the more neutral or basic environment of the small intestine, colon or rectum. Alternatively or additionally, the composition may be formulated to provide delayed release in the mouth, small intestine or large intestine.

Each of the above-described formulations may contain at least one pharmaceutically acceptable excipient or carrier, depending up the intended route of administration, e.g., a solid for rectal administration or liquid for intravenous or parenteral administration or administration via cannula. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*. 18$^{th}$ Ed. Mack Printing Company, 1990, pp. 1289-1329, incorporated herein by reference).

The pharmaceutical compositions for administration can be present in unit dosage forms to facilitate accurate dosing. Typical unit dosage forms include prefilled, premeasured ampules or syringes of the liquid compositions or suppositories, pills, tablets, capsules or the like in the case of solid compositions. In some embodiments of such compositions, the active agent, i.e., a protein as described herein, may be a component (about 0.1 to 50 wt/wt %, 1 to 40 wt/wt %, 0.1 to 1 wt/wt %, or 1 to 10 wt/wt %) with the remainder being various vehicles or carriers and processing aids helpful for forming the desired dosing form.

The actual dosage amount in a unit dosage form of the present disclosure administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Protein Expression Systems and Protein Production

Provided herein are compositions and methods for producing isolated proteins of the present disclosure as well as expression vectors which contain polynucleotide sequence encoding the proteins and host cells which harbor the expression vectors.

The proteins of the present disclosure can be prepared by routine recombinant methods, e.g., culturing cells transformed or transfected with an expression vector containing a nucleic acid encoding the SG-11 therapeutic protein, variant or fragment thereof. Host cells comprising any such vector are also provided. Host cells can be prokaryotic or eukaryotic and examples of host cells include *E. coli*, yeast, or mammalian cells. A method for producing any of the herein described proteins is further provided and comprises culturing host cells under conditions suitable for expression of the desired protein and recovering the desired protein from the cell culture. The recovered protein can then be isolated and/or purified for use in in vitro and in vivo methods, as well as for formulation into a pharmaceutically acceptable composition. In some embodiments, the protein is expressed in a prokaryotic cell such as *E. coli* and the isolation and purification of the protein includes step to reduce endotoxin to levels acceptable for therapeutic use in humans or other animals.

Expression Vectors

Provided herein are expression vectors which comprise a polynucleotide sequence which encodes a protein of the present disclosure or a variant and/or fragment thereof. Polynucleotide sequences encoding the proteins of the disclosure can be obtained using standard recombinant techniques. Desired encoding polynucleotide sequences may be amplified from the genomic DNA of the source bacterium, i.e., *R. hominis*. Alternatively, polynucleotides can be synthesized using nucleotide synthesizer. Once obtained, sequences encoding the polypeptides are inserted into a recombinant vector capable of replicating and expressing heterologous (exogenous) polynucleotides in a host cell. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using a pBR322, pUC, pET or pGEX vector, a plasmid derived from an *E. coli* species. Such vectors contain genes encoding ampicillin (Amp) and tetracycline (Tet) resistance and thus provides easy means for identifying transformed cells. These vectors as well as their derivatives or other microbial plasmids or bacteriophage may also contain, or be modified to contain, promoters which can be used by the microbial organism for expression of endogenous proteins.

An expression vector of the present disclosure may comprise a promoter, an untranslated regulatory sequence located upstream (5) and operably linked to a protein-encoding nucleotide sequence such that the promoter regulated transcription of that coding sequence. Prokaryotic promoters typically fall into two classes, inducible and constitutive. An inducible promoter is a promoter that initiates increased levels of transcription of the encoding polynucleotide under its control in response to changes in the culture condition, e.g., the presence or absence of a nutrient or a change in temperature. A large number of promoters recognized by a variety of potential host cells are well known and a skilled artisan can choose the promoter according to desired expression levels. Promoters suitable for use with prokaryotic hosts include *E. coli* promoters such as lac, trp, tac, trc and ara, viral promoters recognized by *E. coli* such as lambda and T5 promoters, and the T7 and T7lac promoters derived from T7 bacteriophage. A host cell harboring a vector comprising a T7 promoter, e.g., is engineered to express a T7 polymerase. Such host cells include *E. coli* BL21(DE3), Lemo21(DE3), and NiCo21(DE3) cells. In some embodiments, the promoter is an inducible promoter which is under the control of chemical or environmental factors.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Suitable vectors for expression in both prokaryotic and eukaryotic host cells are known in the art and some are further described herein.

Vectors of the present disclosure may further comprise a signal sequence which allows the translated recombinant protein to be recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. Well-known signal sequences for use in eukaryotic expression systems include but are not limited to interleukin-2, CD5, the Immunoglobulin Kappa light chain, trypsinogen, serum albumin, and prolactin.

The SG-11 proteins or variants or fragments thereof as described herein can be expressed as a fusion protein or polypeptide. Commonly used fusion partners include but are not limited to human serum albumin and the crystallizable fragment, or constant domain of IgG, Fc. The histidine tag or FLAG tag can also be used to simplify purification of recombinant protein from the expression media or recombinant cell lysate. The fusion partners can be fused to the N- and/or C-terminus of the protein of interest.

Host Cells

Suitable host cells for cloning or expressing the DNA in the vectors herein include prokaryote, yeast, or higher eukaryote cells. Numerous cell lines and cultures are available for use as a host cell, and they can be obtained for example through the American Type Culture Collection (ATCC), which is an organization that serves as an archive for living cultures and genetic materials. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5a, JM109, and KC8, bacilli such as *Bacillus subtilis*; and other enterobacteriaceae such as *Salmonella typhimurium*, *Serratia marcescens*, various *Pseudomonas* species, as well as a number of commercially available bacterial hosts such as SURE® Competent Cells and SOLOPACK™ Gold Cells (STRATAGENE®, La Jolla). In certain embodiments, bacterial cells such as *E. coli* are particularly contemplated as host cells.

Examples of eukaryotic host cells for replication and/or expression of a vector include, but are not limited to, HeLa, NIH3T3, Jurkat, 293, Cos, CHO, Saos, and PC12. Additional eukaryotic host cells include yeasts (e.g., *Pichia pastoris* and *Saccharomyces cerevisiae*) and cells derived from insects (e.g., *Spodoptera frugiperda* or *Trichoplusia ni*). Many host cells from various cell types and organisms are available and would be known to one of skill in the art. Similarly, a viral vector may be used in conjunction with either a eukaryotic or prokaryotic host cell, particularly one that is permissive for replication or expression of the vector. The selection of the appropriate host cell is deemed to be within the skill in the art.

Methods are well known for introducing recombinant DNA, i.e., an expression vector, into a host cell so that the DNA is replicable, either as an extrachromosomal element or as a chromosomal integrant, thereby generating a host cell which harbors the expression vector of interest. Methods of transfection are known to the ordinarily skilled artisan, for example, by $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. General aspects of mammalian cell host system transformations have been described in U.S. Pat. No. 4,399,216. Transformations into yeast are typically carried out according to the method of Van Solingen et al., J. Bact, 130:946 (1977) and Hsiao et al., Proc. Natl. Acad. Sci. (USA), 76:3829 (1979). Other methods for introducing DNA into cells include nuclear microinjection, electroporation, bacterial protoplast fusion with intact cells, or introduction using polycations, e.g., polybrene, polyornithine. For various techniques for transforming mammalian cells, see Keown et al., Methods in Enzymology. 185:527-537 (1990) and Mansour et al., Nature, 336:348-352 (1988).

Accordingly, provided herein is a recombinant vector or expression vector as described above and comprising a polynucleotide which encodes a SG-11 therapeutic protein sequence of interest (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or variant and/or fragment thereof as described herein). The polynucleotide can be, for example, any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or a variant or a fragment thereof. Moreover, the present disclosure teaches a host cell harboring the vector. The host cell can be a eukaryotic or prokaryotic cell as detailed above. In a preferred embodiment, the host cell is a prokaryotic cell. In a further preferred embodiment, the host cell is *E. coli*.

In some embodiments, the polynucleotide encoding the protein of interest is codon-optimized. A codon optimization algorithm is applied to a polynucleotide sequence encoding a protein in order to choose an appropriate codon for a given amino acid based on the expression host's codon usage bias. Many codon optimization algorithms also take into account other factors such as mRNA structure, host GC content, ribosomal entry sites. Some examples of codon optimization algorithms and gene synthesis service providers are: AUTM: atum.bio/services/genegps; GenScript: genscript.com/codon-opt.html; ThermoFisher: thermofisher.com/us/en/home/life-science/cloning/gene-synthesis/geneart-gene-synthesis/geneoptimizer.html; and Integrated DNA Technologies: idtdna.com/CodonOpt, all of which can be found on the World Wide Web. The nucleotide sequence is then synthesized and cloned into an appropriate expression vector. In the present disclosure, codon-optimized sequences in the present disclosure include SEQ ID NO:8, SEQ ID NO:12, SEQ ID NO:14, SEQ ID NO:16, SEQ ID NO:18 and SEQ ID NO:20.

Methods to Produce the Protein

Methods are provided for producing the proteins described herein but are well known to the ordinarily skilled artisan. Host cells transformed or transfected with expression or cloning vectors described herein for protein production are cultured in conventional nutrient media modified as appropriate for inducing promoters, selecting and/or maintaining transformants, and/or expressing the genes encoding the desired protein sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Molecular Cloning: A Laboratory Manual (Sambrook, et al., 1989, Cold Spring Harbor Laboratory Press).

Generally, "purified" will refer to a specific protein composition that has been subjected to fractionation to remove non-proteinaceous components and various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present disclosure, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

Another example is the purification of a specific fusion protein using a specific binding partner. Such purification methods are routine in the art. As the present disclosure provides DNA sequences for the specific proteins, any fusion protein purification method can now be practiced. This is exemplified by the generation of a specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

In other embodiments, a preparation enriched with the peptides may be used instead of a purified preparation. In this document, whenever purified is used, enriched may be used also. A preparation may not only be enriched by methods of purification, but also by the over-expression or over-production of the peptide by bacteria when compared to wild-type. This can be accomplished using recombinant methods, or by selecting conditions which will induce the expression of the peptide from the wild type cells.

Recombinantly expressed polypeptides of the present disclosure can be recovered from culture medium or from host cell lysates. The suitable purification procedures include, for example, by fractionation on an ion-exchange (anion or cation) column; ethanol precipitation; reverse phase HPLC; chromatography on silica or on a cation-exchange resin such as DEAE; chromatofocusing; SDS-PAGE; ammonium sulfate precipitation; gel filtration or size exclusion chromatograph (SEC) using, for example, Sephadex G-75; and metal chelating columns to bind epitope-tagged forms of a polypeptide of the present disclosure. Various methods of protein purification can be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular polypeptide produced.

Alternative methods, which are well known in the art, can be employed to prepare a polypeptide of the present invention. For example, a sequence encoding a polypeptide or portion thereof, can be produced by direct peptide synthesis using solid-phase techniques (see, e.g., Stewart et al., 1969, Solid-Phase Peptide Synthesis, W.H. Freeman Co., San Francisco, Calif.; Merrifield. J. 1963, Am. Chem. Soc., 85:2149-2154. In vitro protein synthesis can be performed using manual techniques or by automation. Automated synthesis can be accomplished, for instance, using an Applied Biosystems Peptide Synthesizer (Foster City, Calif.) using manufacturer's instructions. Various portions of a polypeptide of the present invention or portion thereof can be chemically synthesized separately and combined using chemical or enzymatic methods to produce the full-length polypeptide or portion thereof.

In some embodiments, the disclosure provides chimeric molecules comprising any of the herein described polypeptides fused to a heterologous polypeptide or amino acid sequence and the polynucleotides encoding the chimeric molecules. Examples of such chimeric molecules include, but are not limited to, any of the herein described polypeptides fused to an epitope tag sequence, an Fc region of an immunoglobulin.

Recombinant Bacterial Delivery Systems

The present disclosure contemplates utilizing delivery systems outside of the traditional pharmaceutical formulations that comprise a purified protein. In some embodiments, the disclosure utilizes recombinant bacterial delivery systems, phage-mediated delivery systems, chitosan-DNA complexes, or AAV delivery systems.

One particular recombinant bacterial delivery system is based upon *Lactococcus lactis*. Essentially, one may clone the gene encoding the therapeutic protein (e.g. SEQ ID NO:3) into an expression vector, and then transform the vector into *L. lactis*. Subsequently, one may then administer the *L. lactis* to a patient. See, e.g. Bratt, et al., "A phase 1 trial with transgenic bacteria expressing interleukin-10 in Crohn's disease," Clinical Gastroenterology and Hepatology, 2006, Vol. 4, pgs. 754-759 ("We treated Crohn's disease patients with genetically modified *Lactococcus lactis* (LL-Thy12) in which the thymidylate synthase gene was replaced with a synthetic sequence encoding mature human interleukin-10."); Shigemori, et al., "Oral delivery of *Lactococcus lactis* that secretes bioactive heme oxygenase-1 alleviates development of acute colitis in mice," Microbial Cell Factories, 2015, Vol. 14:189 ("Mucosal delivery of therapeutic proteins using genetically modified strains of lactic acid bacteria (gmLAB) is being investigated as a new therapeutic strategy."); Steidler, et al., "Treatment of murine colitis by *Lactococcus lactis* secreting interleukin-10," Science, 2000, Vol. 289, pgs. 1352-1355 ("The cytokine interleukin-10 (IL-10) has shown promise in clinical trials for treatment of inflammatory bowel disease (IBD). Using two mouse models, we show that the therapeutic dose of IL-10 can be reduced by localized delivery of a bacterium genetically engineered to secrete the cytokine. Intragastric administration of IL-10D secreting *Lactococcus lactis* caused a 50% reduction in colitis in mice treated with dextran sulfate sodium and prevented the onset of colitis in IL-102/2 mice. *Ibis* approach may lead to better methods for cost effective and long-term management of IBD in humans."); Hanniffy, et al., "Mucosal delivery of a pneumococcal vaccine using *Lactococcus lactis* affords protection against respiratory infection," Journal of Infectious Diseases, 2007, Vol. 195, pgs. 185-193 ("Here, we evaluated *Lactococcus lactis* intracellularly producing the pneumococcal surface protein A (PspA) as a mucosal vaccine in conferring protection against pneumococcal disease."); and Vandenbroucke, et al., "Active delivery of trefoil factors by genetically modified *Lactococcus lactis* prevents and heals acute colitis in mice," Gastroenterology, 2004, Vol. 127, pgs. 502-513 ("We have positively evaluated a new therapeutic approach for acute and chronic colitis that involves in situ secretion of murine TFF by orally administered *L. lactis*. This novel approach may lead to effective management of acute and chronic colitis and epithelial damage in humans.").

In another embodiment, a "synthetic bacterium" may be used to deliver an SG-11 protein or variant or fragment thereof wherein a probiotic bacterium is engineered to express the SG-11 therapeutic protein (see, e.g., Durrer and Allen, 2017, PLoS One, 12:e0176286).

Phages have been genetically engineered to deliver specific DNA payloads or to alter host specificity. Transfer methods, such as phages, plasmids, and transposons, can be used to deliver and circulate engineered DNA sequences to microbial communities, via processes such as transduction, transformation, and conjugation. For purposes of the present disclosure, it is sufficient to understand that an engineered phage could be one possible delivery system for a protein of the disclosure, by incorporating the nucleic acid encoding said protein into the phage and utilizing the phage to deliver the nucleic acid to a host microbe that would then produce the protein after having the phage deliver the nucleic acid into its genome.

Similar to the aforementioned engineered phage approach, one could utilize a transposon delivery system to incorporate nucleic acids encoding a therapeutic protein into a host microbe that is resident in a patient's microbiome. See, Sheth, et al., "Manipulating bacterial communities by in situ microbiome engineering," Trends in Genetics, 2016, Vol. 32, Issue 4, pgs. 189-200.

The following examples are intended to illustrate, but not limit, the disclosure.

EXAMPLES

The following experiments utilize a robust mixture of in vitro experiments combined with in vivo models of IBD to demonstrate the therapeutic ability of the taught proteins and methods.

Example 1

Expression of SG-11 and Variants Thereof

For experiments described in the examples below, a polynucleotide encoding SG-11 (SEQ ID NO:3) was obtained by PCR amplification of genomic DNA obtained from *Roseburia hominis* (A2-183; DSM 16839 type strain; See, e.g. Duncan, S. H., Aminov, R. I., Scott, K. P., Louis, P., Stanton, T. B., Flint, H. J. (2006). Proposal of *Roseburia faecis* sp. nov., *Roseburia hominis* sp. nov. and *Roseburia inulinivorans* sp. nov., based on isolates from human faeces. Int. J. Syst. Evol. Microbiol. Vol. 56, pgs. 2437-2441. The encoding polynucleotide was then subcloned into an inducible expression vector and used to transform *E. coli* BL21 (DE3) cells for expression and purification of SG-11 or variants thereof as detailed below, using culturing and purification methods which are routine in the art.

Expression of SG-11 (Comprising SEQ ID NO:3).

Expression and purification of proteins comprising the amino acid sequence of SG-11 (SEQ ID NO:5) for use in various experiments pertaining to the present disclosure is described below was achieved using a pGEX vector system which is designed for inducible, high-level intracellular expression of genes or gene fragments. Expression in E. coli yields tagged proteins with the GST moiety at the amino terminus and the protein of interest at the carboxyl terminus. The vector has a tac promoter for chemically inducible, high-level expression and an internal laql$^q$ gene for use in any E. coli host.

A polynucleotide comprising a nucleotide sequence encoding SG-11 (SEQ ID NO:3 from R. hominis DSM 16839) was inserted into the multiple-cloning site (BamHI and NotI sites) of a pGEX-6P-1 (GE Healthcare Life Science, Pittsburgh, Pa.) to express SG-11 as a GST fusion protein which was then cleaved at the Precision protease site, generating SG-11 having the amino acid sequence of SEQ ID NO:5 (encoded by SEQ ID NO:6), provided in Table 4 below. This protein was expressed and purified by 2 alternate methods. In the first, BL21(DE3) transformants were grown in LB and 100 µg/ml carbenicillin and 1 µg/ml chloramphenicol at 30° C. Expression was induced when a culture density of 0.6 OD$_{600}$ was reached, with 0.4 mM IPTG for 4 h. Cells were harvested by centrifugation then lysed by sonication, and a soluble lysate was applied to a GST-resin column. Bound protein was washed with PBS and then purified tag-free SG-11C was eluted by adding PreScission Protease to cleave the protein C-terminal to the GST-tag.

An alternative method of expression and purification, using the same pGEX expression construct, was performed by growing the transformed BL21(DE3) cells in LB with 50 µg/ml carbenicillin at 37° C. When cultures reached a density of 0.7 OD$_{600}$, they were chilled to 16° C. and expression was induced with 1 mM IPTG at 16° C. for 15 h. Cells were harvested and lysed by sonication, and a soluble lysate was applied to a GSTrap column. Bound protein was washed with HEPES buffer and then purified tag-free SG-11 (SEQ ID NO:5) was eluted by adding HRV3C protease to cleave the protein C-terminal to the GST-tag. Eluted fractions containing protein as determined by SDS-PAGE and Coomasie Brilliant Blue staining were identified and pooled, then applied to a HITRAP® Q HP anion exchange column then to a SUPERDEX® 75 (26/60) preparative size exclusion column (SEC) to obtain a final preparation.

TABLE 4

| Amino Acid Sequence | Encoding Nucleic Acid Sequence |
|---|---|
| SEQ ID NO: 5 | SEQ ID NO: 6 |
| GPLGSLEGEESVVYVGKK | GGGCCCTGGGATCCCTGGAGGGAGAGGAAAGTGTC |
| GVIASLDVETLDQSYYDET | GATGTGGAGACGCTCGATCAGTCCTACTACGATGAG |
| ELKSYVDAEVEDYTAEHG | ACGGAACTGAAGTCCTATGTGGATGCAGAGGTGGAA |
| KNAVKVESLKVEDGVAKL | GATTACACCGCGGAGCATGGTAAAAATGCAGTCAAG |
| KMKYKTPEDYTAFNGIEL | GTGGAGAGCCTTAAGGTGGAAGACGGTGTGGCGAAG |
| YQGKVVASLAAGYVYDG | CTTAAGATGAAGTACAAGCACCGGAGGATTATACC |
| EFARVEEGKVVGAATKQD | GCATTTAATGGAATTGAACTCTATCAGGGGAAAGTC |
| IYSEDDLKVAIIRANTDVK | GTTGCTTCCCTGGCGGCAGGATACGTCTACGACGGG |
| VDGEICYVSCQNVKLTGK | GAGTTCGCCCGCGTGGAGGAAGGCAAGGTTGTGGGA |
| DSVSIRDGYYLETGSVTAS | GCTGCCACAAAACAGGATATTTACTCTGAGGATGATT |
| VDVTGQESVGTEQLSGTE | TGAAAGTTGCCATCATCCGTGCCAATACGGATGTGA |
| QMEMTGEPVNADDTEQTE | AGGTGGACGGTGAGATCTGCTATGTCTCCTGTCAGAA |
| AAAGDGSFETDVYTFIVYK | TGTGAAGCTGACCGGAAAAGACAGTGTGTCGATCCG |
| AAAS | TGACGGATATTATCTTGAGACGGGAAGCGTGACGGC |
| | ATCCGTGGATGTGACCGGACAGGAGAGCGTCGGGAC |
| | CGAGCAGCTTTCGGGAACCGAACAGATGGAGATGAC |
| | CGGGGAGCCGGTGAATGCGGATGATACCGAGCAGAC |
| | AGAGGCGGCGGCCGGTGACGGTTCGTTCGAGACAGA |
| | CGTATATACTTTCATTGTCTACAAAGCGGCCGCATCG |

Expression and purification of the mature SG-11 protein having no signal peptide was done using a pD451-SR vector system (AUTM, Newark, Calif.). This expression vector utilizes an IPTG-inducible T7 promoter. The polynucleotide (SEQ ID NO:4) encoding SG-11 (SEQ ID NO:3) was codon-optimized at AUTM (Newark, Calif.) to generate the codon-optimized coding sequence provided herein as SEQ ID NO:8. This codon-optimized coding sequence was inserted into the pD451-SR vector and the resultant construct provides expression of the 233-amino acid SG-11 protein provided herein as SEQ ID NO:7.

BL21(DE3) cells transformed with the construct were grown in auto-induction media, MAGICMEDIA™ (ThermoFisher). The cultures were incubated with shaking at 25° C. for 8 hours then 16° C. for up to 72 h. Cells were pelleted by centrifugation, re-suspended in 100 mM Tris-HCl, pH 8.0 containing 50 mM NaCl, 2 mg/ml lysozyme and protease inhibitor, then TRITON™ X-100 was added to the suspension. Cells were then sonicated and clear lysate was prepared by centrifugation for purification of the protein by standard column chromatography techniques.

SG-11 (SEQ ID NO:7) was purified with two anion exchange columns, HITRAP® Q HP followed by Mono Q. Fractions containing partially purified proteins as determined by SDS-PAGE and Coomassie Blue staining were further purified with MONO Q®. Purification protocol for MONO Q® was the same as that for HITRAP® Q. The fractions containing SG-11 were pooled and dialyzed in buffer (50 mM sodium phosphate, 150 mM NaCl and 10% glycerol). Purity and uniformity was analyzed with SDS-PAGE and analytical SEC, SUPERDEX® 200 Increase 3.2/300, and the preparation was assessed to have about 92.7% purity.

The pD451-SR vector system was also used to express and purify the SG-11 variant SG-11V5 (SEQ ID NO:19). To generate the expression construct, the codon-optimized sequence of SG-11 (SEQ ID NO:8) was modified to generate the polynucleotide of SEQ ID NO:20 which encodes SG-11V5 (SEQ ID NO:19). The SG-11V5 encoding sequence was cloned into the pD451-SR vector.

BL21(DE3) cells transformed with the construct were grown and processed for preparation of clear lysate as described above for expression of SG-11 (SEQ ID NO:7).

SG-11V5 protein was purified from clear lysate by HITRAP® Q purification, followed by hydrophobic interaction chromatography (HIC), HITRAP® Butyl HP. Fractions containing SG-11V5 and determined by SDS-PAGE and Coomassie Blue staining were pooled and dialyzed in buffer in buffer (50 mM sodium phosphate, 150 mM NaCl and 10% glycerol). All column chromatography described for preparation of and was performed using ÄKTA™ protein purification systems (GE Healthcare Life Sciences, Pittsburgh, Pa.).

Purified proteins were quantified by densitometry using bovine serum albumin as a reference following SDS-PAGE and Coomassie Brilliant Blue staining. Endotoxin levels were measured with ENDOSAFE® NEXGEN-MCS™ (Charles River, Wilmington, Mass.) according to the manufacturer's instructions. Endotoxin levels of proteins used for the assays described herein were lower than 1 EU/mg.

An expression construct was generated in which a pET-28 vector (Sigma Millipore) was used to harbor and express a polynucleotide sequence (SEQ ID NO:4) encoding SG-11 (SEQ ID NO:3) with a FLAG-tag (DYKDDDDK; SEQ ID NO:32) at the N-terminus of SG-11. The full FLAG-tagged SG-11 protein sequence is provided herein as SEQ ID NO:9 (and was encoded by SEQ ID NO:10). Protein expression using this construct is under the control of the T7 promoter, which can be induced with isopropyl 0-D-1-thiogalactopyranoside (IPTG).

The FLAG-tag at the N-terminus was incorporated into the construct using PCR and oligonucleotides encoding DYKDDDDK. The transformed host cells were grown in 2×YT media overnight at 37° C. The overnight culture was then inoculated into fresh 2×YT media and incubated at 37° C. for 4 hours. The 4-hour culture was then inoculated (1% inoculation) into MAGICMEDIA™ E. coli Expression Medium (ThermoFisher). Cells were grown at 25° C. for 8 h and then 16° C. for up to 72 h prior to harvesting by centrifugation. The protein was expressed as a soluble form allowing recovery from a clear lysate. The expressed protein was purified using a HITRAP® Q anion exchange column followed by a SUPERDEX® 200 Increase 10/300 GL SEC. Purity and uniformity was analyzed with SDS-PAGE and analytical SEC, SUPERDEX® 200 Increase 3.2/300, and the preparation was assessed to have about 93.3% purity.

Preparation of SG-11 Proteins for Stability Analysis

SG-11 (SEQ ID NO:7) and its variant, SG-11V5 (SEQ ID NO:19) were purified with two anion exchange columns, HITRAP® Q followed by MONO Q®. Fractions containing partially purified proteins as determined by SDS-PAGE and Coomassie Blue staining were further purified with Mono Q. Purification protocol for MONO Q® was the same as that for HITRAP® Q. The fractions containing SG-11 were pooled and dialyzed in buffer (50 mM sodium phosphate, 150 mM NaCl and 10% glycerol).

For SG-11V5, following HITRAP® Q purification, the protein was further purified with hydrophobic interaction chromatography (HIC), HITRAP® Butyl HP. Fractions containing SG-11V5 and determined by SDS-PAGE and Coomassie Blue staining were pooled and dialyzed in buffer in buffer (50 mM sodium phosphate, 150 mM NaCl and 10% glycerol). All column chromatography described for preparation of and was performed using ÄKTA™ protein purification systems (GE Healthcare Life Sciences, Pittsburgh, Pa.).

Purified proteins were quantified by densitometry using bovine serum albumin as a reference following SDS-PAGE and Coomassie Blue staining. Endotoxin levels were measured with ENDOSAFE® NEXGEN-MCS' (Charles River, Wilmington, Mass.) according to the manufacturer's instructions. Endotoxin levels of proteins used for the assays described herein were lower than 1 EU/mg.

Example 2

Effect of SG-11 on Restoration of Epithelial Barrier Integrity Following Inflammation Induced Disruption The following experiment demonstrates the therapeutic ability of a SG-11 protein or variant thereof as disclosed herein to restore gastrointestinal epithelial barrier integrity. The experiment is therefore a demonstration of the functional utility of the therapeutic proteins to treat a gastrointestinal inflammatory disorder or disease involving impaired epithelial barrier integrity/function.

Assays were performed as described below in trans-well plates where co-cultures of multiple cell types were performed utilizing a permeable membrane to separate cells. In the apical (top) chamber, human colonic epithelial cells, consisting of a mixture of enterocytes and goblet cells, were cultured until cells obtained tight junction formation and barrier function capacity as assessed by measurement of trans-epithelial electrical resistance (TEER). In the basolateral chamber, monocytes were cultured separately. Epithelial cells were primed with inflammatory cytokines. The assays measured the effect of a therapeutic protein, i.e., SG-11, on epithelial barrier function, muc2 gene expression, and production of cytokines.

Cell culture. The HCT8 human enterocyte cell line (ATCC Cat. No. CCL-244) was maintained in RPMI-1640 medium supplemented with 10% fetal bovine serum, 100 IU/ml penicillin, 100 µg/ml streptomycin, 10 µg/ml gentamicin and 0.25 µg/ml amphotericin (cRPMI). HT29-MTX human goblet cells (Sigma-Aldrich (St. Louis, Mo.; Cat. No. 12040401) were maintained in DMEM medium with 10% fetal bovine serum, 100 IU/ml penicillin, 100 µg/ml streptomycin, 10 µg/ml gentamicin and 0.25 µg/ml amphotericin (cDMEM). Epithelial cells were passaged by trypsinization and were used between 5 and 15 passages following thawing from liquid nitrogen stocks. U937 monocytes (ATCC Cat. No. 700928) were maintained in cRPMI medium as a suspension culture, and split by dilution as needed to maintain cells between $5 \times 10^5$ and $2 \times 10^6$ cells/ml. U937 cells were used up to passage 18 following thawing from liquid nitrogen stocks.

Epithelial cell culture. A mixture of HCT8 enterocytes and HT29-MTX goblet cells were plated at a 9:1 ratio, respectively, in the apical chamber of the transwell plate as described previously (Berget et al., 2017, Int J Mol Sci, 18:1573; Beduneau et al., 2014, Eur J Pharm Biopharm, 87:290-298). A total of $10^5$ cells were plated in each well ($9 \times 10^4$ HCT8 cells and $1 \times 10^4$ HT29-MTX cells per well). Epithelial cells were trypsinized from culture flasks and viable cells determined by trypan blue counting. The correct volumes of each cell type were combined in a single tube and centrifuged. The cell pellet was resuspended in cRPMI and added to the apical chamber of the transwell plate. Cells were cultured for 8 to 10 days at 37° C.+5% $CO_2$, and media was changed every 2 days.

Monocyte culture. On day 6 of epithelial cell culture 2×10⁵ cells/well U937 monocytes were plated into a 96 well receiver plate. Cells were cultured at 37° C.+5% $CO_2$ and media was changed every 24 hours for four days.

Co-culture assay. Following 8-10 days of culture the transwell plate containing enterocytes were treated with 10 ng/ml IFN-γ added to the basolateral chamber of the transwell plate for 24 hours at 37° C.+5% $CO_2$. After 24 hours fresh cRPMI was added to the epithelial cell culture plate. Trans-epithelial electrical resistance (TEER) readings were measured after the IFN-γ treatment and were used as the pre-treatment TEER values. SG-11 was then added to the apical chamber of the transwell plate at a final concentration of 1 μg/ml (40 nM). The myosin light chain kinase (MLCK) inhibitor peptide 18 (BioTechne, Minneapolis, Minn.) was used at 50 nM as a positive control to prevent inflammation induced barrier disruption (Zolotarevskky et al., 202, Gastroenterology, 123:163-172). The bacterially derived molecule staurosporine was used at 100 nM as a negative control to induce apoptosis and exacerbate barrier disruption (Antonsson and Persson, 2009, Anticancer Res, 29:2893-2898). Compounds were incubated on enterocytes for 1 hour or 6 hours. Following pre-incubation with test compounds the transwell insert containing the enterocytes was transferred on top of the receiver plate containing U937 monocytes. Heat killed *E. coli* (HK *E. coli*) (bacteria heated to 80° C. for 40 minutes) was then added to both the apical and basolateral chambers and a multiplicity of infection (MOI) of 10. Transwell plates were incubated at 37° C.+5% $CO_2$ for 24 hours and a post treatment TEER measurement was made. The TEER assays were performed with mature SG-11 protein (SEQ ID NO:5 or SEQ ID NO:9).

Data analysis. Raw electrical resistance values in ohms (Ω) were converted to ohms per square centimeter ($\Omega cm^2$) based on the surface area of the transwell insert (0.143 $cm^2$). To adjust for differential resistances developing over 10 days of culture, individual well post treatment $\Omega cm^2$ readings were normalized to pre-treatment $\Omega cm^2$ readings. Normalized $\Omega cm^2$ values were then expressed as a percent change from the mean $\Omega cm^2$ values of untreated samples.

Figure 1B:
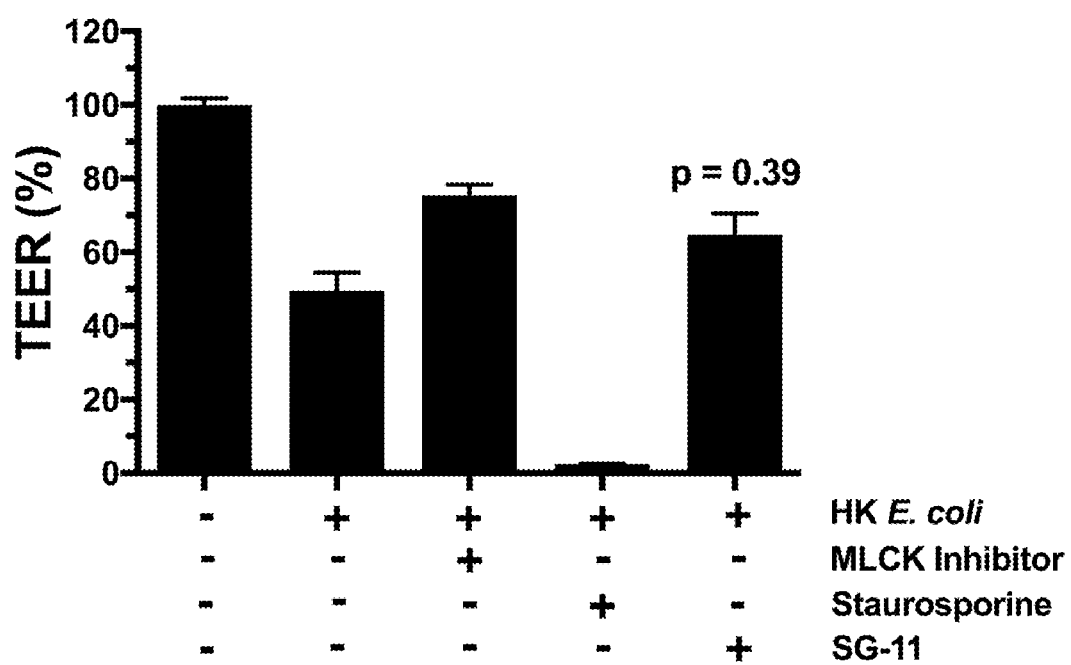

SG-11 protein was added 1 hour (FIG. 1A) or 6 hours (FIG. 1B) prior to exposure of both epithelial cells and monocytes to heat killed *Escherichia coli* (HK *E. coli*), inducing monocytes to produce inflammatory mediators resulting in disruption of the epithelial monolayer as indicated by a reduction in TEER. A myosin light chain kinase (MLCK) inhibitor was utilized as a control compound, which has been shown to prevent barrier disruption and/or reverse barrier loss triggered by the antibacterial immune response. Staurosporine was used as a control compound that caused epithelial cell apoptosis and/or death, thus resulting in a drastic decrease in TEER, which indicates disruption and/or loss of epithelial cell barrier integrity/function. In FIG. 1A, SG-11 increased TEER from 55.8% disruption by HK *E. coli* to 62%. In FIG. 1B, SG-11 increased TEER from a 53.5% disruption by HK *E. coli* to 60.6%. The graphs in FIGS. 1A-1B represent data pooled from two individual experiments (n=6).

Example 3

Effects of SG-11 on TNF-α and IL-23 Production Induced by Heat Killed *Escherichia coli*

The following experiment demonstrates the therapeutic ability of a SG-11 protein or variant thereof as disclosed herein to reduce immune activation as measured by cytokine production. The experiment thereby demonstrates potential functional utility of the therapeutic protein to treat a gastrointestinal inflammatory disease, or disease involving impaired epithelial barrier integrity/function, where modulation of cytokine levels would affect the disease state in a host.

Production of the pro-inflammatory cytokines TNF-α and IL-23 by monocytes was measured in the tissue culture supernatant from the basolateral chamber of the co-culture TEER assay performed in Example 2. Following TEER readings, the supernatants were centrifuged at 10,000 g for 5 minutes at 4° C. to remove cell debris. Luminex analysis was performed according to the manufacturer's instructions (MAGPIX® instrument and xPONENT® software version 4.2; Luminex Corporation (Austin, Tex.)). Luminex analysis was performed to determine the μg/ml concentration of TNF-α and IL-23 produced by monocytes. Luminex analysis utilizes a bead-based system for quantification of multiple cytokines from a single sample. Like an ELISA, Luminex beads are coated with a capture antibody, and incubation with samples allows the target to bind to the capture antibody. Beads are washed and incubated with a fluorescently labeled detection antibody for quantification of bound target. Cytometric analysis is used to differentiate bead populations, which are loaded with differential fluorescent dyes, and to quantify cytokine levels by measuring detection antibody signal.

Figure 2A:
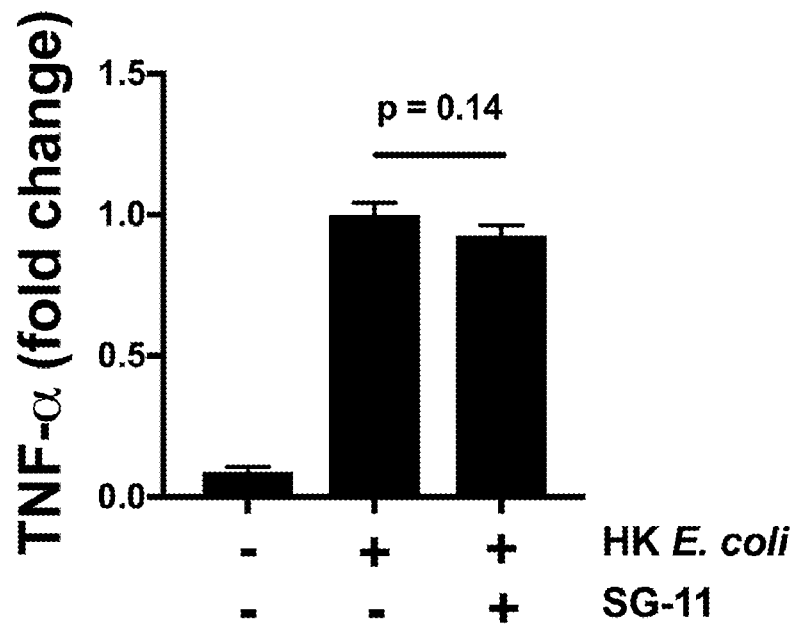
FIG. 2A shows effects of SG-11 administration on TNF-α production induced by heat killed *Escherichia coli* (HK *E. coli*), as described in Example 3.
Figure 2B:
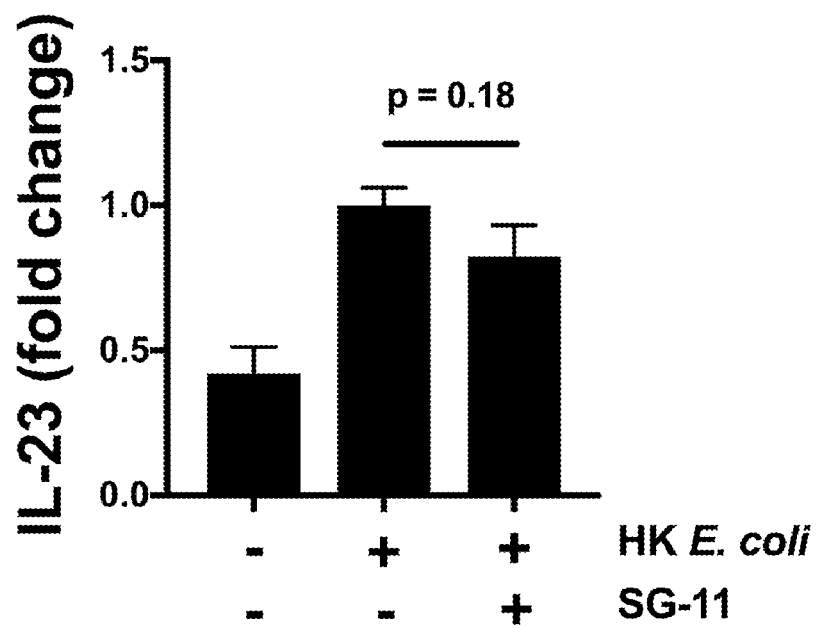
FIG. 2B shows effects of SG-11 administration on IL-23 production induced by HK *E. coli*, as described in Example 3.

TNF-α and IL-23 production in untreated cells and cells pre-incubated with SG-11 for 6 hours prior to HK *E. coli* treatment were normalized to μg/ml concentrations elicited by HK *E. coli* which was set to 1.0. Pre-incubation with SG-11 reduced both TNF-α and IL-23 production. Results are shown in FIG. 2A (TNF-α) and FIG. 2B (IL-23). The graphs in FIG. 2A and FIG. 2B represent data pooled from two individual experiments (n=6).

Example 4

Effect of SG-11 on IL-10 Production Induced by Heat Killed *Escherichia coli*

The following experiment measures effects of SG-11 administration on IL-10 production in a TEER assay.

Figure 3:
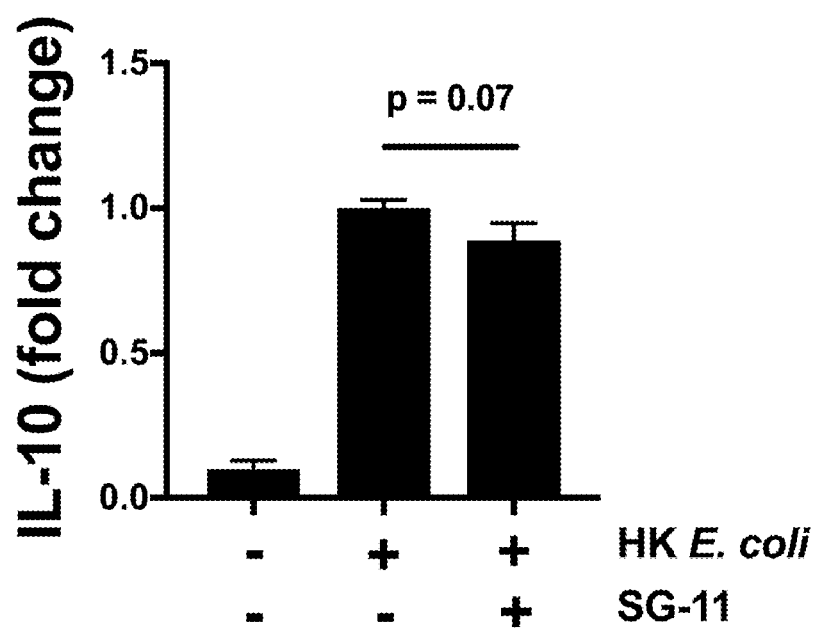
FIG. 3 shows effects of SG-11 administration on IL-10 production induced by HK *E. coli*, as described in Example 4.

IL-10 production was measured in tissue culture supernatant from the basolateral chamber of the co-culture TEER assay described in Example 2 containing monocytes. Luminex analysis was performed to determine the μg/ml concentration of IL-10 produced by the monocytes. IL-10 production in untreated cells and cells pre-incubated with SG-11 for 6 hours prior to HK *E. coli* treatment were normalized to μg/ml concentrations elicited by HK *E. coli* which was set to 1.0. Pre-incubation with SG-11 reduced IL-10 production to 0.89. Results are shown in FIG. 3. The graph in FIG. 3 represent data pooled from two individual experiments (n=6).

Example 5

Effects of SG-11 on Mucin Expression Following Stimulation with Heat Killed *Escherichia coli*

The following experiment measures effects of a SG-11 protein or variant thereof as disclosed herein to increase mucin expression in gastrointestinal tissue. The experiment is therefore a demonstration of the functional utility of the therapeutic protein SG-11 to treat a gastrointestinal inflammatory disease, or disease involving impaired epithelial barrier integrity/function, where increased mucin expression would be beneficial.

Gene expression was measured in the epithelial cell monolayer from the apical chamber of the co-culture TEER assay described in Example 2. Total RNA was isolated from the epithelial cell monolayer, cDNA was synthesized. qRT-PCR was performed on cDNA generated from the HCT8 & HT29-MTX cells treated with SG-11 (1 μg/ml; 40 nM) for 6 hours prior to addition of HK E. coli for 24 hours. muc2 gene expression is graphed as mean fold change ±SEM. Statistical analysis was performed by a one-way ANOVA compared to HK E. coli and a Fishers LSD test was used for multiple comparisons.

Figure 4:
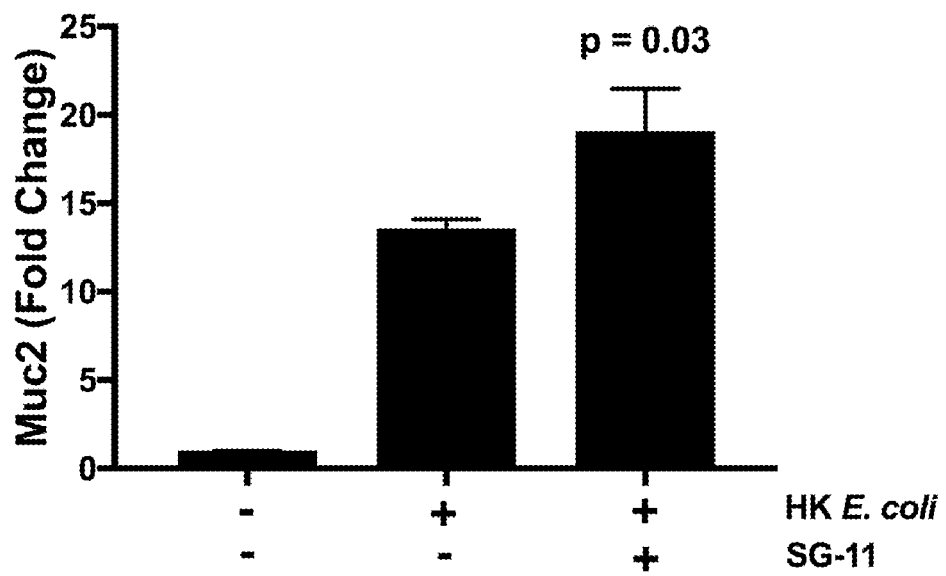
FIG. 4 shows effects of SG-11 administration on mucin expression following stimulation with HK *E. coli*, as described in Example 5.

Analysis of muc2 gene expression revealed that HK E. coli treatment alone resulted in a 13.6-fold increase over untreated cells (p=0.0007). Cells stimulated with HK E. coli and treated with SG-11 had an additional 1.4-fold increase above HK E. coli (p=0.03) (FIG. 4). The graph in FIG. 4 represents data from a single experiment (n=3). A significant increase in muc2 production was observed in response to HK E. coli.

Example 6

Effects of SG-11 on Epithelial Cell Wound Healing

The following experiment demonstrates the therapeutic ability of a protein as disclosed herein to increase gastrointestinal epithelial cell wound healing. The experiment is therefore a demonstration of the functional utility of the therapeutic protein SG-11 to treat a gastrointestinal inflammatory disease, or disease involving impaired epithelial barrier integrity/function, where increased epithelial cell wound healing would be beneficial.

The 96 well Oris Cell Migration assay containing plugs preventing cell attachment in the center of each well was used according to the manufacturer's instructions (Platypus Technologies, Madison, Wis.).

The migration assay plates were warmed to room temperature prior to use and plugs were removed from 100% confluence wells prior to cell addition. The HCT8 enterocyte and HT29-MTX goblet cell lines were used at a 9:1 ratio with a total of $5 \times 10^4$ total cells added per well ($4.5 \times 10^4$ HCT8 cells and $0.5 \times 10^4$ HT29-MTX cells). Cells were incubated at 37° C.+5% $CO_2$ for 24 hours. Plugs were then removed from all control and sample wells. Control wells included cells treated with the diluent vehicle as the blank, 30 ng/ml epidermal growth factor (EGF) as the positive control, and 100 nM staurosporine as the negative control, all diluted in cRPMI. Sample wells contained SG-11 protein (SEQ ID NO:5 and/or SEQ ID NO:9) at a concentration of 1 μg/ml diluted in cRPMI. 100% and 0% wells were cultured in cRPMI. Treatments were added to cells and incubated at 37° C.+5% $CO_2$ for 48 hours. Prior to staining for viable cells, plugs were removed from the 0% wells. Treatment media was removed and cells were washed in PBS containing 0.9 mM $CaCl_2$) and 0.5 mM $MgCl_2$. The green fluorescent viability dye Calcenin AM was added to all wells at a concentration of 0.5 μg/ml in PBS containing 0.9 mM $CaCl_2$) and 0.5 mM $MgCl_2$, incubated for 30 min at 37° C.+5% $CO_2$, the dye was removed and cells were washed in PBS containing 0.9 mM $CaCl_2$) and 0.5 mM $MgCl_2$ and fluorescence was measured. Relative fluorescent values from 100% wells where plugs were removed prior to cell plating were set as the max effect, and 0% wells where plugs remained in place until immediately before staining were used as the baseline. Samples were normalized between 100% and 0% samples and values expressed as a percent growth.

Figure 5:
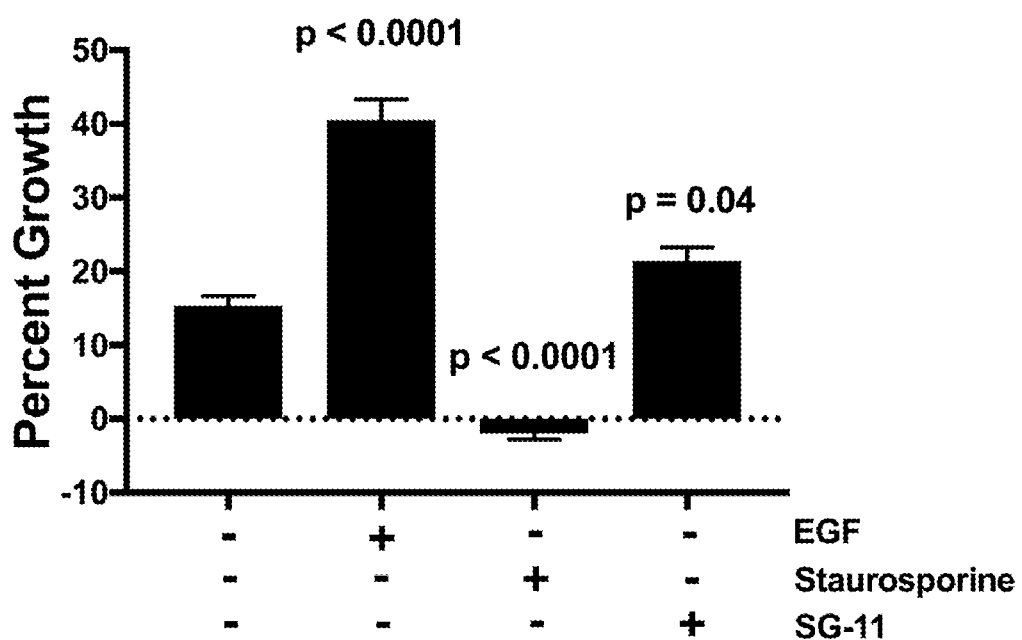
FIG. 5 shows effects of SG-11 administration on epithelial cell wound healing, as described in Example 6.

As shown in FIG. 5, a significant increase in growth was observed upon treatment with SG-11. Control compounds modulated wound healing as expected with EGF increasing proliferation, and staurosporine suppressing cell proliferation. The graph in FIG. 5 represents data pooled from 5 experiments (n=15). The data represent 5 independent replicate experiments wherein SG-11 SEQ ID NO:5 was used in 1 experiment and SEQ ID NO:9 was used in 4 experiments.

Example 7

SG-11 Demonstrates Therapeutic Activity in a Concurrent DSS Model of Inflammatory Bowel Disease Examples 7 and 8 demonstrate the ability of a protein as disclosed herein to treat inflammatory bowel disease in an in vivo model. The experiment is therefore a demonstration that the aforementioned in vitro models, which described important functional and possible mechanistic modes of action, will translate into an in vivo model system of inflammatory bowel disease. Specifically, the mice in Examples 7 and 8 were treated with dextran sodium sulfate (DSS), a chemical known to induce intestinal epithelial damage and thereby reduce intestinal barrier integrity and function. DSS mice are well-accepted models of colitis. In Example 7, mice were treated with SG-11 protein approximately concurrent with (6 hours prior to) administration of DSS. In Example 8, mice were treated with DSS for 6 days prior to treatment with SG-11 protein.

The graphs presented in Example 7 represent data pooled from 3 independent experiments, each using 10 mice (n=30). The SG-11 protein used in these experiments was the mature protein (no signal peptide) without an N-terminal tag and comprising the amino acid sequence of SEQ ID NO:3. For 2 experiments, the SG-11 protein consisted of SEQ ID NO:5; for the third experiment, the SG-11 protein consisted of SEQ ID NO:7.

Eight-week old C57BL/6 mice were housed 5 animals were cage and given food and water ad libitum for 7 days. Following the 7-day acclimation period, treatments were initiated concurrently with addition of 2.5% DSS to the drinking water. Preliminary tracking studies with fluorescently labeled bovine serum albumin following intraperitoneal (i.p.) injection of protein demonstrated proteins reached the colon at 6 hours after i.p. delivery. Based on these results, 6 hr prior to addition of 2.5% DSS to the drinking water mice were treated with 50 nmoles/kg SG-11 (1.3 mg/kg) or Gly2-GLP2 (0.2 mg/kg) i.p. Six hours after the initial treatment the drinking water was changed to water containing 2.5% DSS. The mice were treated with 2.5% dextran sodium sulfate (DSS) in their drinking water for 6 days. Treatments were continued with SG-11 or Gly2-GLP2 twice a day (b.i.d.) in the morning and evening (every 8 and 16 hr) with i.p. injections at 50 nmoles/kg. Fresh 2.5% DSS drinking water was prepared every 2 days.

Figure 6:
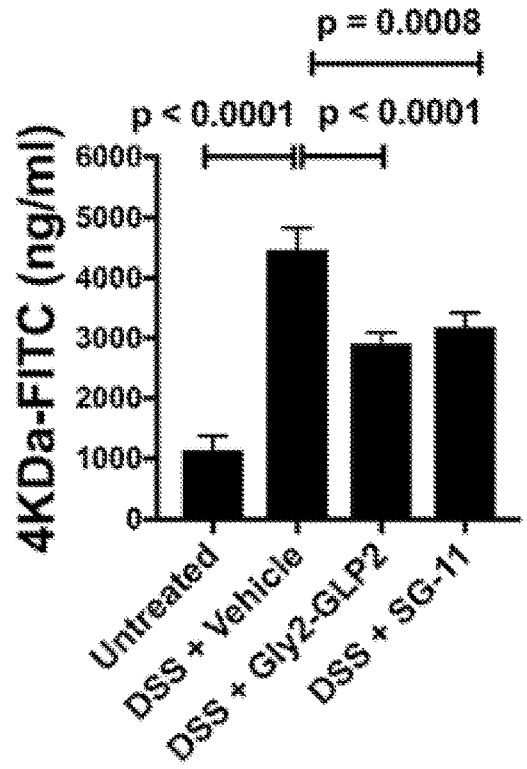
FIG. 6 shows effects of SG-11 administration on epithelial centric barrier function readouts in a DSS model of inflammatory bowel disease, as described in Example 7.

On day six, mice were fasted for four hours and then orally gavaged with 600 mg/kg 4KDa dextran labeled with fluorescein isothiocyanate (FITC) [4KDa-FITC]. One hour after the 4KDa-FITC gavage mice were euthanized, blood was collected and FITC signal was measured in serum. A significant increase in 4KDa-FITC dextran translocation across the epithelial barrier was observed in untreated mice, in comparison to vehicle treated DSS mice. Additionally, a significant reduction in 4KDa-FITC dextran was observed in mice receiving DSS and treated with SG-11, as compared to DSS mice treated with vehicle. The magnitude of 4KDa-FITC dextran translocation observed for SG-11 was similar to the positive control of Gly2-GLP2. Results are shown in FIG. 6, and are presented as mean f SEM. The graph in FIG. 6 represents data pooled from 3 independent experiments (n=30).

Figure 7:
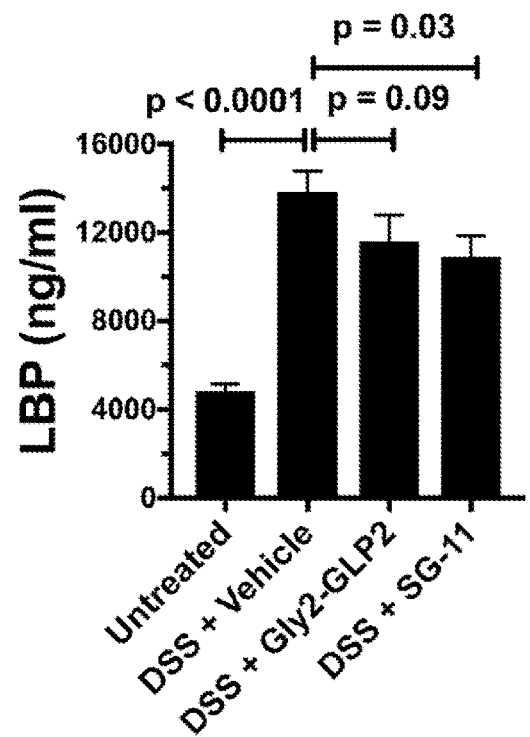
FIG. 7 shows effects of SG-11 administration on inflammatory readouts responsive to impaired barrier function in a DSS model of inflammatory bowel disease, as described in Example 7.

SG-11 Improves Inflammation Centric Readouts of Barrier Function in a Concurrent DSS Model of Inflammatory Bowel Disease SG-11 was also assessed for its effects on the levels of LPS binding protein (LBP) in the blood of the DSS animal with and without SG-11 administration. LPS binding protein (LBP), which has been linked to clinical disease activity in subjects with inflammatory bowel disease, was also measured by ELISA in the serum of mice tested in the DSS model described in Example 7. A significant increase in LBP concentration was observed in response to DSS. Additionally, a significant reduction in LBP was observed in SG-11 treated mice given DSS as compared to DSS mice treated with vehicle. Furthermore, SG-11 had a greater impact on LBP concentration as compared to the control peptide Gly2-GLP2, as a significant difference between DSS mice treated with Gly2-GLP2 and DSS mice treated with SG-11 was observed. Results are shown in FIG. 7, and are presented as mean SEM. The graph in FIG. 7 represents data pooled from 3 independent experiments (n=30).

SG-11 Prevents Weight Loss in a Concurrent DSS Model of Inflammatory Bowel Disease Also assessed was the therapeutic ability of a protein as disclosed herein to ameliorate weight loss in an animal suffering from an inflammatory intestinal disorder. Weight loss is a significant and potentially dangerous side effect of inflammatory bowel disease.

Figure 8:
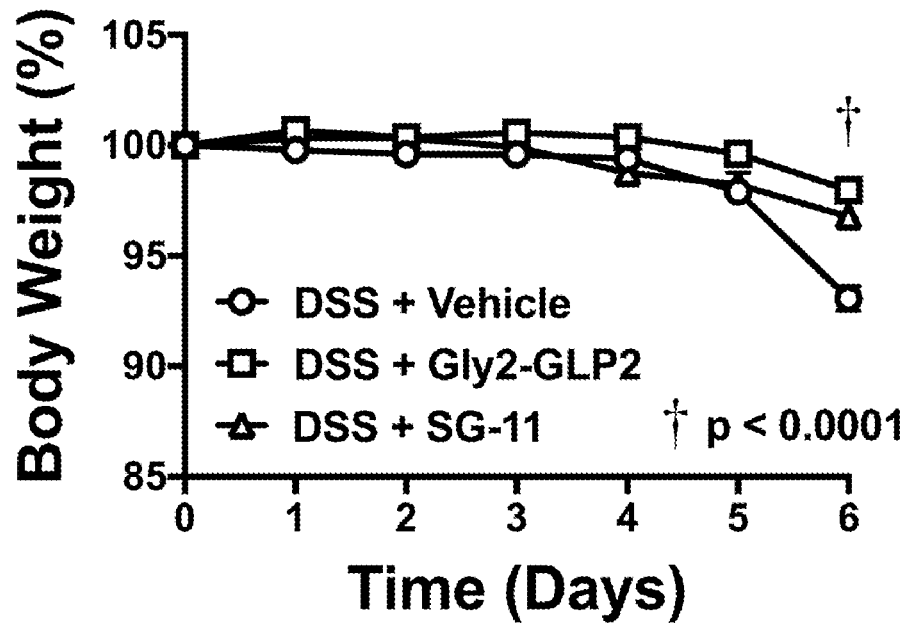
FIG. 8 shows effects of SG-11 administration on body weight in a DSS model of inflammatory bowel disease, as described in Example 7.

Body weight was measured daily from mice included in the DSS model described in this Example. Percent change from starting weight on day 0 was determined for each mouse. SG-11 administration to DSS treated mice significantly improved body weight as compared to vehicle treated DSS mice. Weight loss in mice treated with SG-11 at day 6 was similar to weight loss observed with Gly2-GLP2. Results are shown in FIG. 8. The graph in FIG. 8 represents data pooled from two independent experiments (n=20).

Figure 9:
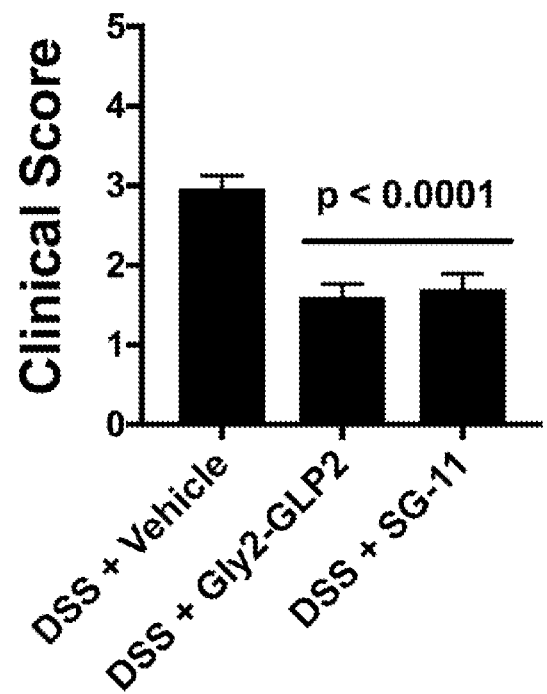
FIG. 9 shows effects of SG-11 administration on gross pathology in a DSS model of inflammatory bowel disease, as described in Example 7.

SG-11 Significantly Reduces Gross Pathology in a DSS Model of Inflammatory Bowel Disease Gross pathology observations were made in mice included in the concurrent DSS model performed in this Example. SG-11 administration to DSS treated mice significantly improved gross pathology as compared to vehicle treated DSS mice. No differences in clinical scores were observed between mice given DSS and treated with either Gly2-GLP2 or SG-11. The scoring system used was: (0)=no gross pathology, (1)=streaks of blood visible in feces, (2)=completely bloody fecal pellets, (3) bloody fecal material visible in cecum, (4) bloody fecal material in cecum and loose stool, (5)=rectal bleeding. Results are shown in FIG. 9. The graph in FIG. 9 represents data pooled from 3 independent experiments (n=30). These data show that SG-11 is therapeutically effective in improving symptoms of IBDs such as blood in the feces.

Figure 10A:
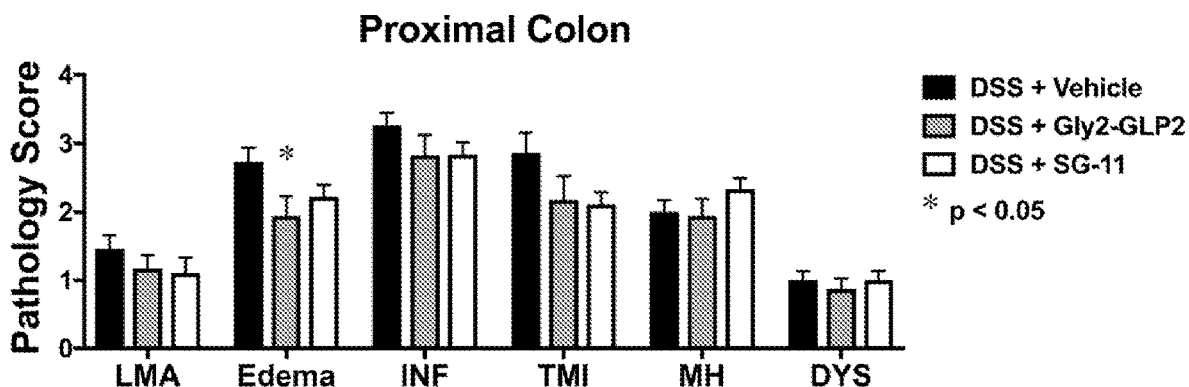
FIGS. 10A, 10B and 10C show results from histopathology analysis of proximal (FIG. 10A), distal (FIG. 10B) and both proximal and distal (FIG. 10C) tissue from a DSS model of inflammatory bowel disease, as described in Example 7.
Figure 10B:
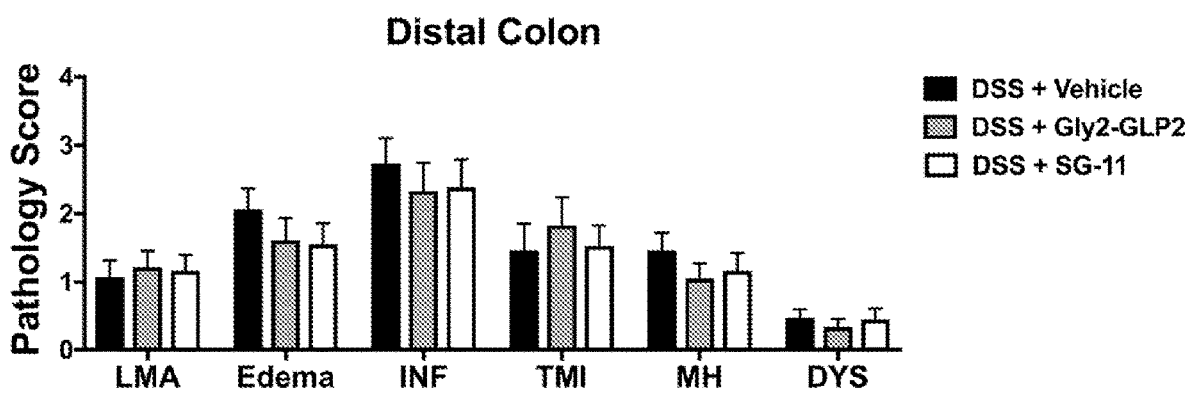
Figure 10C:
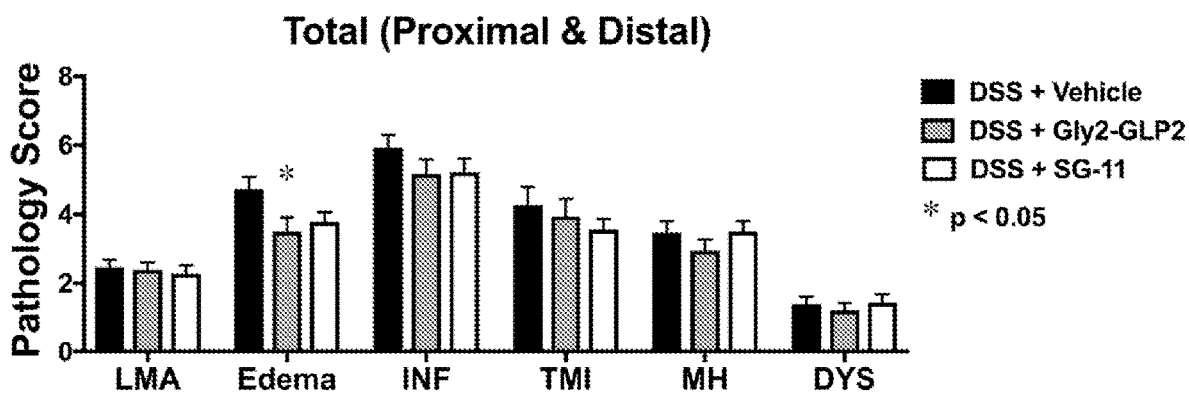

In addition, histopathology analysis was performed on proximal and distal colon tissues from the DSS model animals. Proximal (FIG. 10A) and distal (FIG. 10B) colon scores (range 0-4) are presented as well as the total score (FIG. 10C) for the colon which represents the sum of proximal and distal colon scores (scored on a scale of 0-8). LMA=Loss of mucosal architecture, Edema=Edema, INF=Inflammation, TMI=Transmural inflammation, MH=Mucosal hyperplasia, DYS=Dysplasia. Graphs represent data pooled from two independent experiments, and are plotted as mean SEM. Statistical analysis was performed by a one-way ANOVA compared to DSS+vehicle followed by a Fisher's LSD test for multiple comparisons.

SG-11 Minimizes the Colon Shortening Effect in Response to DSS Treatment

The following experiment demonstrates the therapeutic ability of a protein as disclosed herein to treat inflammatory bowel disease in an in vivo model, by showing an ability to prevent or minimize colon shortening.

Figure 11A:
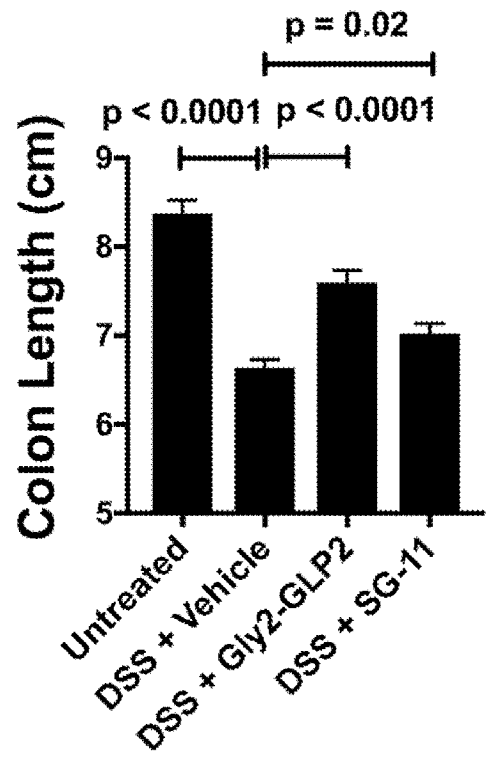
FIG. 11A shows effects of SG-11 administration on colon length in a DSS model of inflammatory bowel disease, as described in Example 7.
Figure 11B:
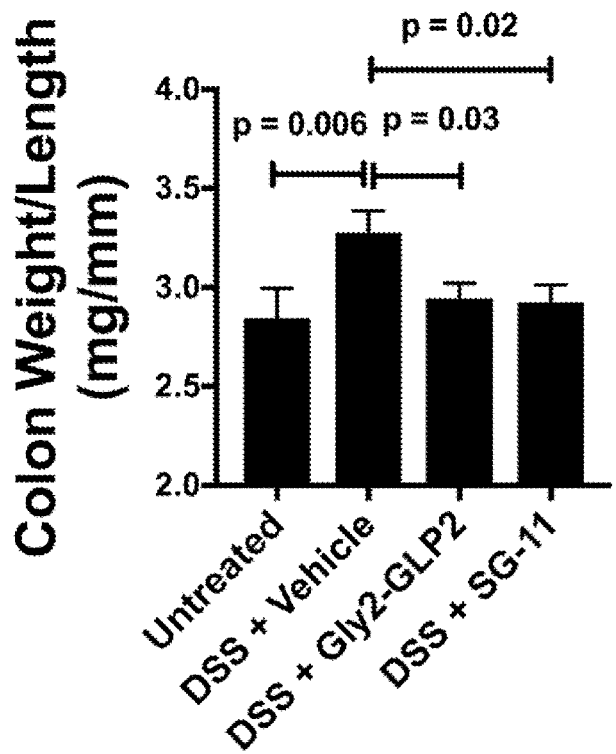
FIG. 11B shows effects of SG-11 administration on colon weight-to-length ratio in a DSS model of inflammatory bowel disease, as described in Example 7.

Colon length was measured in mice included in the DSS model described in Example 7. SG-11 administration to DSS treated mice prevented colon shortening elicited by DSS. A significant improvement in colon length was observed with Gly2-GLP2 and Gly2-GLP2 treatment had a significant improvement over SG-11 treatment. Results are shown in FIG. 11A. Additionally, treatment of mice exposed to DSS with either Gly-2-GLP2 or SG-11 resulted in a significant improvement in colon weight to length ratios (FIG. 11B). The graphs in FIGS. 11A and 11B represent data pooled from 3 independent experiments (n=30). Data are graphed as mean±SEM and are pooled from three independent experiments (n=30). Statistical analysis was performed by a one-way ANOVA followed by a Fisher's LSD multiple comparisons test.

Example 8

SG-11 Demonstrates Therapeutic Activity in a DSS Model of Inflammatory Disease

In this example, experiments were performed to study the effects of SG-11 in the DSS mouse model when the SG-11 protein is administered to the mice after DSS treatment for 7 days. This differs from the treatment regimen of Example 7 above in which mice were administered SG-11 protein shortly before treatment with DSS. This example further demonstrates the therapeutic ability of a protein as disclosed herein to treat inflammatory bowel disease in an in vivo model and is therefore a demonstration that the aforementioned in vitro models, which described important functional and possible mechanistic modes of action, will translate into an in vivo model system of inflammatory bowel disease.

Eight-week-old male C57BL/6 mice were housed 5 animals per cage and given food and water ad libitum for seven days. Following a 7-day acclimation period, the mice were provided with drinking water containing 2.5% DSS for 7 days. Fresh 2.5% DSS water was prepared every 2 days during the 7 day DSS administration. For this therapeutic DSS study, SG-11 used to treat the animals was fused at its N-terminus to a FLAG Tag (DYKDDDDK; SEQ ID NO:31).

On day 7 normal drinking water was restored and i.p. treatments of 50 nmole/kg of SG-11 (1.3 mg/kg) or Gly2-GLP2 (0.2 mg/kg) were initiated. Treatments were administered twice a day (b.i.d.), with a morning and evening dose (every 8 and 16 hours) for six days.

As detailed below, results of the treatments were analyzed with respect to animal health including body weight and gross pathology, histopathology of colon tissue, assessment of barrier disruption, and levels of LPS binding protein.

Body weight was measured daily during the morning treatment The colon tissue was then harvested and length was measured in centimeters and the tissue was weighed. Fecal material was flushed from the colon and residual PBS removed by gently running the colon tissue through a pair of forceps. The colon tissue was then weighed and colon weight to length ratio in mg/mm was determined. Following weight measurements proximal and distal colon tissue was banked for RNA and protein analysis and the remaining tissues was fixed in 10% neutral buffered formalin for histopathology. Statistical analysis was performed by a one-way ANOVA compared to DSS+vehicle for serum 4KDa-FITC translocation, serum LBP concentrations, colon length, and colon weight to length ratio, while a two-way ANOVA was performed for analysis of body weight In all analysis, a Fisher's LSD test for multiple comparisons was used. Graphs represent data pooled from two experiments, and are plotted as mean f SEM.

Figure 12:
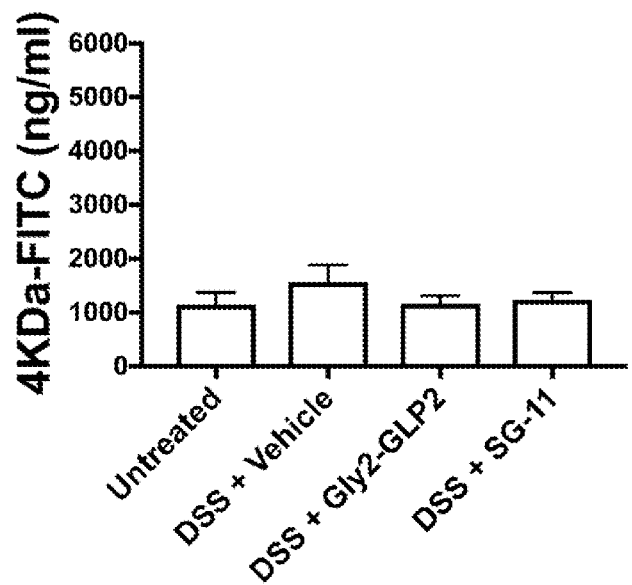
FIG. 12 shows epithelial barrier integrity following SG-11 treatment of a DSS model of inflammatory bowel disease, as described in Example 8.
Figure 13:
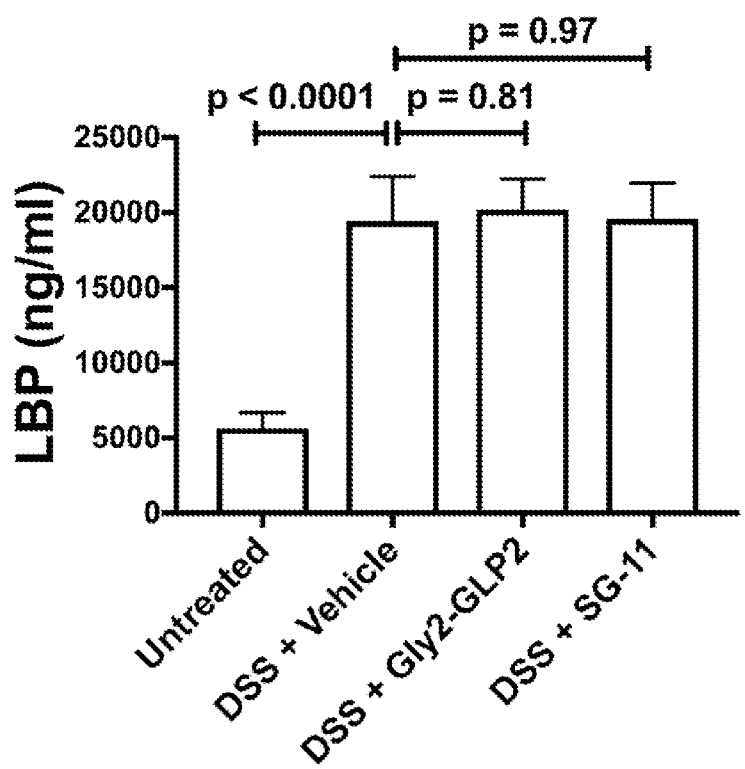
FIG. 13 shows inflammation centric readouts of barrier function in a DSS model of inflammatory bowel disease, as described in Example 8.

This therapeutic model measured recovery of an established DSS insult. Because untreated mice also recover following removal of DSS from the drinking water no increase in 4KDa-FITC signal as observed following 6 days of DSS treatment (FIG. 12). Furthermore, no reduction in LBP was observed following Gly2-GLP2 or SG-11 treatment (FIG. 13). Therefore, no changes in barrier function readouts were observed in the therapeutic model of DSS.

Figure 14:
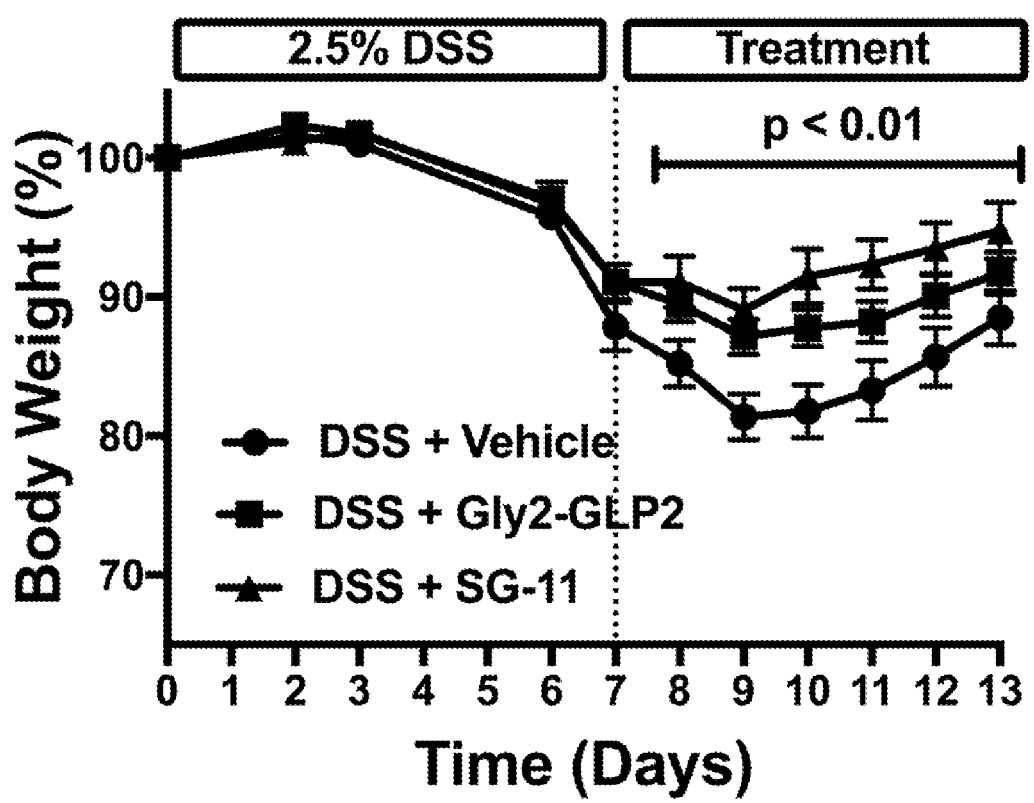
FIG. 14 shows prevention of weight loss in a DSS model of inflammatory bowel disease, as described in Example 8.
Figure 15A:
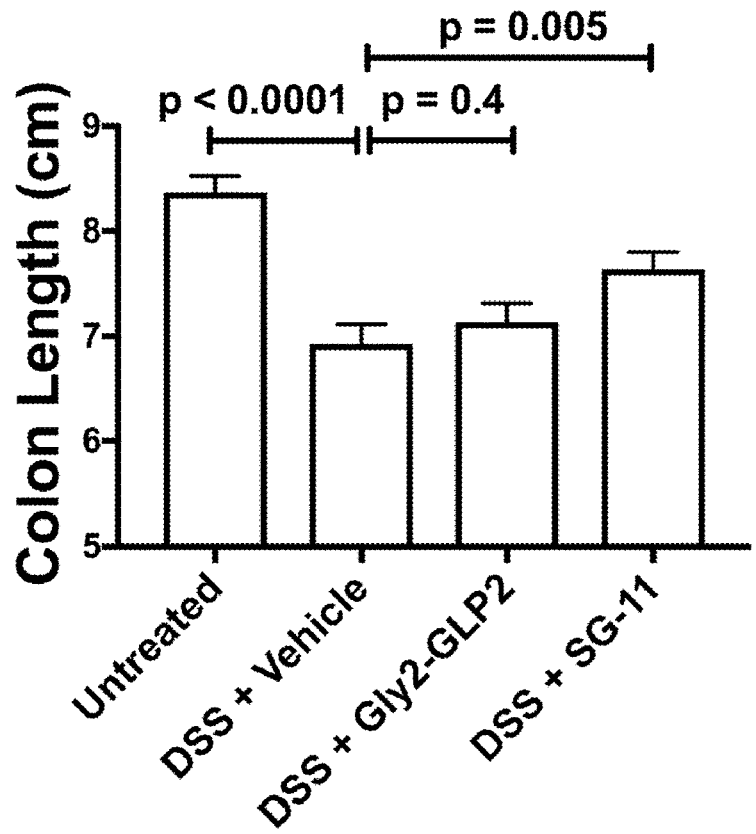
FIG. 15A shows effects of SG-11 administration on colon length in a DSS model of inflammatory bowel disease, as described in Example 8.
Figure 15B:
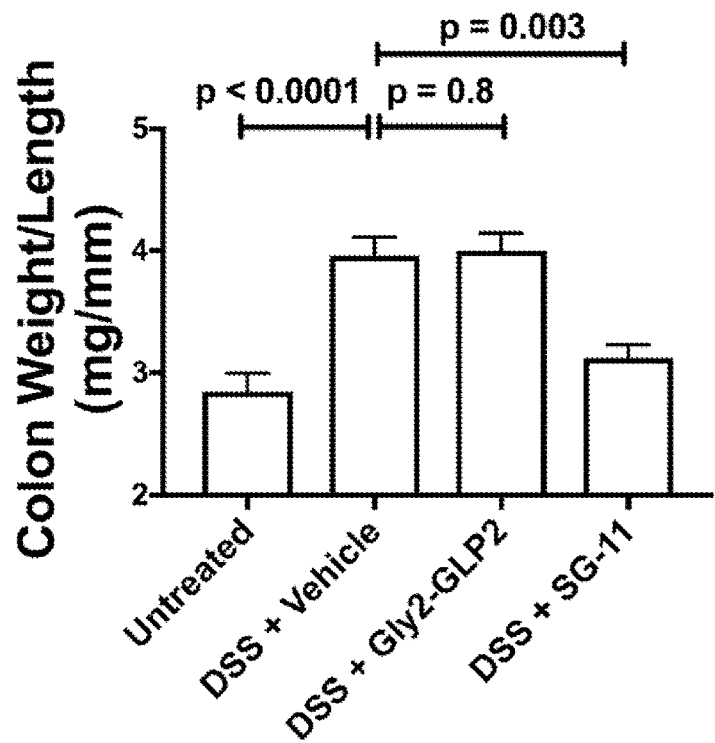
FIG. 15B shows effects of SG-11 administration on colon weight-to-length ratio in a DSS model of inflammatory bowel disease, as described in Example 8.

Although no changes in barrier function readouts were observed in the therapeutic DSS model, significant improvements in clinical parameters such as body weight (FIG. 14), colon length (FIG. 15A), and colon weight to length (FIG. 15B) were observed. Similar to barrier readouts, the gross pathology scoring system based on bloody feces was no longer relevant as even DSS mice had recovered following 6 days of treatment. However, while there was no visible blood remaining in the colon, a thickened colon was still observed. From gross pathology observations, a reduction in the frequency of thick colons was observed with SG-11 treatment (88% in DSS+vehicle and 25% in DSS+SG-11, p<0.0001 by Fisher's Exact test, data not shown).

Figure 16A:
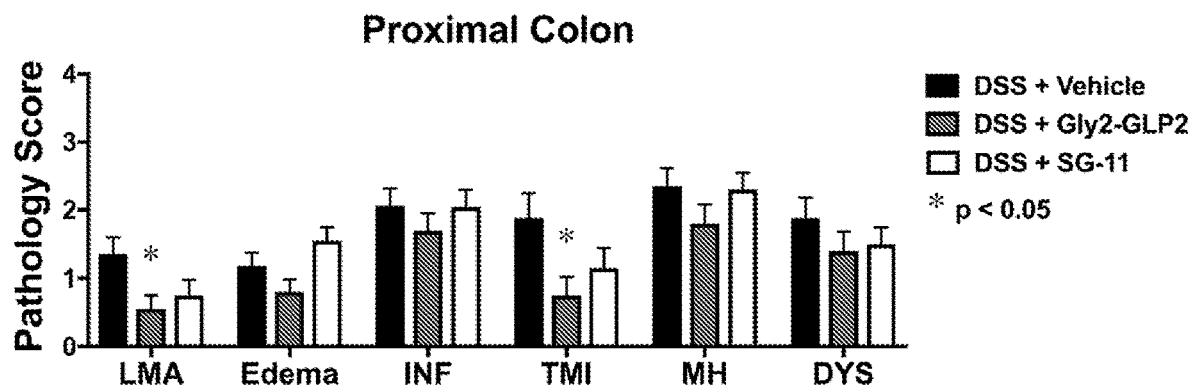
FIGS. 16A, 16B and 16C show results from histopathology analysis of proximal (FIG. 16A), distal (FIG. 16B) and both proximal and distal (FIG. 16C) tissue from a DSS model of inflammatory bowel disease, as described in Example 8.
Figure 16B:
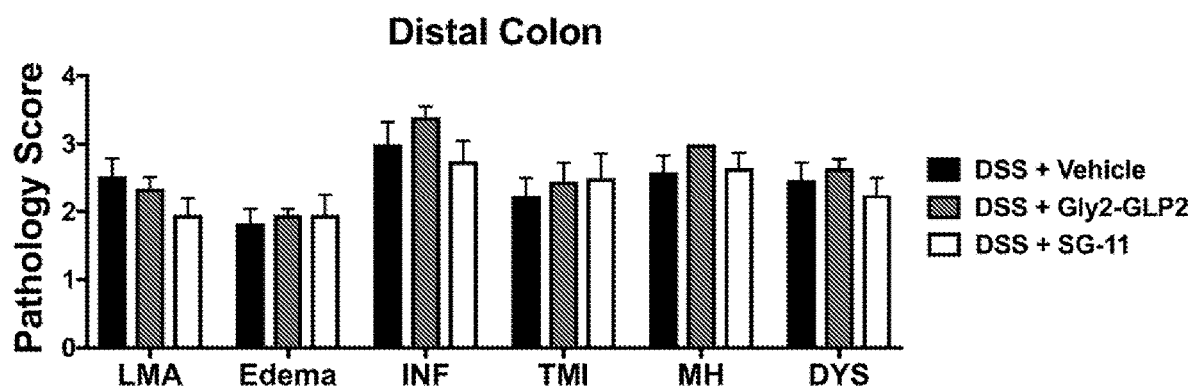
Figure 16C:
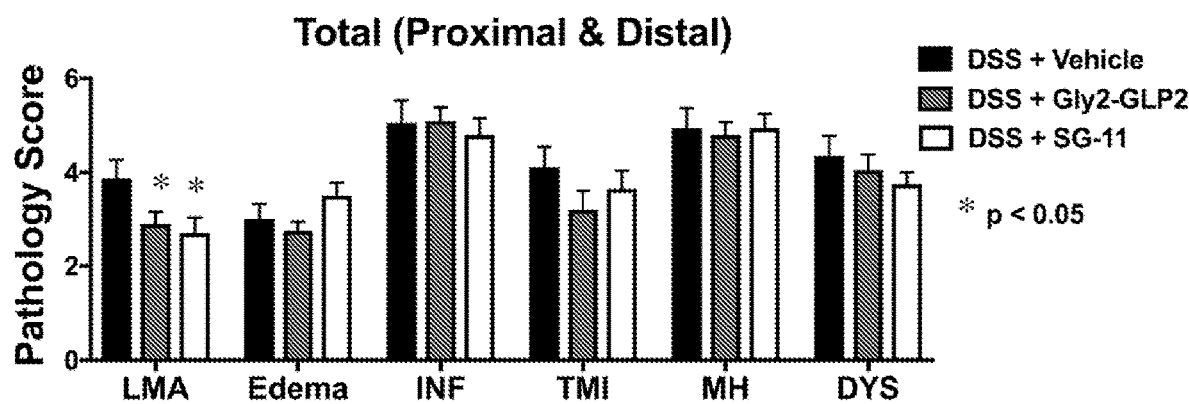

Histopathology analysis was performed on proximal and distal colon tissues from the therapeutic DSS model described above. Proximal (FIG. 16A) and distal (FIG. 16B) colon scores (range 0-4) are presented and as well as the total score for the colon which represents the sum of proximal and distal colon scores (Range 0-8) (FIG. 16C). LMA=Loss of mucosal architecture, Edema=Edema, INF=Inflammation, TMI=Transmural inflammation, MH=Mucosal hyperplasia, DYS=Dysplasia. Graphs represent data pooled from two independent experiments, and are plotted as mean SEM. Statistical analysis was performed by a one-way ANOVA compared to DSS+vehicle followed by a Fisher's LSD test for multiple comparisons.

SG-11 and Gly2-GLP2 treatment resulted in a modest, but significant, reduction in the loss of mucosal architecture score, with no change in inflammation and transmural inflammation scores. Similar to the results provided in Example 7, similar patterns of histopathology changes were observed with SG-11 and Gly2-GLP2, providing additional evidence that SG-11 may target epithelial cells.

Example 9

Design of Stable and Therapeutically Active SG-11 Variants

SG-11 is a therapeutic protein derived from the commensal bacterium *Roseburia hominis*. Administration of *R. hominis* as a probiotic in the DSS model demonstrated efficacy with improvements in intestinal barrier function (4KDa-FITC and LBP), body weight, and clinical score (data not shown).

Post-translational modifications (PTMs) can affect recombinant production of a therapeutic protein can also be affected by post-translational modifications (PTMs) which may occur during large-scale expression and purification as well as during long-term storage. Such PTMs include but are not limited to oxidation of methionine, deamidation of asparagine and inter- and/or intra-molecular disulfide bonds between two cysteines. In an effort to reduce PTM risks, modifications of SG-11 were made by replacing residues which may affect protein stability. Studies describing improved protein stability and maintenance of in vitro and in vivo activity are described in Examples 9-14.

As a first step, the SG-11 amino acid sequence (SEQ ID NO:7) was aligned to similar prokaryotic proteins. The identified residues based on the search results can be used for the amino acid substitution for enhancing the stability of the therapeutic protein(s).

At first, a Blast search of the GenBank non-redundant protein database (NCBI BLAST/default parameters/BLOSUM62 matrix) was performed to identify other prokaryotic proteins that may be homologous to SG-11. The identified protein sequences are shown in FIG. 17. SEQ ID NO:21 is a hypothetical protein from *Roseburia intestinalis* (GenBank: WP_006857001.1; BLAST E value: 3e-90); SEQ ID NO:22 is a hypothetical protein from *Roseburia* sp. 831b (GenBank:WP_075679733.1; BLAST E value: 4e-58); and SEQ ID NO:23 is a hypothetical protein from *Roseburia inulinivorans* (GenBank: WP_055301040.1; BLAST E value: le-83).

Each of SEQ ID NO:21, SEQ ID NO:22 and SEQ ID NO:23 is a predicted mature form of the indicated protein (lacks a signal peptide) and contains an N-terminal methionine. A multiple sequence alignment of these sequences with SG-11 (SEQ ID NO:7) was performed to identify regions conserved among the proteins. The alignment is shown in FIG. 17. The alignment was used to identify residues which were most conserved among the different proteins in order to assess the potential impact of substituting a particular amino acid(s). Portions of the SG-11 are somewhat or highly conserved in which an amino acid at a particular position in the protein is identical in all 4 of the aligned proteins or at least in 2 (positions) or 3 (positions) of the 4 proteins. The high sequence conservation among these homologs of SG-11 suggests that SEQ ID NO:21, SEQ ID NO:22 and SEQ ID NO:23 may also possess a function important in maintaining a healthy epithelial barrier. Thus, the disclosure provides for methods of utilizing SEQ ID NOs 21-23 for treating diseases of the disclosure, and methods of making same.

Example 10

Post-Translational Modification (PTM) Analysis of SG-11

Studies were performed to identify residues of SG-11 particularly susceptible to PTMs using LC/MS/MS. The analysis was performed by LakePharma (Belmont, Calif.) to 1) confirm the amino acid sequence of SG11 (SEQ ID NO:9), and 2) determine any post-translational modification which could lead to reduced biological activity and immunogenicity, particularly deamidation and oxidation.

For peptide mapping and PTM analysis, samples were treated with DTT and IAA, followed by trypsin digestion. The digested sample was then analyzed by Waters ACQUITY UPLC coupled to XEVO® G2-XS QTOF mass spectrometer using a Protein BEH C18 column.

Peptide mapping and sequencing confirmed the predicted amino acid sequence and also indicated multiple deamidation sites and one oxidation site. Among them, 7.84% of N53 and 3.77% N83 is deamidated. These results presented in Table 6 indicate that N53 and N83 are primary sites of deamidation under non-stress conditions. N53 indicates Asparagine (Asn; N) located at the 53th position in mature SG-11 with a methionine at the first position (SEQ ID NO:7).

TABLE 6

Post-Translation Modification of SG-11

| Amino Acid[1] | SEQ ID NO | Peptide | Modifiers | % total ion[2] | % peptide[3] |
|---|---|---|---|---|---|
| N53 | 30 | NAVK | Deamidation | 0.01 | 7.84 |
| N83 | 26 | TREDYTAFNGIELYQGK | Deamidation | 0.25 | 3.77 |
| N137 | 27 | ANTDVK | Deamidation | 0.25 | 1.03 |
| N153 | 28 | VDGEICYVSCQNVK | Deamidation | 0.01 | 0.2 |
| M1 | 24 | MLEGEESVVYVGK | Oxidation | <0.01 | N/A |

[1]Amino acid position in SG-11 (SEQ ID NO: 7)
[2]Normalized to total peptide ion intensity
[3]Normalized to the total intensity of corresponding precursor with or without modification Example 11

Forced degradation of SG-11

SG-11 (SEQ ID NO:9) was also tested under a series of stress conditions shown in Table 7 below to further characterized the stability of recombinant, purified SG-11. Stressed samples were analyzed either by SEC-HPLC for the presence of aggregates and/or degradants. LC/MS/MS was performed for determination of levels of deamidation and oxidation.

TABLE 7

| Stress factor | | Analytic method | Criteria | Observation |
|---|---|---|---|---|
| Temperature (2 weeks) | 4° C. | HPLC | % monomer (>90% pass) | Solution clear |
| | 25° C. | HPLC | % monomer (>90% pass) | Solution clear |
| | 37° C. | HPLC | % monomer | Solution clear |
| | 40° C. | uPLC LC/MS/MS | % monomer | Solution clear |
| Oxidation | Hydroperoxide (0.005%) 40° C., 16 hr | uPLC LC/MS/MS | % oxidation and sites | Solution clear |
| Mechanical stress | 350 rpm shake, 4° C., 24 hr | HPLC | % monomer (>90% pass) | Solution clear |
| pH | pH 4 and pH 9 | uPLC LC/MS/MS | % deamidation sites | Solution clear |
| Freeze and thaw (6 cycles) | −80° C. to room temperature | HPLC | % monomer | Solution clear |

For this analysis, SG-111 (SEQ ID NO:9) was present at a concentration of 1 mg/ml in PBS+10% glycerol (50 mM sodium phosphate, 150 mM NaCl, 10% glycerol, pH 8.0), with the exception of tests under pH 4 and pH 9. For pH 4, SG-11 (SEQ ID NO:9) was prepared at a concentration of 1 mg/ml in sodium acetate buffer (50 mM sodium acetate, 150 mM NaCl, pH 4). For pH 9, SG-11 (SEQ ID NO:9) was prepared at a concentration of 1 mg/ml in CAPSO (3-cyclohexylamino-2-hydroxy-1-propanesulfonic acid) buffer (50 mM CAPSO, 150 mM NaCl, pH 9).

The analysis shows that the SG-11 (SEQ ID NO:9) sample treated at 4° C. has low level of aggregates. With increasing temperature, aggregation increased. At 37° C., major aggregation occurred. In contrast, mechanical stress and repeated freeze and thaw do not cause either protein aggregation or degradation.

Three samples were treated by either incubation at 40° C. for two weeks, oxidation (H$_2$O$_2$ treatment) or high pH 9, respectively, were analyzed by LC/MS/MS for PTMs as described in Example 10. As shown in Table 8 below, significant deamidation of N83 occurred after sample treatment at 40° C. with almost 100% deamidation. Significant deamidation of N83 (37%) and oxidation of M200 (63.9%) were observed in samples treated with hydrogen Peroxide. 7.84% of N53 was deamidated without any treatment.

TABLE 8

| Peptides | Modification[1] | % 40° C. | Oxidation | pH 9 | No treatment |
|---|---|---|---|---|---|
| MLEGEESVVYVGK (SEQ ID NO: 24) | No modification | 99.82 | 99.88 | 99.94 | 99.78 |
| | Oxidation of M | 0.18 | 0.12 | 0.06 | 0.22 |
| GVIASLDVETLDQSYYDETELK (SEQ ID NO: 25) | No modification | 99.91 | 99.93 | 99.95 | 100 |
| | Deamidation Q30 | 0.09 | 0.07 | 0.05 | 0 |
| TPEDYTAFNGIELYQGK (SEQ ID NO: 26) | No modification | 0 | 63 | 80.9 | 82.57 |
| | Deamidation N83 | 99.88 | 37 | 19.1 | 17.43 |

TABLE 8-continued

| Peptides | Modification[1] | 40° C. | Oxidation | pH 9 | No treatment |
|---|---|---|---|---|---|
| | Deamidation N83 Deamidation Q89 | 0.12 | 0 | 0 | 0 |
| ANTDVK (SEQ ID NO: 27) | No modification | 85.39 | 83.56 | 76.05 | 98.96 |
| | Deamidation N137 | 14.61 | 16.44 | 23.95 | 1.04 |
| VDGEICYVSCQNVK (SEQ ID NO: 28) | No modification | 44.85 | 63.23 | 8.76 | 99.98 |
| | Carbamidomethy C147 | 33.59 | 34.52 | 71.71 | NA |
| | Carbamidomethy C151 | 18.45 | 1.93 | 12.45 | NA |
| | Deamidation N153 Deamidation Q152 | 0 | 0 | 0.35 | 0.02 |
| | Deamidation N153 Carbamidomethy C151 | 3.1 | 0.31 | 0.28 | 0 |
| GYYLETGSVTASVDVTGQESVGTE QLSGTEQMEMTGEPVNADDTEQT EAAAGDGSFETDVYTFIVYK (SEQ ID NO: 29) | No modification | 96.38 | 19.17 | 88.16 | 100 |
| | Deamidation N206 Deamidation Q152 Oxidation M | 3.62 | 0 | 11.84 | 0 |
| | Oxidation M198 | 0 | 16.92 | 0 | 0 |
| | Oxidation M200 | 0 | 63.9 | 0 | 0 |
| NAVK (SEQ ID NO: 30) | Deamidation N53 | NA | NA | NA | 7.84 |

[1]Amino acid position in SG-11 (SEQ ID NO: 7)

After reduction, free cysteines were artificially carbamidomethylated by iodoacetamide to block cysteine residues from oxidation in the assays.

Example 12

Cysteine Residues and the Stability of SG-11

The stability of SG-11 (SEQ ID NO:9) was evaluated following the incubation at 37° C. for one week and at 4° C. for 3 weeks in Buffer C (100 mM sodium phosphate, pH 7.0, 0.5 M sorbitol). The stability was assessed by monitoring the aggregation formation with analytical size exclusion chromatography (SEC) equilibrated with Buffer D (100 mM sodium phosphate, pH 7.0, 10% glycerol). No noticeable change was observed after 3 weeks storage at 4° C. compared with the freshly thawed protein as both samples showed a single peak at 1.57 mL. However, after a one-week incubation at 37° C., the sample clearly showed aggregation peaks at 1.29 and 1.41 mL in addition to a monomer peak at 1.57 mL, which was the smallest peak. The cause of the aggregation was investigated as follows. There are two cysteine residues found in SG-11 at the positions 147 and 151 (relative to SEQ ID NO:7). Ellman's reagent assay revealed the presence of free sulfhydryl groups in SG-11 (SEQ ID NO:9), which indicated $Cys^{147}$ and/or $Cys^{151}$ does not form stable disulfide bonds. As free sulfhydryl groups could cause aggregation by forming unpreferable intermolecular disulfide bonds, it was examined whether the presence of reducing agent, such as β-mercaptoethanol, could prevent the aggregation. Aggregation was greatly suppressed in the presence of 2.5% (v/v) β-mercaptoethanol in a buffer (50 mM sodium phosphate, 150 mM NaCl and 10% glycerol) following the 4-days incubation at 37° C., in contrast to the aggregations that were formed without β-mercaptoethanol. The results suggested that $Cys^{147}$ and/or $Cys^{151}$ that provides free sulfhydryl groups that caused aggregation.

Example 13

Post-Translational Modification of an SG-11 Variant

Although SG-11 protein is stable at high temperature, forming aggregations at 37° C. in a week could be problematic during downstream processing stages. Deamidation of asparagine residues found by LC/MS/MS are also a risk factor. In order to improve the manufacturability of a protein comprising SEQ ID NO:3 or variants thereof, the results of Examples 10 to 12 were considered in the design of SG-11 variants (e.g., SG-11V1 (SEQ ID NO:11), SG-11V2 (SEQ ID NO:13), SG-11V3 (SEQ ID NO:15), SG-11V4 (SEQ ID NO:17) and SG-11V5 (SEQ ID NO:19)) to reduce incidence of detrimental PTMs.

Examples 13-16 describe experiments performed to characterize the effects of amino acid substitutions on stability and function of the SG-11 variant SG-11V5 (SEQ ID NO:19, comprising N53S, N83S, C147V, C151S with respect to SEQ ID NO:7). SG-11V5 (expressed and purified as described in Example 1).

In accordance with PTMs observed when SG-11 (SEQ ID NO:9) was subjected to stress conditions (Example 11), SG-11V5 (SEQ ID NO:19) was analyzed by LC-MS/MS for post translational modifications using the methods described in Example 11, and compared with PTMs for SG-11 (SEQ ID NO:7).

For this analysis, PTMs of wild type SG-11 (SEQ ID NO:7) and SG-11V5 (SEQ ID NO:19) were compared. In the first analysis (results provided in Table 9 below), the proteins were stored at a concentration of 1 mg/nl in Buffer 1 (50 mM NaP$_4^-$, pH 8, 150 mM NaCl, 10% glycerol) and stored for 2 weeks at either 4° C. or 40° C. The proteins were then treated with DTT and IAA, followed by trypsin digestion. The digested samples were then analyzed by Waters ACQUITY UPLC couples to XEVO®~ G2-XS QTOF mass spectrometer using a Protein BEH C18 column. Analysis of the proteins by LC-MS/MS showed that the SG11V5 protein had significantly lower percentages of oxidation of the start methionine and deamidation of N137 as compared to SG-11 at both 4° C. and 40° C.

TABLE 9

| Protein | PTM site | Mod | 4° C. | 40° C. |
|---|---|---|---|---|
| SG-11 (SEQ ID NO: 7) | MLEGEESVVYVGK (SEQ ID NO: 26) | Oxidation of M1 | 8.9% | 12.5% |
| SG-11V5 (SEQ ID NO: 19) | MLEGEESVVYVGK (SEQ ID NO: 26) | Oxidation of M1 | 2.5% | 4.7% |
| SG-11 (SEQ ID NO: 7) | TPEDYTAFNGIELYQGK (SEQ ID NO: 26) | Deamidation of N83 | 19.4% | 98.1% |
| SG-11V5 (SEQ ID NO: 19) | TPEDYTAFSGIELYQGK (SEQ ID NO: 28) | Deamidation of N83 | — | — |
| SG-11 (SEQ ID NO: 7) | ANTDVK (SEQ ID NO: 24) | Deamidation of N137 | 1.0% | 0.9% |
| SG-11V5 (SEQ ID NO: 19) | ANTDVK (SEQ ID NO: 24) | Deamidation of N137 | 0.1% | 0.3% |

In a second analysis, the SG-11 (SEQ ID NO:7) and SG-11V5 (SEQ ID NO: 19) proteins were each stored at 40° C. in a variety of buffers. The results are provided in Table 10 below. The storage buffer used in this experiment was 100 mM NaPO$_4^-$, pH7, with 10% sorbitol (+Sor) or without 10% sorbitol (−Sor) and with 10% glycerol (+Gly) or without 10% glycerol (−Gly) as indicated in Table 10. As the data in Table 10 demonstrate, there was a large decrease in oxidation of the methionine in the first position for the SG-11V5 (SEQ ID NO:19) protein as compared to the SG-11 (SEQ ID NO:7) protein in all buffer conditions. There were also differences in levels of N137 deamidation for the two proteins with the presence of at least glycerol and also the presence of both sorbitol and glycerol resulting in large decreases in N137 deamidation. These data show that substitution of amino acids in the SG-111 protein can have significant beneficial effects on PTMs of the protein in a solution.

TABLE 10

| Protein | PTM site | Modification | −Sor −Gly | +Sor −Gly | −Sor +Gly | +Sor +Gly |
|---|---|---|---|---|---|---|
| SG-11 (SEQ ID NO: 7) | MLEGEESVVYVGK (SEQ ID NO: 26) | Oxidation of M1 | 20% | 12.1% | 38.6% | 27.8% |
| SG-11V5 (SEQ ID NO: 19) | MLEGEESVVYVGK (SEQ ID NO: 26) | Oxidation of M1 | 2.7% | 3.3% | 5.6% | 5.9% |
| SG-11 (SEQ ID NO: 7) | TPEDYTAFNGIELYQGK (SEQ ID NO: 26) | Deamidation of N83 | 98.1% | 93.9% | 96.2% | 87.4% |
| SG-11V5 (SEQ ID NO: 19) | TPEDYTAFSGIELYQGK (SEQ ID NO: 28) | Deamidation of N83 | — | — | — | — |

TABLE 10-continued

| Protein | PTM site | Modification | -Sor -Gly | +Sor -Gly | -Sor +Gly | +Sor +Gly |
|---|---|---|---|---|---|---|
| SG-11 (SEQ ID NO: 7) | ANTDVK (SEQ ID NO: 24) | Deamidation of N137 | 0.9% | 2.6% | 3.0% | 2.5% |
| SG-11V5 (SEQ ID NO: 19) | ANTDVK (SEQ ID NO: 24) | Deamidation of N137 | 1.5% | 3.3% | 0.4% | 0.1% |

Example 14

SG-11 Variant Construction and Stability Analysis

Although SG-11 protein is very stable at high temperature, forming aggregations at 37° C. in a week could be the problem at the downstream processing stage. Deamidation of asparagine residues found by LC/MS/MS are also a risk factor. In order to improve the manufacturability of a protein comprising SEQ ID NO:3 or variants thereof, the protein depicted as SG-11 (SEQ ID NO:7) was mutated to contain the following 4 substitutions: N53S, N83S, C147V and C151S. This variant with 4 substitutions is designated as SG-11V5, provided herein as SEQ ID NO:19. The stability of purified SG-11 and SG-11V5 was tested in different storage buffer formulations. SG-11V5 (SEQ ID NO:19) has about 98.3% sequence identity to SEQ ID NO:7.

Stability Analysis of SG-11

FIG. 18 shows effects of conditions on SG-11 (SEQ ID NO:7) stability. Specifically, purified SG-11 (SEQ ID NO:7) was incubated in pH 5.2 (FIGS. 18A, 18B and 18C), pH 7.0 (FIGS. 18D, 18E and 18F) and pH 8.0 (FIGS. 18G, 18H and 18I). Effect of additives was also tested at the 3 different pH conditions: 150 mM NaCl (FIGS. 18A, 18D and 18G); 150 mM NaCl and 100 mM arginine (FIGS. 18B, 18E and 18H); and 150 mM NaCl and 0.5 M sorbitol (FIGS. 18C, 18F and 18I). Stability was analyzed by analytical SEC. Arrow heads indicate the retention time of the monomeric form.

Stability Analysis of SG-11V5

FIG. 19 shows effects of conditions on SG-11V5 (SEQ ID NO:19) stability. SG-11V5 (SEQ ID NO:19) was incubated in pH 5.2 (FIGS. 19A, 19B and 19C), pH 7.0 (FIGS. 19D, 19E and 19F) and pH 8.0 (FIGS. 19G, 19H and 19I). Effect of additives was also tested at the 3 different pH conditions: 150 mM NaCl (FIGS. 19A, 19D and 19G); 150 mM NaCl and 100 mM Arg (FIGS. 19B, 19E and 19H); and 150 mM NaCl and 0.5 M sorbitol (FIGS. 19C, 19F and 19I). Stability was analyzed by analytical SEC. Arrow heads indicate the retention time of the monomeric form.

In the presence of 100 mM arginine at pH 7.0, aggregate formation of the purified SG-11 (SEQ ID NO:7) protein was greatly suppressed. However, some small peaks were observed at earlier retention time, which indicated there were different forms other than the monomeric form. SG-11V5 (SEQ ID NO:19) did not show large amount of aggregation under all conditions tested in this example. Even without any additives, the discrete monomeric peak was observed. The small aggregation peak at 1.34 mL were suppressed by 100 mM arginine or 0.5 M sorbitol. The purified SG-11 (SEQ ID NO:7) and SG-11V5 (SEQ ID NO:19) were precipitated at pH 5.2.

Elevated temperature can increase protein susceptibility to degradation and aggregation due to deamidation. To minimize potential liabilities associated with deamidation and aggregation, the mutations N53S, N83S C147V and C151S were introduced into in SG-11. Thus, SG-11V5 showed improved stability at the pH 7.0 and pH 8.0.

Example 15

In Vitro Functional Analysis of SG-11V5

An in vitro TEER assay was performed to demonstrate that SG-11 variants, e.g., SG-11V5, maintain functionality related to maintenance of epithelial barrier function as shown for SG-11 proteins (see, e.g., Example 2).

Figure 20:
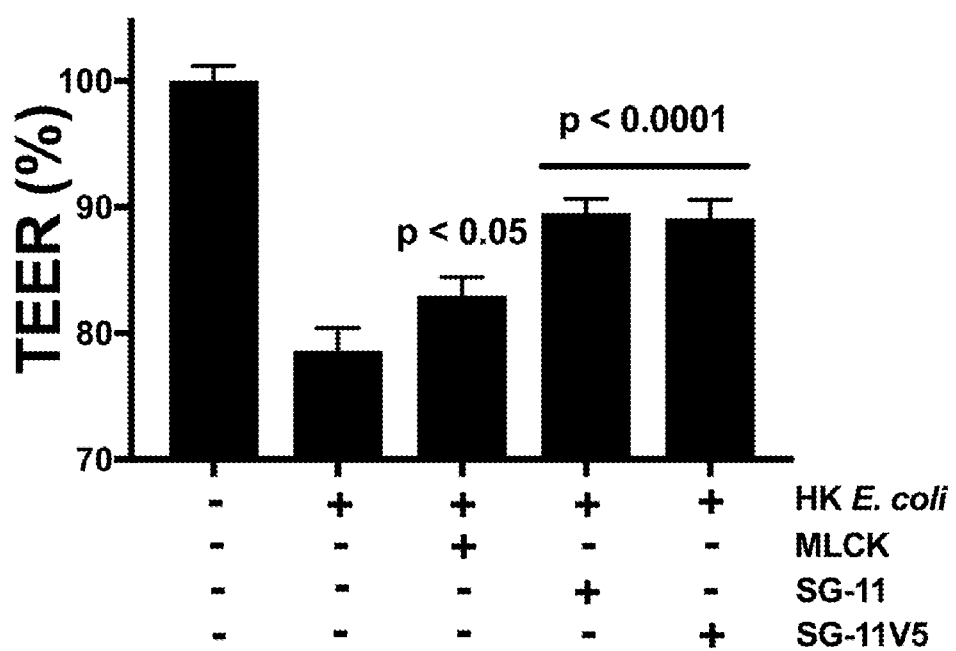
FIG. 20 shows restoration, by SG-11 and an SG-11 variant, of epithelial barrier integrity following inflammation induced disruption upon, as described in Example 15.

Cell culture was performed as described in Example 2. Briefly, following 8-10 days of culture the transwell plate containing enterocytes were treated with 10 ng/ml IFN-γ added to the basolateral chamber of the transwell plate for 24 hours at 37° C.+5% $CO_2$. After 24 hours fresh cRPMI was added to the epithelial cell culture plate. Trans-epithelial electrical resistance (TEER) readings were measured after the IFN-γ treatment and were used as the pre-treatment TEER values. SG-11 (SEQ ID NO:9) or SG-11V5 (SEQ ID NO:19) was then added to the apical chamber of the transwell plate at a final concentration of 1 μg/ml (40 nM). The myosin light chain kinase (MLCK) inhibitor peptide 18 (BioTechne, Minneapolis, Minn.) was used at 50 nM as a positive control to prevent inflammation induced barrier disruption (Zolotarevskky et al., 202, Gastroenterology, 123: 163-172). Compounds were incubated on enterocytes for 6 hours. Following pre-incubation with test compounds the transwell insert containing the enterocytes was transferred on top of the receiver plate containing U937 monocytes. Heat killed E. coli (HK E. coli) (bacteria heated to 80° C. for 40 minutes) was then added to both the apical and basolateral chambers and a multiplicity of infection (MOI) of 10. Transwell plates were incubated at 37° C.+5% $CO_2$ for 24 hours and a post treatment TEER measurement was made. SG-11 (SEQ ID NO:9) increased TEER from 78.6% disruption by HK E. coli to 89.5% (p<0.0001), while SG-11V5 (SEQ ID NO:19) increased to 89.1% (p<0.0001) (FIG. 20). Statistical analysis was performed using a one-way ANOVA compared to HK E. coli followed by a Fisher's LSD multiple comparison test. The graphs in FIG. 20 represent data pooled from four plates performed in two individual experiments (n=12).

Example 16

In Vivo Functional Analysis of SG-11V5

Next, the DSS animal model experiments performed as described above in Examples 7 and 8 were repeated to test SG-11 or SG-11V5 (SEQ ID NO:19) in parallel. In these experiments, SG-11 or SG-11V5 was administered to a mouse concurrent with the initiation of treatment with DSS (as in Example 7) or after prior DSS administration. The only difference is that mice in Example 8 were treated with SG-11 or SG-11V5 (SEQ ID NO:19) for 4 days rather than 6 days.

In the first DSS mouse model (Example 16A; same method as Example 7), mice were treated on day zero with test compound intraperitoneally (i.p.) and 6 hours later DSS treatment was initiated. Doses administered included 50 nmoles/kg for SG-11 (SEQ ID NO:9) (1.3 mg/ml), and Gly2-GLP2 (0.2 mg/kg), and a dose response for SG-11V5 (SEQ ID NO:19) including 16 nmoles/kg (0.4 mg/ml), 50 nmoles/kg (1.3 mg/ml) and 158 nmoles/kg (4.0 mg/kg). The mice were treated with 2.5% DSS in their drinking water for 6 days (day zero through day 6). Therapeutic protein treatments were administered twice a day for the duration of the DSS exposure.

In the second experiment (Example 16B; same method as Example 8), mice were provided with drinking water containing 2.5% DSS for 7 days. On day 7 normal drinking water was restored and i.p. treatments of 50 nmole/kg of SG-11 (SEQ ID NO:9) (1.3 mg/kg), SG-11V5 (SEQ ID NO:19) (1.3 mg/kg), or Gly2-GLP2 (0.2 mg/kg) were initiated. Treatments were administered twice a day (b.i.d.), with a morning and evening dose (every 8 and 16 hours) for 4 days. For both DSS models (Example 16A and 16B) fresh 2.5% DSS water was prepared every 2 days during the DSS administration.

Figure 21A:
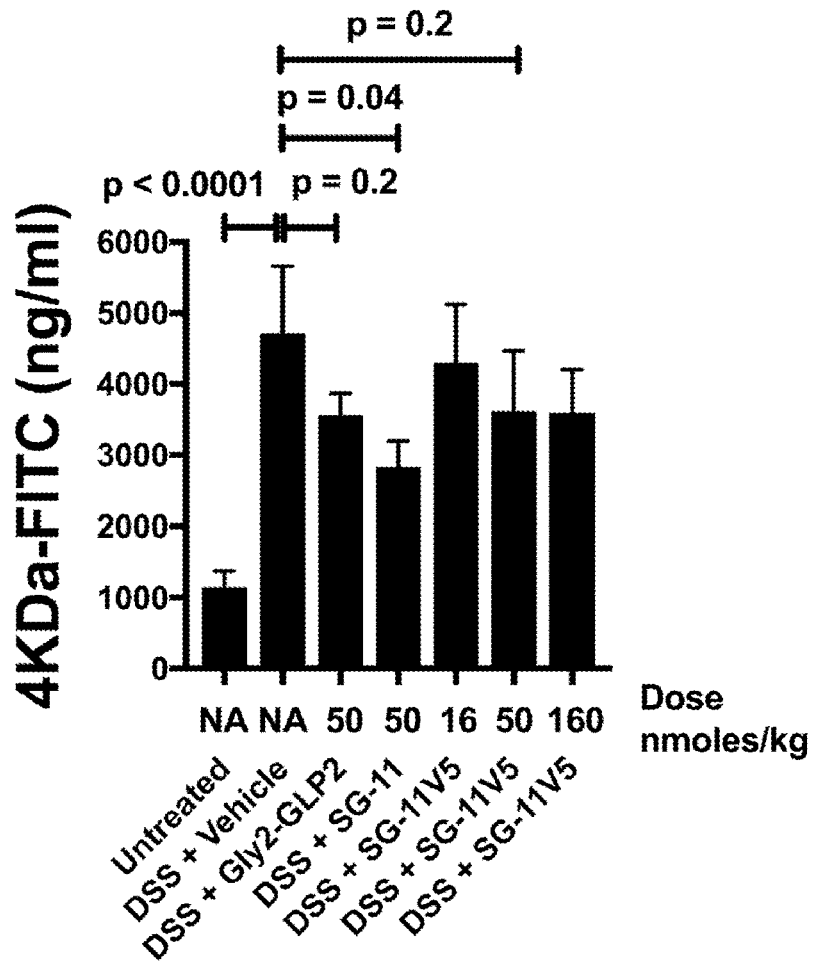
FIG. 21A and FIG. 21B show epithelial barrier integrity following treatment of a DSS model of inflammatory bowel disease with SG-11 and a variant of SG-11, as described in Example 16.
Figure 21B:
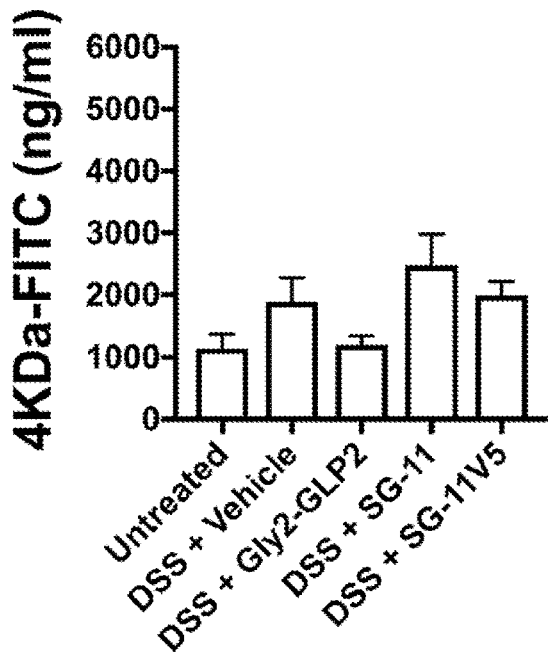

At the end of each DSS experiment, mice were fasted for 4 hours and then orally gavaged with 600 mg/kg 4KDa dextran labeled with fluorescein isothiocyanate (FITC) [4KDa-FITC]. One hour after the 4KDa-FITC gavage mice were euthanized, blood was collected and FITC signal was measured in serum. For the first model a significant increase in 4KDa-FITC dextran translocation across the epithelial barrier was observed in vehicle treated DSS mice as compared to untreated mice. The results are illustrated in FIG. 21A: SG-11 (SEQ ID NO:9) significantly reduced the 4KDa-FITC signal ($p=0.04$). SG-11V5 (SEQ ID NO:19) also reduced the 4KDa-FITC signal, although the difference did not reach statistical significance ($p=0.21$). In FIG. 21B, similar to previous results in example 8, no increase in 4KDa-FITC was observed and so no effect of SG-11 or SG-11V5 treatment was observed. Data in both graphs are plotted as mean±SEM and each figure represent data from an individual experiment (n=10 per group).

Figure 22A:
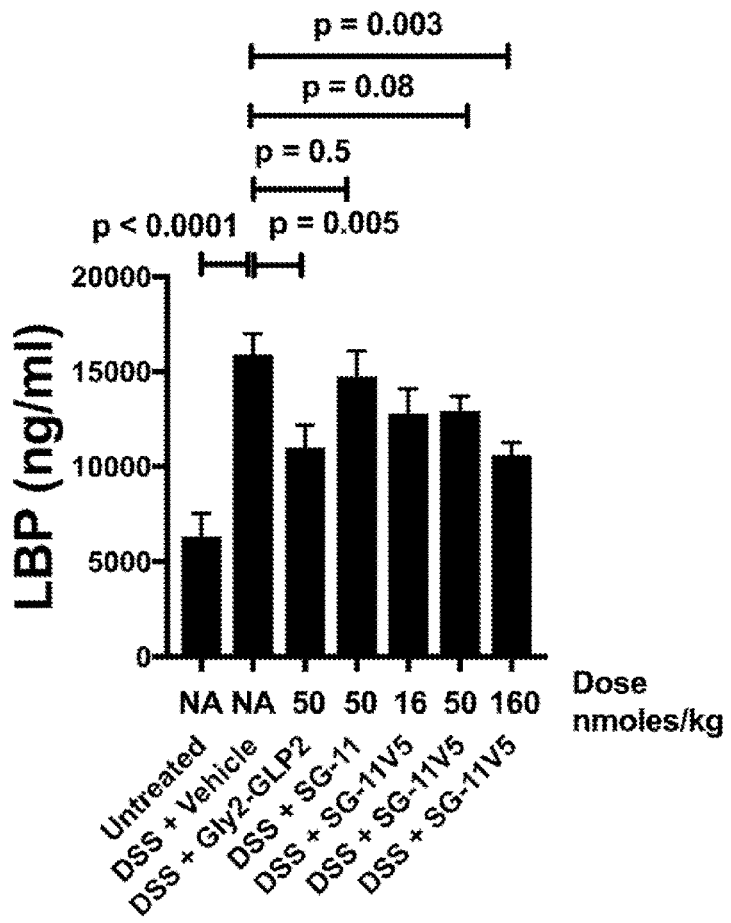
FIG. 22A and FIG. 22B show inflammation centric readouts of barrier function in a DSS model of inflammatory bowel disease, as described in Example 16.
Figure 22B:
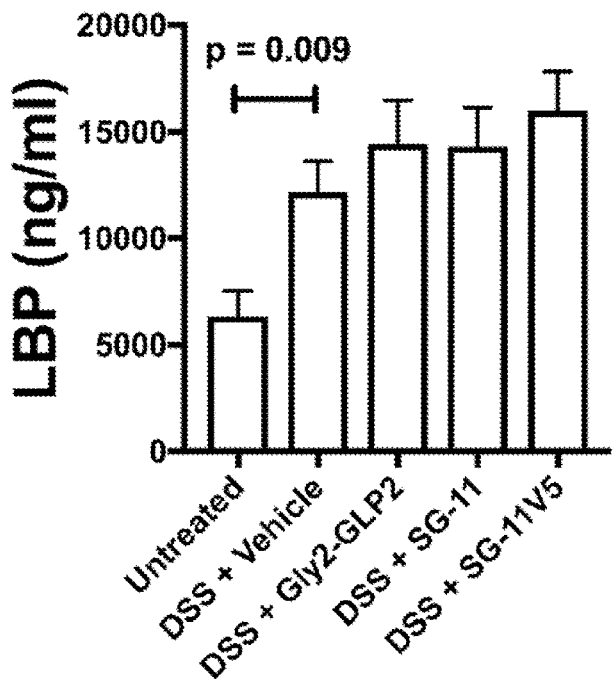

Effects of SG-11V5 on Inflammation Centric Readouts of Barrier Function in a DSS Model of Inflammatory Bowel Disease Upon completion of the DSS models above, LBP levels were measured as an inflammation centric readout of barrier function following the protocol detailed in Example 7. Upon completion of both DSS models (Examples 16A and 16B) blood was collected and serum was isolated. LPS binding protein (LBP) levels were measured in serum using a commercially available ELISA Kit (Enzo Life Sciences, Farmingdale, N.Y.). Results are provided in FIG. 22A (Example 16A) and FIG. 22B (Example 16B). A significant increase in LBP was observed in the Example 16A DSS model in response to DSS exposure. At the 50 nmoles/kg dose SG-11 (SEQ ID NO:9) and SG-11V5 (SEQ ID NO:19) similar reductions in LBP were observed although neither were statistically significant. However, SG-11V5 (SEQ ID NO:19) treatment at a higher dose of 158 nmoles/kg resulted in a significant reduction in LBP production ($p=0.003$) (FIG. 22A). In the Example 16B DSS model, exposure to DSS resulted in a significant increase in LBP production (FIG. 22B). However, no reduction in LBP was observed for any of the treatments and similar effects were observed for both SG-11 (SEQ ID NO:9) and SG-11V5 (SEQ ID NO:19). Without being bound by theory, it is thought that the long half-life of LBP in circulation (reported to be 12-24 hours) may make it difficult to observe reductions in systemic LBP levels in the model where the LBP response is elicited (DSS is administered) prior to initiation of treatment (Behrendt, D., J. Dembinski, A. Heep, and P. Bartmann. 2004. Lipopolysaccharide binding protein in preterm infants. *Arch Dis Child Fetal Neonatal Ed* 89: F551-554).

Effects of SG-11 and SG-11V5 on body weight in a DSS model of inflammatory bowel disease Body weight was measured throughout the experimental models in both Example 16A and Example 16B. In the Example 16A DSS model (FIG. 23A) similar trends in body weight were observed for SG-11 (SEQ ID NO:9) and SG-11V5 (SEQ ID NO:19) treatments at 50 nmoles/kg, and a significant improvement in body weight was observed at day 6 for SG-11V5 (SEQ ID NO:19) at 158 nmoles/kg. Similar patterns were observed in the therapeutic DSS model where SG-11 (SEQ ID NO:9) and SG-11V5 (SEQ ID NO:19) at the 50 nmoles/kg dose had similar changes in body weight with both having statistically improved body weight changes at day 11 ($p<0.05$). For FIG. 23A and FIG. 23B, data are graphed as mean±SEM and each graph represent data from an individual experiment. Statistical analysis was performed using a two-way ANOVA as compared to the DSS+vehicle group with a Fisher's LSD multiple comparison test.

Effects of SG-11 and SG-11V5 on Gross Pathology in a DSS Model of Inflammatory Bowel Disease Gross pathology observations of colon tissue were made for Example 16A as described in Example 7 above. Briefly, a scoring system based on the level of visible blood and fecal pellet consistency was used. The scoring system used was: (0)=no gross pathology, (1)=streaks of blood visible in feces, (2)=completely bloody fecal pellets, (3) bloody fecal material visible in cecum, (4) bloody fecal material in cecum and loose stool, (5)=rectal bleeding. Similar results were obtained for SG-11 (SEQ ID NO:9) and SG-11V5 (SEQ ID NO:19) at the dose of 50 nmoles/kg and a dose dependent effect was observed for SG-11V5 (SEQ ID NO:19) with the 160 nmoles/kg dose resulting in a significant improvement ($p<0.002$). Data, illustrated in FIG. 24, are presented as mean±SEM and include data from an individual experiment. Statistical analysis was performed using a one-way ANOVA followed by a Fisher's LSD multiple comparison test.

Figure 25A:
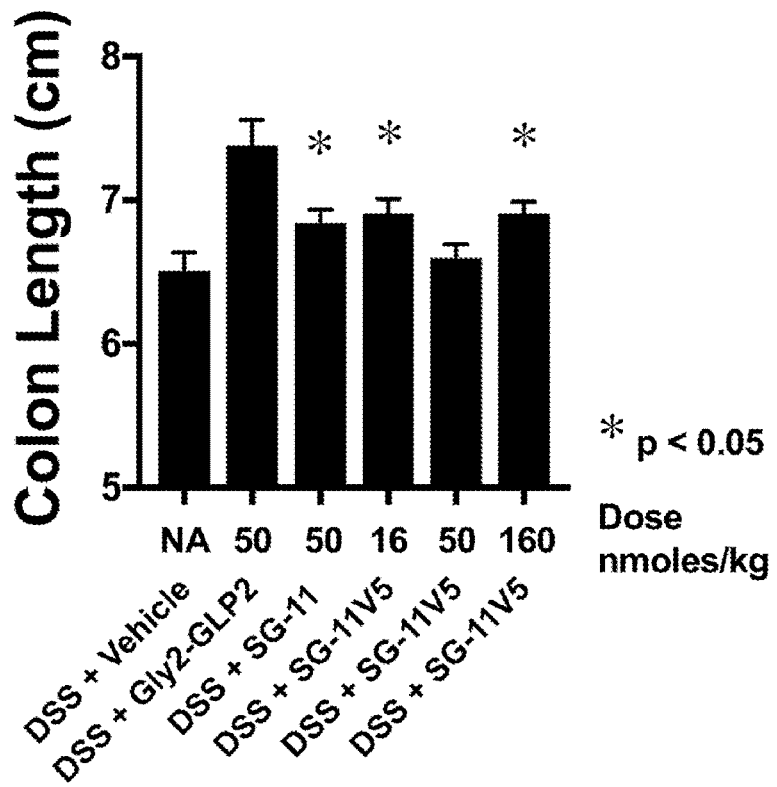
FIG. 25A and FIG. 25B show effects of treatment with SG-11 or a variant of SG-11 on colon length in a DSS model of inflammatory bowel disease, as described in Example 16.
Figure 25B:
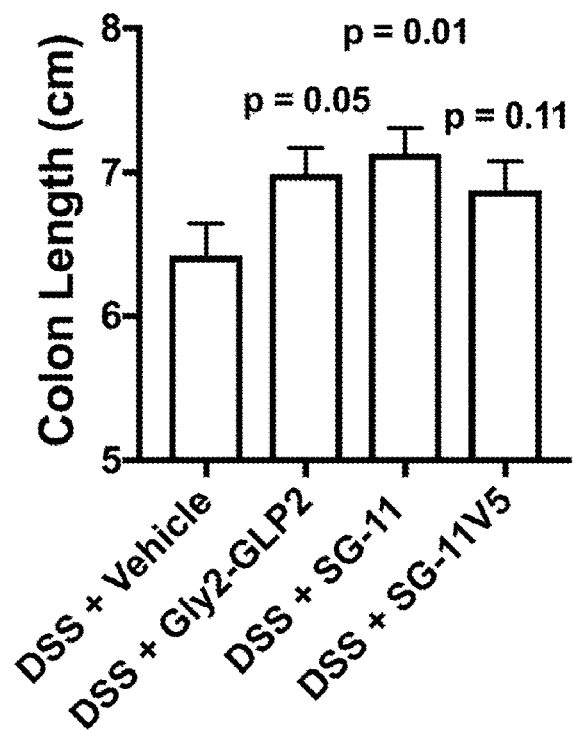

Effects of SG-11 and SG-11V5 on Colon Length in a DSS Model of Inflammatory Bowel Disease DSS models from Example 16 were also analyzed for the effect of SG-11 and SG-11 variant proteins on the colon length. Colon length measurements were made for the Example 16A (FIG. 25A) or Example 16B (FIG. 25B) DSS models. Similar results were obtained with SG-11 (SEQ ID NO:9) and SG-11V5 (SEQ ID NO:19) in both DSS models where both treatment regimens resulted in a significant increase in the colon length. However, no dose-dependent effect on colon length was observed with SG-11V5 (SEQ ID NO:19) in the DSS model of Example 16A. Data in both graphs are presented as mean±SEM and represent data from an individual experiment. Statistical analysis was performed using a one-way ANOVA compared to DSS+vehicle followed by a Fishers LSD multiple comparison test.

Figure 26A:
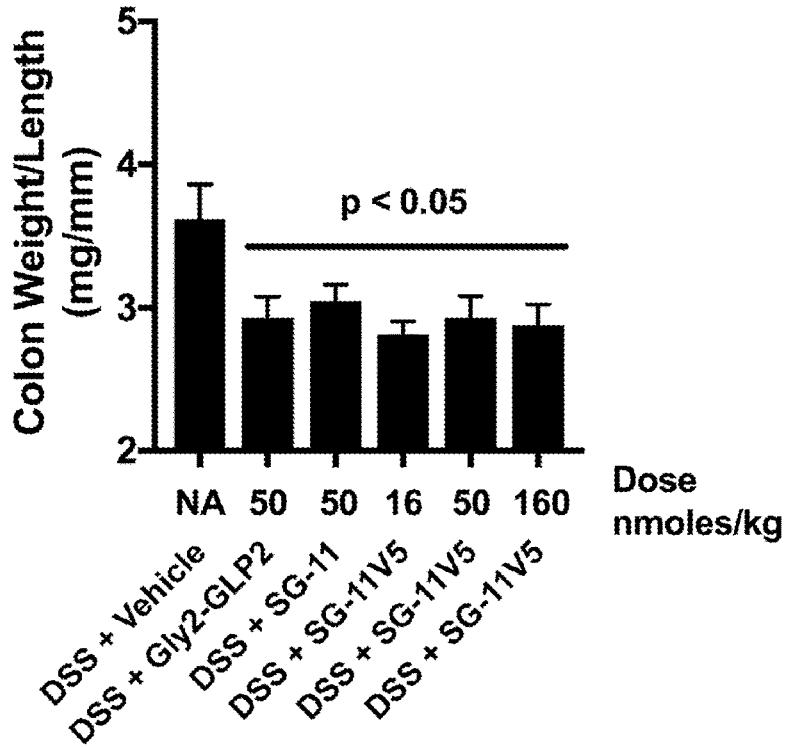
FIG. 26A and FIG. 26B show effects of treatment with SG-11 or a variant of SG-11 on colon weight-to-length ratio in a DSS model of inflammatory bowel disease, as described in Example 16.
Figure 26B:
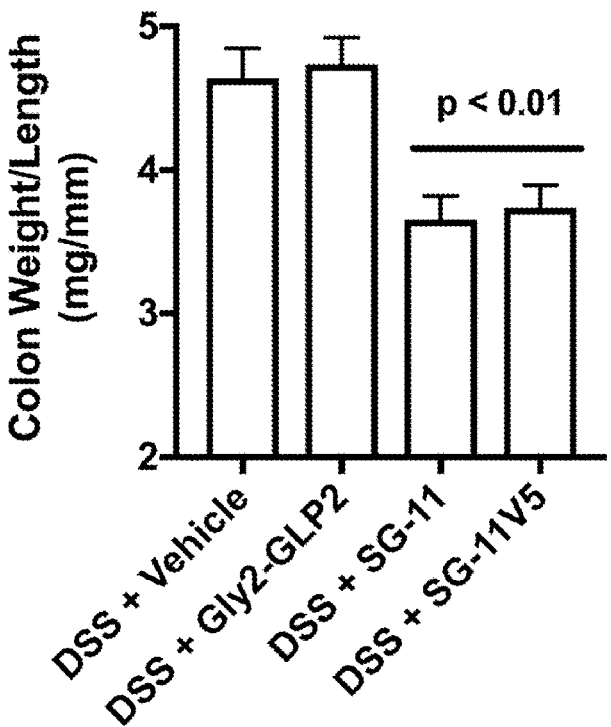

Effects of SG-11 and SG-11V5 on Colon Weight-to-Length Ratios in a DSS Model of Inflammatory Bowel Disease DSS models from Example 16 were also analyzed for the effect of SG-11 and SG-11 variant proteins on the colon weight-to-length ratio. Colon weight to length ratios were similar between SG-11 (SEQ ID NO:9) and SG-11V5 (SEQ ID NO:19) in the Example 16A (FIG. 26A) and Example 16B (FIG. 26B) DSS model treatment regimens. In the Example 16A treatment, all treatments and doses significantly improved colon weight to length ratios (p<0.05). In the Example 16B treatment regiment, SG-11 (SEQ ID NO:9) and SG-11V5 (SEQ ID NO:19) both significantly improved colon weight to length ratios (p<0.01), while the positive control Gly2-GLP2 did not. Statistical analysis was performed by a one-way ANOVA as compared to DSS+ vehicle using a Fisher's LSD multiple comparisons test. Data are graphed as mean±SEM and each figure represent data from a single experiment.

Although the foregoing disclosure has been described in some detail by way of illustration and examples, which are for purposes of clarity of understanding, it will be apparent to those skilled in the art that certain changes and modifications may be practiced without departing from the spirit and scope of the disclosure, which is delineated in the appended claims. Therefore, the description should not be construed as limiting the scope of the disclosure.

Table 11 demonstrates SEQ ID NOs of the present disclosure with detailed information.

TABLE 11

| SEQ ID NO | Type | Description | Name |
|---|---|---|---|
| 1 | PRT | Full-length protein with signal sequence | SG-11 |
| 2 | DNA | coding sequence (cds) for SEQ ID NO: 1 | |
| 3 | PRT | SEQ ID NO: 1 without signal sequence and without "start methionine" | SG-11 |
| 4 | DNA | cds for SEQ ID NO: 3 | |
| 5 | PRT | SEQ ID NO: 3 expressed in pGEX6 vector and cleaved by Precision protease | SG-11 |
| 6 | DNA | cds for SEQ ID NO: 5 | |
| 7 | PRT | SEQ ID NO: 3 with "start methionine" | SG-11 |
| 8 | DNA | cds for SEQ ID NO: 7 (codon optimized) | |
| 9 | PRT | SEQ ID NO: 3 with N-terminal FLAG tag | SG-11 |
| 10 | DNA | cds for SEQ ID NO: 9 (not codon optimized) | |
| 11 | PRT | Artificial variant of SEQ ID NO: 7 (C147V, C151S) | SG-11V1 |
| 12 | DNA | cds for SEQ ID NO: 11 (codon optimized) | |
| 13 | PRT | Artificial variant of SEQ ID NO: 7 (G84D, C147V, C151S) | SG-11V2 |
| 14 | DNA | cds for SEQ ID NO: 13 (codon optimized) | |
| 15 | PRT | Artificial variant of SEQ ID NO: 7 (N83S, C147V, C151S) | SG-11V3 |
| 16 | DNA | cds for SEQ ID NO: 15 (codon optimized) | |
| 17 | PRT | Artificial variant of SEQ ID NO: 7 (N53S, G84D, C147V, C151S) | SG-11V4 |
| 18 | DNA | cds for SEQ ID NO: 17 (codon optimized) | |
| 19 | PRT | Artificial variant of SEQ ID NO: 7 (N53S, N83S, C147V, C151S) | SG-11V5 |
| 20 | DNA | cds for SEQ ID NO: 19 (codon optimized) | |
| 21 | PRT | *R. intestinalis* hypothetical protein (GenBank WP_006857001.1) | |
| 22 | PRT | *Roseburia* sp. 831b hypothetical protein (GenBank WP_075679733.1) | |
| 23 | PRT | *R. inulinivorans* hypothetical protein (GenBank WP_055301040.1) | |
| 24 | PRT | Fragment of SEQ ID NO: 7 from Tables 6 and 8 | |
| 25 | PRT | Fragment of SG-11 from Table 6 | |
| 26 | PRT | Fragment of SG-11 from Table 6 | |
| 27 | PRT | Fragment of SG-11 from Table 6 | |
| 28 | PRT | Fragment of SG-11 Table 6 | |
| 29 | PRT | Fragment of SG-11 from Table 8 | |
| 30 | PRT | Fragment of SG-11 from Tables 6 and 8 | |
| 31 | PRT | Fragment of SG-11 from Table 8 | |
| 32 | PRT | FLAG tag | FLAG |
| 33 | PRT | Variant protein with X at positions 53, 83, 84, 147 and 151 | |
| 34 | PRT | Variant protein with X at positions 53, 83, 84, 147 and 151 | |

Numbered Embodiments of the Disclosure

Notwithstanding the appended claims, the disclosure sets forth the following numbered embodiments:

Methods of Treatment

1. A method of treating a gastrointestinal epithelial cell barrier function disorder, comprising:
   a. administering to a patient in need thereof a pharmaceutical composition, comprising:
      i. a therapeutic protein comprising an amino acid sequence having at least about 85% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19; and
      ii. a pharmaceutically acceptable carrier.

2. The method of claim 1, wherein the gastrointestinal epithelial cell barrier function disorder is a disease associated with decreased gastrointestinal wall integrity.

3. The method of any one of claims 1-2, wherein the gastrointestinal epithelial cell barrier function disorder is a disease associated with decreased gastrointestinal mucosal epithelium integrity.

4. The method of any one of claims 1-3, wherein the gastrointestinal epithelial cell barrier function disorder is a disease associated with decreased intestinal epithelium integrity.

5. The method of any one of claims 1-4, wherein the gastrointestinal epithelial cell barrier function disorder is at least one selected from the group consisting of: inflammatory bowel disease, Crohn's disease, ulcerative colitis, pouchitis, irritable bowel syndrome, enteric infections, *Clostridium difficile* infections, metabolic diseases, obesity, type 2 diabetes, non-alcoholic steatohepatitis, non-alcoholic fatty liver disease, liver disorders, alcoholic steatohepatitis, celiac disease, necrotizing enterocolitis, gastro intestinal disorders, short bowel syndrome, GI mucositis, chemotherapy induced mucositis, radiation induced mucositis, oral mucositis, interstitial cystitis, neurological disorders, cognitive disorders, Alzheimer's, Parkinson's, multiple sclerosis, autism, chemotherapy associated steatohepatitis (CASH), and pediatric versions of the aforementioned diseases.

6. The method of any one of claims 1-5, wherein the gastrointestinal epithelial cell barrier function disorder is inflammatory bowel disease.

7. The method of any one of claims 1-6, wherein the gastrointestinal epithelial cell barrier function disorder is Crohn's disease.

8. The method of any one of claims 1-6, wherein the gastrointestinal epithelial cell barrier function disorder is ulcerative colitis.

9. The method of any one of claims 1-8, wherein the therapeutic protein comprises an amino acid sequence having at least about 90% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

10. The method of any one of claims 1-9, wherein the therapeutic protein comprises an amino acid sequence having at least about 95% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

11. The method of any one of claims 1-10, wherein the therapeutic protein comprises an amino acid sequence having at least about 97% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

12. The method of any one of claims 1-11, wherein the therapeutic protein comprises an amino acid sequence having at least about 98% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

13. The method of any one of claims 1-12, wherein the therapeutic protein comprises an amino acid sequence having at least about 99% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

14. The method of any one of claims 1-13, wherein the therapeutic protein comprises an amino acid sequence selected from the group consisting of: SEQ ID NO: 3, SEQ ID NO: 7, SEQ ID NO: 11, SEQ ID NO: 13, SEQ ID NO: 15, SEQ ID NO: 17, and SEQ ID NO: 19.

15. The method of any one of claims 1-14, wherein the therapeutic protein comprises the amino acid sequence of SEQ ID NO: 3.

16. The method of any one of claims 1-14, wherein the therapeutic protein comprises the amino acid sequence of SEQ ID NO: 7.

17. The method of any one of claims 1-14, wherein the therapeutic protein comprises the amino acid sequence of SEQ ID NO: 11.

18. The method of any one of claims 1-14, wherein the therapeutic protein comprises the amino acid sequence of SEQ ID NO: 13.

19. The method of any one of claims 1-14, wherein the therapeutic protein comprises the amino acid sequence of SEQ ID NO: 15.

20. The method of any one of claims 1-14, wherein the therapeutic protein comprises the amino acid sequence of SEQ ID NO: 17.

21. The method of any one of claims 1-14, wherein the therapeutic protein comprises the amino acid sequence of SEQ ID NO: 19.

22. The method of any one of claims 1-21, wherein administering comprises rectal, parenteral, intravenous, topical, oral, dermal, transdermal, or subcutaneous administration.

23. The method of any one of claims 1-22, wherein administering is to the: mouth, gastrointestinal lumen, and/or intestines of the patient.

24. The method of any one of claims 1-23, wherein the patient experiences a reduction in at least one symptom associated with the gastrointestinal epithelial cell barrier function disorder.

25. The method of any one of claims 1-24, wherein the patient experiences a reduction in at least one symptom associated with the gastrointestinal epithelial cell barrier function disorder selected from the group consisting of: abdominal pain, blood in stool, pus in stool, fever, weight loss, frequent diarrhea, fatigue, reduced appetite, tenesmus, and rectal bleeding.

26. The method of any one of claims 1-25, wherein administering reduces gastrointestinal inflammation in the patient.

27. The method of any one of claims 1-25, wherein administering reduces intestinal mucosal inflammation in the patient.

28. The method of any one of claims 1-25, wherein administering increases the production of mucin in intestinal tissue in the patient.

29. The method of any one of claims 1-25, wherein administering increases intestinal epithelium wound healing in the patient 30. The method of any one of claims 1-25, wherein administering increases intestinal epithelial cell proliferation in the patient.

31. The method of any one of claims 1-30, further comprising: administering at least one second therapeutic agent to the patient.

32. The method of any one of claims 1-31, further comprising: administering at least one second therapeutic agent to the patient, said second therapeutic agent selected from the group consisting of: an anti-diarrheal, a 5-aminosalicylic acid compound, an anti-inflammatory agent, an antibiotic, an antibody, an anti-cytokine agent, an anti-inflammatory cytokine agent, a steroid, a corticosteroid, and an immunosuppressant.

Pharmaceutical Compositions

1. A pharmaceutical composition, comprising:
    a. a therapeutic protein comprising an amino acid sequence having at least about 85% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19; and
    b. a pharmaceutically acceptable carrier.

2. The pharmaceutical composition of claim 1, wherein the therapeutic protein comprises an amino acid sequence having at least about 90% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

3. The pharmaceutical composition of any one of claims 1-2, wherein the therapeutic protein comprises an amino acid sequence having at least about 95% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

4. The pharmaceutical composition of any one of claims 1-3, wherein the therapeutic protein comprises an amino acid sequence having at least about 97% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

5. The pharmaceutical composition of any one of claims 1-4, wherein the therapeutic protein comprises an amino acid sequence having at least about 98% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

6. The pharmaceutical composition of any one of claims 1-5, wherein the therapeutic protein comprises an amino acid sequence having at least about 99% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19.

7. The pharmaceutical composition of any one of claims 1-6, wherein the therapeutic protein comprises an amino acid sequence selected from the group consisting of: SEQ ID NO: 3, SEQ ID NO: 7, SEQ ID NO: 11, SEQ ID NO: 13, SEQ ID NO: 15, SEQ ID NO: 17, and SEQ ID NO: 19.

8. The pharmaceutical composition of any one of claims 1-7, wherein the therapeutic protein comprises the amino acid sequence of SEQ ID NO: 3.

9. The pharmaceutical composition of any one of claims 1-7, wherein the therapeutic protein comprises the amino acid sequence of SEQ ID NO: 7.
10. The pharmaceutical composition of any one of claims 1-7, wherein the therapeutic protein comprises the amino acid sequence of SEQ ID NO: 11.
11. The pharmaceutical composition of any one of claims 1-7, wherein the therapeutic protein comprises the amino acid sequence of SEQ ID NO: 13.
12. The pharmaceutical composition of any one of claims 1-7, wherein the therapeutic protein comprises the amino acid sequence of SEQ ID NO: 15.
13. The pharmaceutical composition of any one of claims 1-7, wherein the therapeutic protein comprises the amino acid sequence of SEQ ID NO: 17.
14. The pharmaceutical composition of any one of claims 1-7, wherein the therapeutic protein comprises the amino acid sequence of SEQ ID NO: 19.
15. The pharmaceutical composition of any one of claims 1-14, formulated for rectal, parenteral, intravenous, topical, oral, dermal, transdermal, or subcutaneous administration.
16. The pharmaceutical composition of any one of claims 1-15, formulated such that the therapeutic protein has activity in the gastrointestinal lumen and/or intestines of the patient.

Expression Vectors
1. An expression vector, comprising: a polynucleotide, which encodes a protein comprising an amino acid sequence having at least about 85% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
2. The expression vector of claim 1, wherein the encoded protein comprises an amino acid sequence having at least about 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
3. The expression vector of any one of claims 1-2, wherein the encoded protein comprises an amino acid sequence having at least about 95% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
4. The expression vector of any one of claims 1-3, wherein the encoded protein comprises an amino acid sequence having at least about 97% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
5. The expression vector of any one of claims 1-4, wherein the encoded protein comprises an amino acid sequence having at least about 98% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
6. The expression vector of any one of claims 1-5, wherein the encoded protein comprises an amino acid sequence having at least about 99% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
7. The expression vector of any one of claims 1-6, wherein the encoded protein comprises an amino acid sequence selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.
8. The expression vector of any one of claims 1-7, wherein the encoded protein comprises the amino acid sequence of SEQ ID NO: 3.
9. The expression vector of any one of claims 1-7, wherein the encoded protein comprises the amino acid sequence of SEQ ID NO: 5.
10. The expression vector of any one of claims 1-7, wherein the encoded protein comprises the amino acid sequence of SEQ ID NO: 7.
11. The expression vector of any one of claims 1-7, wherein the encoded protein comprises the amino acid sequence of SEQ ID NO: 9.
12. The expression vector of any one of claims 1-7, wherein the encoded protein comprises the amino acid sequence of SEQ ID NO: 11.
13. The expression vector of any one of claims 1-7, wherein the encoded protein comprises the amino acid sequence of SEQ ID NO: 13.
14. The expression vector of any one of claims 1-7, wherein the encoded protein comprises the amino acid sequence of SEQ ID NO: 15.
15. The expression vector of any one of claims 1-7, wherein the encoded protein comprises the amino acid sequence of SEQ ID NO: 17.
16. The expression vector of any one of claims 1-7, wherein the encoded protein comprises the amino acid sequence of SEQ ID NO: 19.

Host Cells
1. A host cell, comprising: an exogenous polynucleotide, which encodes a protein comprising an amino acid sequence having at least about 85% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
2. The host cell of claim 1, wherein the encoded protein comprises an amino acid sequence having at least about 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
3. The host cell of any one of claims 1-2, wherein the encoded protein comprises an amino acid sequence having at least about 95% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
4. The host cell of any one of claims 1-3, wherein the encoded protein comprises an amino acid sequence having at least about 97% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
5. The host cell of any one of claims 1-4, wherein the encoded protein comprises an amino acid sequence having at least about 98% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
6. The host cell of any one of claims 1-5, wherein the encoded protein comprises an amino acid sequence having at least about 99% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.

7. The host cell of any one of claims 1-6, wherein the encoded protein comprises an amino acid sequence selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.
8. The host cell of any one of claims 1-7, wherein the encoded protein comprises the amino acid sequence of SEQ ID NO: 3.
9. The host cell of any one of claims 1-7, wherein the encoded protein comprises the amino acid sequence of SEQ ID NO: 5.
10. The host cell of any one of claims 1-7, wherein the encoded protein comprises the amino acid sequence of SEQ ID NO: 7.
11. The host cell of any one of claims 1-7, wherein the encoded protein comprises the amino acid sequence of SEQ ID NO: 9.
12. The host cell of any one of claims 1-7, wherein the encoded protein comprises the amino acid sequence of SEQ ID NO: 11.
13. The host cell of any one of claims 1-7, wherein the encoded protein comprises the amino acid sequence of SEQ ID NO: 13.
14. The host cell of any one of claims 1-7, wherein the encoded protein comprises the amino acid sequence of SEQ ID NO: 15.
15. The host cell of any one of claims 1-7, wherein the encoded protein comprises the amino acid sequence of SEQ ID NO: 17.
16. The host cell of any one of claims 1-7, wherein the encoded protein comprises the amino acid sequence of SEQ ID NO: 19.
17. The host cell of any one of claims 1-16, wherein the exogenous polynucleotide further encodes a host cell specific signal sequence.
18. The host cell of any one of claims 1-17, wherein the exogenous polynucleotide comprises a nucleic acid sequence having at least about 85%, 86%, 87%, 88%, 89%, 90%, 91%, 92%, 93%, 94%, 95%, 96%, 97%, 98%, 99%, or 100% sequence identity to a nucleic acid sequence selected from the group consisting of: SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20.
19. The host cell of any one of claims 1-18, wherein the host cell is a prokaryotic cell.
20. The host cell of any one of claims 1-19, wherein the host cell is an *Escherichia coli* cell.
21. The host cell of any one of claims 1-18, wherein the host cell is a eukaryotic cell.
22. The host cell of any one of claims 1-18 and 21, wherein the host cell is a Chinese Hamster Ovary cell.
23. A method of producing a protein, comprising: culturing the host cell of any one of claims 1-22, under conditions sufficient for expression of the encoded protein.

Isolated Proteins
1. An isolated therapeutic protein, comprising: an amino acid sequence having at least about 85% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
2. The isolated therapeutic protein of claim 1, comprising: an amino acid sequence having at least about 90% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
3. The isolated therapeutic protein of any one of claims 1-2, comprising: an amino acid sequence having at least about 95% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
4. The isolated therapeutic protein of any one of claims 1-3, comprising: an amino acid sequence having at least about 97% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
5. The isolated therapeutic protein of any one of claims 1-4, comprising: an amino acid sequence having at least about 98% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
6. The isolated therapeutic protein of any one of claims 1-5, comprising: an amino acid sequence having at least about 99% sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and/or SEQ ID NO: 19.
7. The isolated therapeutic protein of any one of claims 1-6, comprising: an amino acid sequence selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, and SEQ ID NO: 19.
8. The isolated therapeutic protein of any one of claims 1-7, comprising: the amino acid sequence of SEQ ID NO: 3.
9. The isolated therapeutic protein of any one of claims 1-7, comprising: the amino acid sequence of SEQ ID NO: 5.
10. The isolated therapeutic protein of any one of claims 1-7, comprising: the amino acid sequence of SEQ ID NO: 7.
11. The isolated therapeutic protein of any one of claims 1-7, comprising: the amino acid sequence of SEQ ID NO: 9.
12. The isolated therapeutic protein of any one of claims 1-7, comprising: the amino acid sequence of SEQ ID NO: 11.
13. The isolated therapeutic protein of any one of claims 1-7, comprising: the amino acid sequence of SEQ ID NO: 13.
14. The isolated therapeutic protein of any one of claims 1-7, comprising: the amino acid sequence of SEQ ID NO: 15.
15. The isolated therapeutic protein of any one of claims 1-7, comprising: the amino acid sequence of SEQ ID NO: 17.
16. The isolated therapeutic protein of any one of claims 1-7, comprising: the amino acid sequence of SEQ ID NO: 19.
17. The isolated therapeutic protein of any one of claims 1-16, wherein the protein increases electrical resistance in an in vitro transepithelial electrical resistance assay.
18. The isolated therapeutic protein of any one of claims 1-17, wherein the protein increases electrical resistance in an in vitro transepithelial electrical resistance assay by at least about 5%, 10%, 20%, 30%, 40%, 50%, 60%, 70%, 80%, 90%, 95%, or 99%, as compared to the assay performed in the absence of the protein.

19. The isolated therapeutic protein of any one of claims 1-18, wherein the protein increases electrical resistance in an in vitro transepithelial electrical resistance assay, as compared to a control of a kinase inhibitor.

20. The isolated therapeutic protein of any one of claims 1-19, wherein the protein increases electrical resistance in an in vitro transepithelial electrical resistance assay, as compared to a control of staurosporine or myosin light chain kinase.

Synthetic Therapeutic Protein

1. A synthetic therapeutic protein, comprising: an amino acid sequence having at least about 90% sequence identity to SEQ ID NO: 19.
2. The protein of claim 1, comprising: an amino acid sequence having at least about 95% sequence identity to SEQ ID NO: 19.
3. The protein of any one of claims 1-2, comprising: an amino acid sequence having at least about 97% sequence identity to SEQ ID NO: 19.
4. The protein of any one of claims 1-3, comprising: an amino acid sequence having at least about 98% sequence identity to SEQ ID NO: 19.
5. The protein of any one of claims 1-4, comprising: an amino acid sequence having at least about 99% sequence identity to SEQ ID NO: 19.
6. The protein of any one of claims 1-5, comprising: the amino acid sequence of SEQ ID NO: 19.
7. The protein of any one of claims 1-6, wherein the amino acid at position 147 is valine.
8. The protein of any one of claims 1-6, wherein the amino acid at position 151 is serine.
9. The protein of any one of claims 1-6, wherein the amino acid at position 147 is valine, and the amino acid at position 151 is serine.
10. The protein of any one of claims 1-5, wherein the amino acid at position 84 is aspartic acid.
11. The protein of any one of claims 1-5, wherein the amino acid at position 84 is aspartic acid, and the amino acid at position 147 is valine, and the amino acid at position 151 is serine.
12. The protein of any one of claims 1-6, wherein the amino acid at position 83 is serine.
13. The protein of any one of claims 1-6, wherein the amino acid at position 83 is serine, and the amino acid at position 147 is valine, and the amino acid at position 151 is serine.
14. The protein of any one of claims 1-6, wherein the amino acid at position 53 is serine.
15. The protein of any one of claims 1-5, wherein the amino acid at position 53 is serine, and the amino acid at position 84 is aspartic acid, and the amino acid at position 147 is valine, and the amino acid at position 151 is serine.
16. The protein of any one of claims 1-6, wherein the amino acid at position 53 is serine, and the amino acid at position 83 is serine, and the amino acid at position 147 is valine, and the amino acid at position 151 is serine.
17. The protein of any one of claims 1-6, wherein the amino acid at position 147 is not cysteine, the amino acid at position 151 is not cysteine, the amino acid at position 83 is not asparagine, and/or the amino acid at position 53 is not asparagine.
18. The protein of any one of claims 1-17, wherein the protein increases electrical resistance in an in vitro transepithelial electrical resistance assay.
19. A pharmaceutical composition, comprising: the protein of any one of claims 1-17 and a pharmaceutically acceptable carrier.
20. A method of treating a gastrointestinal epithelial cell barrier function disorder, comprising:
    a. administering to a patient in need thereof a pharmaceutical composition, comprising:
        i. a therapeutic protein comprising an amino acid sequence having at least about 85% sequence identity to SEQ ID NO: 3, SEQ ID NO: 7, SEQ ID NO: 11, SEQ ID NO: 13, SEQ ID NO: 15, SEQ ID NO: 17, and/or SEQ ID NO: 19; and
        ii. a pharmaceutically acceptable carrier.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

Molodecky et al. 2012, Increasing incidence and prevalence of the inflammatory bowel diseases with time, based on systematic review, Gastroenterology 142(1): 46-54.

Aroniadis et al., 2013, Fecal microbiota transplantation: past, present and future, Curr. Opin. Gastroenterol. 29(1): 79-84.

Maloy et al., 2011, Intestinal homeostasis and its breakdown in inflammatory bowel disease, Nature 474(7351): 298-306.

Needleman et al., 1970, A general method applicable to the search for similarities in the amino acid sequence of two proteins J. Mol. Biol., 48(3): 444-453.

Myers et al., 1988, Optimal alignments in linear space, CABIOS 4: 11-17.

Altschul, et al., 1990, Basic local alignment search tool, J. Mol. Biol. 215: 403-410.

Altschul et al., 1997, Gapped BLAST and PSI-BLAST: a new generation of protein database search programs, Nucleic Acids Res. 25(17): 3389-3402.

Henikoff et al., 1992, Amino acid substitution matrices from protein blocks, Proc. Natl. Acad. Sci. 89(22): 10915-10919.

Karlin et al., 1993, Applications and statistics for multiple high-scoring segments in molecular sequences, Proc. Natl. Acad. Sci. 90: 5873-5877.

Higgins et al., 1988, CLUSTAL: a package for performing multiple sequence alignment on a microcomputer, Gene 73: 237-244.

Person et al., 1988, Improved tools for biological sequence comparison, Proc. Natl. Acad. Sci. 85: 2444-2448.

Bowie et al., 1990, Deciphering the message in protein sequences: tolerance to amino acid substitutions, Science 247: 1306-1310.

IUPAC Commission on the Nomenclature of Organic Chemistry (CNOC) and IUPAC-IUB Commission on Biochemical Nomenclature (CBN), 1975, Nomenclature of α-Amino Acids, (Recommendations 1974), Biochemistry 14: 449-462.

Remington's Pharmaceutical Sciences, 17th edition, Alfonso R. Gennaro (Ed.), Mark Publishing Company, Easton, Pa., USA, 1985.

Encyclopaedia of Pharmaceutical Technology, 3rd edition, James Swarbrick (Ed.), Informa Healthcare USA (Inc.), NY, USA, 2007.

Berge et al., 1977, Pharmaceutical salts, J. Pharm. Sci. 66: 1-19.

Handbook of Pharmaceutical Salts: Properties, Selection, and Use, Stahl and Wermuth, Wiley-VCH, 2002.

In re Bergstrom, 427 F.2d 1394, (CCPA 1970)

In re Bergy, 596 F.2d 952 (CCPA 1979)

Parke-Davis & Co. v. H.K. Mulford & Co., 189 F. 95 (S.D.N.Y. 1911) aff'd in part, rev'd in part, 196 F. 496 (2d Cir. 1912)

Merck & Co., Inc., v. Olin Mathieson Chemical Corporation, 253 F.2d 156 (4th Cir. 1958)

Horhota et al., 2006, Glycerol nucleoside triphosphates: Synthesis and polymerase substrate activities, Organic Letters 8: 5345-5347.

Botoman et al., 1998, Management of Inflammatory Bowel Disease, Am. Fam. Physician, 57(1): 57-68.

Neurath, 2014, Cytokines in Inflammatory Bowel Disease, Nature Reviews Immunology 14: 329-342.

Zhang et al., 2007, Cytokines, Inflammation and Pain, Int. Anesthesiol. Clin. 45(2): 27-37.

Strober et al., Proinflammatory cytokines in the pathogenesis of inflammatory bowel diseases, Gastroenterology 140 (6): 1756-1767.

Boltin et al., 2013, Mucin Function in Inflammatory Bowel Disease: An Update, J. Clin. Gastroenterol. 47(2):106-111.

Kim et al., 2012, Investigating Intestinal Inflammation in DSS-induced Model of IBD, Journal of Visualized Experiments, 60: 2-6.

Levesque et al., 2015 Converging goals of treatment of inflammatory bowel disease from clinical trials and practice, Gastroenterology 148: 37-51.

Best et al., 1976, Development of a Crohn's disease activity index. National Cooperative Crohn's Disease Study, Gastroenterol. 70: 439-444.

Johansson, et al., 2014, Bacteria penetrate the normally impenetrable inner colon mucus layer in both murine colitis models and patients with ulcerative colitis, Gut 63:281-291.

Simmonds et al., 2014, Paneth cell metaplasia in newly diagnosed inflammatory bowel disease in children, BMC Gastroenterol. 14:93.

Gassler et al., 2001, Inflammatory bowel disease is associated with changes of enterocytic junctions, Am. J. Physiol. Gastrointest. Liver Physiol. 281:G216-G228.

Dewi, et al., 2004, In vitro assessment of human endothelial cell permeability: effects of inflammatory cytokines and dengue virus infection. J. Virol. Methods. 121: 171-180.

Mandic, et al., 2004, Evaluation of head and neck squamous cell carcinoma invasiveness by the electrical resistance breakdown assay, Clin. Exp. Metast. 21: 699-704.

Dewi, et al., 2008, Peripheral blood mononuclear cells increase the permeability of dengue virus-infected endothelial cells in association with down-regulation of vascular endothelial cadherin, J. Gen. Virol. 89:642-652.

Sands, 2004, From symptom to diagnosis: clinical distinctions among various forms of intestinal inflammation, Gastroenterology 126: 1518-1532.

Danese et al., 2006, Etiopathogenesis of inflammatory bowel diseases, World J. Gastroenterol. 12: 4807-4812.

Duncan, S. H., Aminov, R. I., Scott, K. P., Louis, P., Stanton, T. B., Flint, H. J. (2006). Proposal of *Roseburia faecis* sp. nov., *Roseburia hominis* sp. nov. and *Roseburia inulinivorans* sp. nov., based on isolates from human faeces. *Int. J. Syst. Evol. Microbiol*. Vol. 56, pgs. 2437-2441.

International Human Genome Sequencing Consortium (2004) Finishing the euchromatic sequence of the human genome. Nature. 431, 931-45.

Jensen O. N. (2004) Modification-specific proteomics: Characterization of post-translational modifications by mass spectrometry. Curr Opin Chem Biol. 8, 33-41.

Ayoubi T. A. and Van De Ven W. J. (1996) Regulation of gene expression by alternative promoters. FASEB J. 10, 453-60.

Walsh C. (2006) Posttranslational modification of proteins: Expanding nature's inventory. Englewood, Colo.: Roberts and Co. Publishers. xxi, 490 p. p.

Gaston B. M. et al. (2003) S-nitrosylation signaling in cell biology. Mol Interv. 3, 253-63.

Jaffrey S. R. and Snyder S. H. (2001) The biotin switch method for the detection of S-nitrosylated proteins. Sci STKE. 2001, pl1.

Han P. and Chen C. (2008) Detergent-free biotin switch combined with liquid chromatography/tandem mass spectrometry in the analysis of S-nitrosylated proteins. Rapid Commun Mass Spectrom. 22, 1137-45.

Imai S. et al. (2000) Transcriptional silencing and longevity protein SIR2 is an NAD-dependent histone deacetylase. Nature. 403, 795-800.

Glozak M. A. et al. (2005) Acetylation and deacetylation of non-histone proteins. Gene. 363, 15-23.

Yang X. J. and Seto E. (2008) Lysine acetylation: Codified crosstalk with other posttranslational modifications. Mol Cell. 31, 449-61.

Bratt, et al., "A phase 1 trial with transgenic bacteria expressing interleukin-10 in Crohn's disease," Clinical Gastroenterology and Hepatology, 2006, Vol. 4, pgs. 754-759.

Shigemori, et al., "Oral delivery of *Lactococcus lactis* that secretes bioactive heme oxygenase-1 alleviates development of acute colitis in mice," Microbial Cell Factories, 2015, Vol. 14:189.

Steidler, et al., "Treatment of murine colitis by *Lactococcus lactis* secreting interleukin-10," Science, 2000, Vol. 289, pgs. 1352-1355.

Hanniffy, et al., "Mucosal delivery of a pneumococcal vaccine using *Lactococcus lactis* affords protection against respiratory infection," Journal of Infectious Diseases, 2007, Vol. 195, pgs. 185-193.

Vandenbroucke, et al., "Active delivery of trefoil factors by genetically modified *Lactococcus lactis* prevents and heals acute colitis in mice," Gastroenterology, 2004, Vol. 127, pgs. 502-513.

Sheth, et al., "Manipulating bacterial communities by in situ microbiome engineering," Trends in Genetics, 2016, Vol. 32, Issue 4, pgs. 189-200.

Lemer et al., "Dysbiosis may trigger autoimmune diseases via inappropriate post-translational modification of host proteins," Frontiers in Microbiology, 2016, Vol. 7, Article 84.

Machiels, K., M. Joossens, J. Sabino, V. De Preter, I. Arijs, V. Eeckhaut, V. Ballet, K. Claes, F. Van Immerseel, K. Verbeke, M. Ferrante, J. Verhaegen, P. Rutgeerts, and S. Vermeire. 2014. A decrease of the butyrate-producing species *Roseburia hominis* and *Faecalibacterium prausnitzii* defines dysbiosis in patients with ulcerative colitis. Gut 63: 1275-1283.

Patterson, A. M., I. E. Mulder, A. J. Travis, A. Lan, N. Cerf-Bensussan, V. Gaboriau-Routhiau, K. Garden, E. Logan, M. I. Delday, A. G. P. Coutts, E. Monnais, V. C. Ferraria, R. Inoue, G. Grant, and R. I. Aminov. 2017.

Human Gut Symbiont *Roseburia hominis* Promotes and Regulates Innate Immunity. Front Immunol 8: 1166.

Shawki, A., and D. F. McCole. 2017. Mechanisms of Intestinal Epithelial Barrier Dysfunction by Adherent-Invasive *Escherichia coli*. Cell Mol Gastroenterol Hepatol 3: 41-50.

What is claimed is:

1. A method of treating a disorder, the method comprising: administering to a patient in need thereof a pharmaceutical composition comprising:
   i. a therapeutic protein comprising an amino acid sequence having at least 95% sequence identity to SEQ ID NO: 19; and
   ii. a pharmaceutically acceptable carrier,
   wherein the disorder is at least one selected from the group consisting of: inflammatory bowel disease, Crohn's disease, ulcerative colitis, pouchitis, irritable bowel syndrome, *Clostridium difficile* infections, celiac disease, necrotizing enterocolitis, short bowel syndrome, GI mucositis, chemotherapy induced mucositis, radiation induced mucositis, oral mucositis, and pediatric versions of the aforementioned diseases.

2. The method of claim 1, wherein the therapeutic protein comprises an amino acid sequence having at least about 97% sequence identity to SEQ ID NO: 19.

3. The method of claim 1, wherein the therapeutic protein comprises an amino acid sequence having at least about 98% sequence identity to SEQ ID NO: 19.

4. The method of claim 1, wherein the therapeutic protein comprises an amino acid sequence having at least about 99% sequence identity to SEQ ID NO: 19.

5. The method of claim 1, wherein the therapeutic protein comprises the amino acid sequence of SEQ ID NO: 19.

6. The method of claim 1, wherein administering comprises rectal, parenteral, intravenous, topical, oral, dermal, transdermal, or subcutaneous administration.

7. The method of claim 1, wherein administering is to the: mouth, gastrointestinal lumen, and/or intestines of the patient.

8. The method of claim 1, wherein the patient experiences a reduction in at least one symptom associated with the disorder.

9. The method of claim 1, wherein the patient experiences a reduction in at least one symptom associated with the disorder selected from the group consisting of: abdominal pain, blood in stool, pus in stool, fever, weight loss, frequent diarrhea, fatigue, reduced appetite, tenesmus, and rectal bleeding.

10. The method of claim 1, wherein treating comprises one or more of: reducing gastrointestinal inflammation in the patient, reducing intestinal mucosal inflammation in the patient, increasing the production of mucin in intestinal tissue in the patient, increasing intestinal epithelium wound healing in the patient, and increasing intestinal epithelial cell proliferation in the patient.

11. The method of claim 1, further comprising: administering at least one second therapeutic agent to the patient.

12. The method of claim 1, wherein the therapeutic protein comprises the amino acid sequence of SEQ ID NO: 19 with a mutation of the amino acid at position 147 to valine.

13. The method of claim 1, wherein the therapeutic protein comprises the amino acid sequence of SEQ ID NO: 19 with a mutation of the amino acid at position 151 to serine.

14. The method of claim 1, wherein the therapeutic protein comprises the amino acid sequence of SEQ ID NO: 19 with a mutation of the amino acid at position 147 to valine, and a mutation of the amino acid at position 151 to serine.

15. The method of claim 1, wherein the therapeutic protein comprises the amino acid sequence of SEQ ID NO: 19 with a mutation of the amino acid at position 84 to aspartic acid.

16. The method of claim 1, wherein the therapeutic protein comprises the amino acid sequence of SEQ ID NO: 19 with a mutation of the amino acid at position 84 to aspartic acid, a mutation of the amino acid at position 147 to valine, and a mutation of the amino acid at position 151 to serine.

17. The method of claim 1, wherein the therapeutic protein comprises the amino acid sequence of SEQ ID NO: 19 with a mutation of the amino acid at position 83 to serine.

18. The method of claim 1, wherein the therapeutic protein comprises the amino acid sequence of SEQ ID NO: 19 with a mutation of the amino acid at position 83 to serine, a mutation of the amino acid at position 147 to valine, and a mutation of the amino acid at position 151 to serine.

19. The method of claim 1, wherein the therapeutic protein comprises the amino acid sequence of SEQ ID NO: 19 with a mutation of the amino acid at position 53 to serine.

20. The method of claim 1, wherein the therapeutic protein comprises the amino acid sequence of SEQ ID NO: 19 with a mutation of the amino acid at position 53 to serine, a mutation of the amino acid at position 84 to aspartic acid, a mutation of the amino acid at position 147 to valine, and a mutation of the amino acid at position 151 to serine.

21. The method of claim 1, wherein the therapeutic protein comprises the amino acid sequence of SEQ ID NO: 19 with a mutation of the amino acid at position 53 is serine, a mutation of the amino acid at position 83 to serine, a mutation of the amino acid at position 147 to valine, and a mutation of the amino acid at position 151 to serine.

22. The method of claim 1, wherein the therapeutic protein comprises the amino acid sequence of SEQ ID NO: 19 with a mutation of the amino acid at position 147, the amino acid at position 151, the amino acid at position 83, and/or the amino acid at position 53.

23. The method of claim 1, wherein the disorder is Crohn's disease or ulcerative colitis.

24. The method of claim 1, wherein the therapeutic protein comprises a polypeptide encoded by the nucleic acid sequence of SEQ ID NO: 20.

* * * * *